US008653023B1

(12) United States Patent
Kanthasamy

(10) Patent No.: US 8,653,023 B1
(45) Date of Patent: Feb. 18, 2014

(54) DUAL BENEFICIAL EFFECT OF DOPAMINE ENHANCING AND NEUROPROTECTIVE ACTIONS OF PKC DELTA INHIBITORS FOR TREATMENT OF PARKINSON'S DISEASE

(75) Inventor: Anumantha G. Kanthasamy, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 1882 days.

(21) Appl. No.: 11/479,173

(22) Filed: Jun. 30, 2006

(51) Int. Cl.
*A61P 25/16* (2006.01)
*A61P 25/28* (2006.01)

(52) U.S. Cl.
USPC .............................................. 514/2.1; 514/7.5

(58) Field of Classification Search
None
See application file for complete search history.

(56) References Cited

U.S. PATENT DOCUMENTS

| 7,632,819 B1 | 12/2009 | Kanthasamy | |
|---|---|---|---|
| 2002/0182588 A1* | 12/2002 | Kufe et al. | 435/4 |

FOREIGN PATENT DOCUMENTS

WO   WO 2006/060196 A2   6/2006

OTHER PUBLICATIONS

Kink et al. Nature Neurosc 7: 105-110, 2004.*
Anantharam et al Ann NY Acad Sci 1035: 271-289, 2004.*
Dou, Q. Ping, "RB and Apoptotic Cell Death", Frontiers in Bioscience 3, d419-430, Apr. 16, 1998.
Kanthasamy, Anumantha G., "Role of Proteolytic Activation of Protein Kinase Cdelta in Oxidative Stress-Induced Apoptosis", Antioxidants & Redox Signaling, 5(5):609-620, 2003.
Kaul, Siddharth, "Caspase-3 dependent proteolytic activation of protein kinase Cdelta mediates and regulates 1-methyl-4-phenylpyridinium (MPP+)-induced apoptotic cell death in dopaminergic cells: relevance to oxidative stress in dopaminergic degeneration", European Journal of Neuroscience, vol. 18, pp. 1387-1401, 2003.
Kitazawa, M., "Dieldrin induces apoptosis by promoting caspase-3-dependent proteolytic cleavage of protein kinase Cdelta in dopaminergic cells: relevance to oxidative stress and dopaminergic degeneration", Neuroscience, 119, pp. 945-964, 2003.
Kitazawa, Masashi, "Activation of protein kinase Cdelta by proteolytic cleavage contributes to manganese-induced apoptosis in dopaminergic cells: protective role of Bcl-2", Biochemical Pharmacology 69, pp. 133-146, 2005.
Martelli, A.M., "Nuclear protein kinase C isoforms and apoptosis", European Journal of Histochemistry, vol. 48:89-94 2004.
Spitaler, Martin, "Protein kinase C and beyond", Nature Immunology, 5(8):785-790, Aug. 2004.
Kaul, Siddharth et al., "Caspase-3 Dependent Proteolytic Activation of Protein Kinase Cδ Mediates and Regulates 1-Methyl-4-Phenylpyridinium (MPP+)-Induced Apoptotic Cell Death in Dopaminergic Cells: Relevance to Oxidative Stress in Dopaminergic Degeneration", European Journal of Neuroscience, vol. 18, pp. 1387-1401, 2003.
Kaul, Siddharth et al., "Tyrosine Phosphorylation Regulates the Proteolytic Activation of Protein Kinase Cδ in Dopaminergic Neuronal Cells", The Journal of Biological Chemistry, vol. 280, No. 31, Aug. 5, 2005, pp. 28721-28730.
Yang, Yongjie et al., "Suppression of Caspase-3-Dependent Proteolytic Activation of Protein Kinase Cδ by Small Interfering RNA Prevents MPP+-Induced Dopaminergic Degeneration" Molecular and Cellular Neuroscience, 25 (2004), pp. 406-421.

* cited by examiner

*Primary Examiner* — Daniel E Kolker
*Assistant Examiner* — Aditi Dutt
(74) *Attorney, Agent, or Firm* — McKee, Voorhees & Sease, P.L.C.

(57) ABSTRACT

The present invention describes novel pharmaceutical compositions and methods for treatment of diseases, disorders, or conditions characterized by dopamine deficiency, including Alzheimer's disease, Parkinson's disease, Tourette's syndrome, schizophrenia, Huntington's disease, symptoms of attention deficit hyperactivity disorder, drug abuse and clinical depression. The treatment of the present invention utilizes PKCd inhibitors that have the dual benefit of increasing the levels of dopamine in the central nervous system while also protecting neuronal cells from neurodegeneration. The method and pharmaceutical compositions can be used to treat diseases, disorders, or conditions associated with neurodegeneration such as Parkinson's disease, Huntingson's disease, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke, Huntington disease (HD), amyotrophic lateral sclerosis (ALS), cardiovascular diseases, inflammatory diseases, spinal cord trauma, and head injury.

15 Claims, 19 Drawing Sheets

A

B  Substantia Nigra

C  PC12 cells

SEQUENCE LISTING

```
<160> NUMBER OF SEQ ID NOS: 19

<210> SEQ ID NO 1
<211> LENGTH: 29
<212> TYPE: DNA
<213> ORGANISM: rattus norvegicus

<400> SEQUENCE: 1
aagattcact acatcaagaa ccctgtctc                                29

<210> SEQ ID NO 2
<211> LENGTH: 29
<212> TYPE: DNA
<213> ORGANISM: rattus norvegicus

<400> SEQUENCE: 2
aagttcttga tgtagtgaat ccctgtctc                                29

<210> SEQ ID NO 3
<211> LENGTH: 29
<212> TYPE: DNA
<213> ORGANISM: rattus norvegicus

<400> SEQUENCE: 3
aaggtacttt gcaatcaagt acctgtctc                                29

<210> SEQ ID NO 4
<211> LENGTH: 29
<212> TYPE: DNA
<213> ORGANISM: rattus norvegicus

<400> SEQUENCE: 4
aatacttgat tgcaaagtac ccctgtctc                                29

<210> SEQ ID NO 5
<211> LENGTH: 29
<212> TYPE: DNA
<213> ORGANISM: rattus norvegicus

<400> SEQUENCE: 5
aacatcaggc ttcacccctt tcctgtctc                                29

<210> SEQ ID NO 6
<211> LENGTH: 29
<212> TYPE: DNA
<213> ORGANISM: rattus norvegicus

<400> SEQUENCE: 6
```

-continued

```
aaaaagggggt gaagcctgat gcctgtctc                              29

<210> SEQ ID NO 7
<211> LENGTH: 29
<212> TYPE: DNA
<213> ORGANISM: rattus norvegicus

<400> SEQUENCE: 7
aactgtttgt gaatttgcct tcctgtctc                               29

<210> SEQ ID NO 8
<211> LENGTH: 29
<212> TYPE: DNA
<213> ORGANISM: rattus norvegicus

<400> SEQUENCE: 8
aaaaggcaaa ttcacaaaca gcctgtctc                               29

<210> SEQ ID NO 9
<211> LENGTH: 21
<212> TYPE: RNA
<213> ORGANISM: Homo sapiens

<400> SEQUENCE: 9
aauccacuac aucaagaacu u                                       21

<210> SEQ ID NO 10
<211> LENGTH: 21
<212> TYPE: RNA
<213> ORGANISM: Homo sapiens

<400> SEQUENCE: 10
guucuugaug uaguggauuu u                                       21

<210> SEQ ID NO 11
<211> LENGTH: 21
<212> TYPE: RNA
<213> ORGANISM: Homo sapiens

<400> SEQUENCE: 11
cuguguguga aucugcuuuu u                                       21

<210> SEQ ID NO 12
<211> LENGTH: 21
<212> TYPE: RNA
<213> ORGANISM: Homo sapiens

<400> SEQUENCE: 12
aaagcagauu cacacacagu u                                       21

<210> SEQ ID NO 13
<211> LENGTH: 22
<212> TYPE: RNA
<213> ORGANISM: rattus norvegicus

<400> SEQUENCE: 13
gcaucuccuu caauuccuau uu                                      22

<210> SEQ ID NO 14
<211> LENGTH: 22
<212> TYPE: RNA
<213> ORGANISM: rattus norvegicus

<400> SEQUENCE: 14
```

-continued

```
<210> SEQ ID NO 15
<211> LENGTH: 23
<212> TYPE: RNA
<213> ORGANISM: rattus norvegicus

<400> SEQUENCE: 15
gcaguuucua cacagcaaag guu                                              23

<210> SEQ ID NO 16
<211> LENGTH: 23
<212> TYPE: RNA
<213> ORGANISM: rattus norvegicus

<400> SEQUENCE: 16
ccuuugcugu guagaaacug cuu                                              23

<210> SEQ ID NO 17
<211> LENGTH: 23
<212> TYPE: RNA
<213> ORGANISM: rattus norvegicus

<400> SEQUENCE: 17
gccucaccga uucaagguuu auu                                              23

<210> SEQ ID NO 18
<211> LENGTH: 23
<212> TYPE: RNA
<213> ORGANISM: rattus norvegicus

<400> SEQUENCE: 18
uaaaccuuga aucggugagg cuu                                              23

<210> SEQ ID NO 19
<211> LENGTH: 4
<212> TYPE: PRT
<213> ORGANISM: Homo sapiens

<400> SEQUENCE: 19

Asp Ile Pro Asp
1
```

DUAL BENEFICIAL EFFECT OF DOPAMINE ENHANCING AND NEUROPROTECTIVE ACTIONS OF PKC DELTA INHIBITORS FOR TREATMENT OF PARKINSON'S DISEASE

GRANT REFERENCE

This invention was made with government support under contract NIH No. RO1NS038644-07. The Government has certain rights in this invention.

FIELD OF THE INVENTION

This invention relates to methods and pharmaceutical compositions for regulating the levels of dopamine using a protein kinase C delta (PKCd) inhibitor. In particular, it relates to increasing the levels of dopamine in the central nervous systems (CNS) and in the treatment of diseases, disorders, and conditions where dopamine deficiencies are implicated. The invention also relates to methods of using PKCd inhibitors and pharmaceutical compositions of this invention to treat neurodegenerative diseases, disorders, and conditions, such as Parkinson's disease.

BACKGROUND OF THE INVENTION

The death or damage of neurons is a hallmark of neurodegenerative illnesses and disorders, including, for example, dementia, Alzheimer's, Huntington's, and Parkinson's disease. Parkinson's disease (PD) affects more than 1% of the population over the age of 60 in the U.S. (Allam et al., 2005; West et al., 2005). PD is believed to be caused by lack of the neurotransmitter, dopamine, in the basal ganglia of the brain. In large part, this dopamine deficiency is attributed to the degeneration of nigral dopaminergic neurons. (Przedborski, 2005). Both clinical and experimental evidence clearly demonstrates that oxidative stress and apoptosis are key cellular mechanisms that contribute to the neuronal loss (Maguire-Zeiss et al., 2005). There is no cure for PD. Treatments available at present only target symptoms of the disease. In light of the selective death of dopamine producing neurons, administration of L-dihydroxyphenylalanine (L-DOPA) remains the most widely used treatment of Parkinson's disease. However, L-dopa has limited and transient efficacy.

Current approaches fail to prevent the progression of the neurodegenerative process and sustain or increase dopamine levels. Although the pathology and clinical symptoms are well defined in PD, the cellular and molecular mechanisms underlying the selective degeneration of dopaminergic neurons still remains elusive.

Protein kinase C (PKC) belongs to a family of serine threonine protein kinases. To date, twelve isoforms in the PKC subfamily have been identified. Kanthasamy et al., 2003; Antioxidants & Redox Signaling, 5: 609-620. One such isoform is protein kinase C delta (PKCδ). Martelli A M, Mazzotti G, Capitani S, Nuclear protein kinase C isoforms and apoptosis. Eur J Histochem. 2004; 48(1):89-94.

PKCd was originally discovered by Gschwendt et al. in 1986, Gschwendt M, Kittstein W, and Marks F. A novel type of phorbol ester-dependent protein phosphorylation in the particulate fraction of mouse epidermis. Biochem Biophys Res Commun. 137: 766-74, 1986., and cloned from a rat brain cDNA library the following year. Kurkinen K M, Keinanen R A, Karhu R, and Koistinaho J. Genomic structure and chromosomal localization of the rat protein kinase Cdelta-gene. Gene 242: 115-23, 2000., Ono Y, Fujii T, Ogita K, Kikkawa U, Igarashi K, and Nishizuka Y. Identification of three additional members of rat protein kinase C family: delta-, epsilon- and zeta-subspecies. FEBS Lett. 226: 125-8, 1987. The PKCδ gene is localized on human chromosome 3, Huppi K, Siwarski D, Goodnight J, and Mischak H. Assignment of the protein kinase C delta polypeptide gene (PRKCD) to human chromosome 3 and mouse chromosome 14. Genomics 19: 161-2., 1994, rat chromosome 16, Kurkinen K M, Keinanen R A, Karhu R, and Koistinaho J. Genomic structure and chromosomal localization of the rat protein kinase Cdelta-gene. Gene 242: 115-23, 2000, and mouse chromosome 14, Huppi K, Siwarski D, Goodnight J, and Mischak H. Assignment of the protein kinase C delta polypeptide gene (PRKCD) to human chromosome 3 and mouse chromosome 14. Genomics. 19: 161-2., 1994. There exists a substantial body of evidence that indicates that PKCδ plays a fundamental role in apoptosis. PKCδ has been shown to accumulate in the nucleus of C5 cells, in response to etoposide treatment. Martelli A M, Mazzotti G, Capitani S. Nuclear protein kinase C isoforms and apoptosis. Eur J Histochem. 2004; 48(1):89-94. Overexpression of PKCδ-catalytic fragment results in nuclear localization of the PKCδ fragment and apoptosis. Martelli A M, Mazzotti G, Capitani S. Nuclear protein kinase C isoforms and apoptosis. Eur J Histochem. 2004; 48(1):89-94

Recently, it was reported by the inventors that proteolytic activation of PKCd, a member of the novel PKC isoform family, plays a key role in apoptotic cell death of dopaminergic neurons in a cell culture model of PD as well as oxidative stress models (Anantharam et al., 2002; Kaul et al., 2003; Kitazawa et al., 2003; Yang et al., 2004; Latchoumycandane et al., 2005). It is believed that active PKCd binds to the carboxyl-terminus of DNA-dependent protein kinase (DNA-PK), an enzyme involved in the repair of DNA strand breaks. Once bound, the active PKCd binds to and phosphorylates the DNA-PK. Consequently, the DNA-PK dissociates from the DNA, impedes the repair of DNA strand breaks, and results in DNA fragmentation, one of the hallmarks of apoptosis. It was demonstrated that blockade of PKCd activation by the kinase dominant negative mutant, cleavage-resistant mutant or siRNA almost completely prevented the nigral cell death (Kaul et al., 2003; Kitazawa et al., 2003; Anantharam et al., 2004; Yang et al., 2004; Latchoumycandane et al., 2005).

BRIEF SUMMARY OF THE INVENTION

The present invention is based on the finding that the PKCd inhibitors participate in dopamine synthesis. The invention is further based on the observation that PKCd is involved in protein phosphorylase 2A (PP2A) activation.

In one aspect, the invention concerns a method of increasing dopamine synthesis in a dopamine producing cell of a mammal suffering from a disease state characterized by lack of dopamine in its dopamine producing cells comprising contacting a dopamine producing cell with a protein kinase C delta (PKCd) inhibitor. In a particular embodiment, the PKCd inhibitor is (3-[(8-Cinnamoyl-5,7-dihydroxy-2,2-dimethyl-2H-1-benzopyran-6-yl)methyl]-2',4',6'-trihydroxy-5-methylacetophenone, commonly referred to as rottlerin. In one aspect, the a dopamine producing cell is a dopaminergic neuron.

In another aspect, the invention concerns a method for identifying PKCd inhibitors. The methods of the present invention include identifying PKCd inhibitors that decrease expression of PKCd in a cell comprising: contacting a cell having endogenous or exogenous PKCd with a compound, measuring the level of PKCd in the cell, and comparing the level of PKCd that occurs in the cell in the presence of the test compound with the level of PKCd that occurs in a cell in the absence of the test compound. In another aspect, the present invention provides for determining the effect of the test compound on the PKCd kinase activity, e.g. determining whether phosphorylation of the PKCd polypeptide and/or activation of PKCd polypeptide in the presence of said compound is changed compared to the phosphorylation and/or activation of the PKCd polypeptide in the absence of said compound.

In a further aspect, the invention concerns a method of increasing dopamine levels in a central nervous system of a mammal in need thereof, said method comprising administering to a mammal in need thereof a protein kinase C delta (PKCd) inhibitor, thereby increasing dopamine levels. In the preceding aspects of the invention, the inhibitors of PKCd identified in accordance with the present invention can be included in pharmaceutical compositions and administered to a mammal suffering from or at risk of a disease, disorder, or condition associated with dopamine deficiencies, including but not limited to Alzheimer's disease, Parkinson's disease, Tourette's syndrome, schizophrenia, Huntington's disease, symptoms of attention deficit hyperactivity disorder, drug abuse and clinical depression. In yet a further aspect, the invention concerns a pharmaceutical composition for increasing dopamine levels in a central nervous system of a mammal in need thereof comprising: a protein kinase C delta (PKCd) inhibitor and a pharmaceutically acceptable carrier.

In a still further aspect, the invention concerns a method for treating neurodegeneration of neurons in a mammal in need thereof comprising administering to a mammal in need thereof a protein kinase C delta (PKCd) inhibitor, thereby providing neuroprotection. In one aspect, the neurodegeneration is Parkinson's disease, Huntingson's disease, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke, Huntington disease (HD), amyotrophic lateral sclerosis (ALS), cardiovascular diseases, inflammatory diseases, spinal cord trauma, and head injury. In another aspect, the pharmaceutical composition may be used in the treatment of diseases, disorders, or conditions associated with neurodegeneration. In one aspect, the neuron is a sympathetic, parasympathetic, or enteric, e.g. dorsal root ganglia neurons, motorneurons, and central neurons, e.g. neurons from the spinal cord.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE PREFERRED EMBODIMENT

Figure 1:
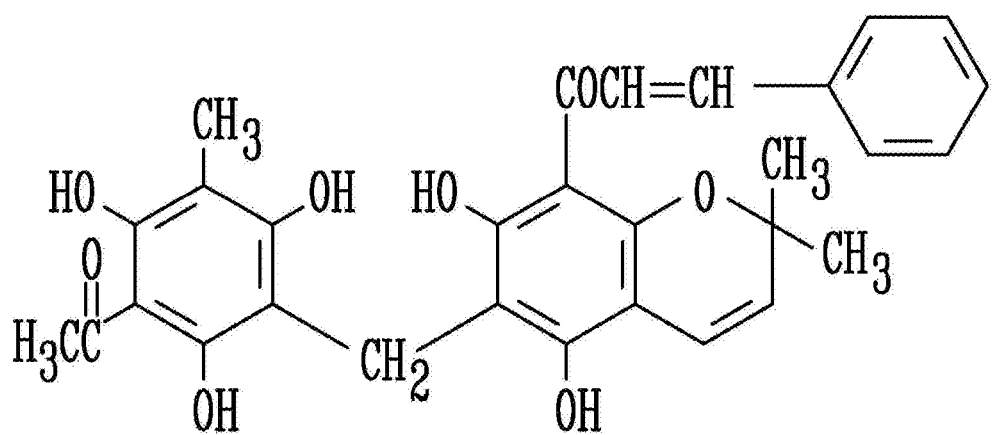
FIG. 1. Chemical structure of rottlerin.

The present invention is based on the discovery that inhibition of PKCd increases dopamine synthesis in neuronal cells. Use of PKCd inhibitors and methods of the invention increased levels of dopamine by 4-fold in the striatum in PKCd knockout mice. The present invention also provides methods for increasing levels of dopamine in a central nervous system in a mammal by administering PKCd inhibitors. The present invention surprisingly demonstrates that administering a PKCd inhibitor provides a dual benefit of increasing the levels of dopamine in the central nervous system while also protecting the neuronal cells from neurodegeneration. Thus, the invention includes a method for treating PD by administering a PKCd inhibitor, in particular (3-[(8-Cinnamoyl-5,7-dihydroxy-2,2-dimethyl-2H-1-benzopyran-6-yl)methyl]-2',4',6'-trihydroxy-5-methylacetophenone, commonly referred to as rottlerin.

DEFINITIONS

As used herein, the term "PKCd inhibitor" includes any compound capable of downregulating, decreasing, reducing, suppressing or inactivating the amount and/or activity of protein kinase C delta (PKCd). Generally, said inhibitors may be proteins, oligo- and polypeptides, polynucleotides, genes, lipid, polysaccharide, drugs, small chemical molecules, or other chemical moieties. Inhibitors for use with the invention may function to inhibit PKCd by any number of ways, including decreasing PKCd mRNA or protein levels or by blocking the activation of PKCd or its activity, for example, through inhibiting or decreasing proteolytic cleavage of PKCd using a PKCd peptide cleavage inhibitor. Compounds that decrease activity of PKCd downstream of PKCd in its pathway and decrease products or activity of PKCd targets, for example, PP2A and TH, or decrease activity upstream of PKCd are also within the scope of PKCd inhibitors of the present invention.

As used herein, the term "neurodegeneration" refers the damage or death of a cell in the central nervous system, for example, a neuron. Neurodegeneration refers to any pathological changes in neuronal cells, including, without limitation, death or loss of neuronal cells and any changes that precede cell death. The pathological changes may be spontaneous or may be induced by any event and include, for example, pathological changes associated with apoptosis. The neurons may be any neurons, including without limitation sensory, sympathetic, parasympathetic, or enteric, e.g. dorsal root ganglia neurons, motorneurons, and central neurons, e.g. neurons from the spinal cord.

As used herein, the terms "neurodegenerative disorder" or "neurodegenerative disease" refer broadly to disorders or diseases that affect the nervous system having damage or death of a cell of the central nervous system, including but not limited to Parkinson's disease, Alzheimer's disease, Huntington's disease and amyotrophic lateral sclerosis.

As used herein, the term "dopaminergic neurons" refers broadly to neurons which produce the neurotransmitter dopamine.

As used herein, the term "compound" refers to a polynucleotide, a protein, a polypeptide, a peptide, an antibody, an immunoglobulin, a ligand, a cytokine, a growth factor, a nucleic acid, a lipid, membrane, a carbohydrate, a drug, a prodrug, or a small molecule or a fragment thereof.

As used herein, the term "modulates" refers to the ability of a compound to alter the mRNA or protein expression level or kinase activity or phosphatase activity of a protein.

As used herein, the term "inhibiting" or "inhibits" refers to reducing or decreasing the level of mRNA or protein or activity of an enzyme, for example, a kinase.

As used herein, the terms "tyrosine hydroxylase" or "TH" refers to an enzyme required for dopamine biosynthesis. TH is a commonly accepted marker indicative of dopaminergic neurons in the substantia nigra. As used herein, a TH+ cell is a cell which immunostains positive using an anti-tyrosine hydroxylase primary antibody.

As used herein, the term "pharmaceutically acceptable carrier" refers to any carrier, diluent, excipient, wetting agent, buffering agent, suspending agent, lubricating agent, adjuvant, vehicle, delivery system, emulsifier, disintegrant, absorbent, preservative, surfactant, colorant, flavorant, or sweetener, preferably non-toxic, that would be suitable for use in a pharmaceutical composition.

As used herein, the terms "pharmaceutically effective" or "therapeutically effective" shall mean an amount of a PKCd inhibitor that is sufficient to show a meaningful patient benefit, i.e., treatment, prevention, amelioration, or a decrease in the frequency of the condition or symptom being treated. The PKCd inhibitor may be administered in the form of a pharmaceutical composition with a pharmaceutically acceptable carrier.

As used herein, the term "treating" refers to: (i) preventing a disease, disorder or condition from occurring in an animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition. For example, with respect to Parkinson's disease, treatment may be measured by quantitatively or qualitatively to determine the presence/absence of the disease, or its progression or regression using, for example, symptoms associated with the disease or clinical indications associated with the pathology.

As used herein, the term "polypeptide" is interpreted to mean a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides. "Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well-known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADPribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-link formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W. H. Freeman and Company, New York (1993) and Wold, F., Posttranslational Protein Modifications: Perspectives and Prospects, pgs. 1 12 in POSTTRANSLATIONAL COVALENT MODIFICATION OF PROTEINS, B. C. Johnson, Ed., Academic Press, New York (1983); Seifter et al., Meth. Enzymol. 182:626 646 (1990) and Rattan et al., Protein Synthesis Posttranslational Modifications and Aging, Ann. N.Y. Acad. Sci. 663: 48 62 (1992). Polypeptides may be branched or cyclic, with or without branching. Cyclic, branched and branched circular polypeptides may result from post-translational natural processes and may be made by entirely synthetic methods, as well.

As used herein, the term "polynucleotide" is interpreted to mean a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces T.

As used herein, the term dopamine (DA) includes dopamine as well as dopamine metabolites, such as L-3,4-dihydroxyphenylalanine (DOPA), 3,4-dihydroxyphenylacetic acid (DOPAC), 3,4-dihydroxyphenylacetaldehyde a (DOPAL) and homovanillnic acid (HVA).

In particular, the present invention includes a method of increasing levels of dopamine in a dopamine producing cell by contacting the dopamine producing cell with a PKCd inhibitor, thereby increasing cellular levels of dopamine. In one aspect, the dopamine producing cell is contacted with the PKCd inhibitor in vitro or ex vivo. In one aspect, the dopamine producing cell is contacted with the PKCd inhibitor in vivo. In one aspect, the dopamine producing cell is a neuron. In one aspect, the neuron is a dopaminergic neuron. In one aspect, the levels of dopamine are increased in a dopamine producing cell of a mammal suffering from a disease state characterized by lack of dopamine in dopamine producing cells, for example, Alzheimer's disease, Parkinson's disease, Tourette's syndrome, schizophrenia, Huntington's disease, symptoms of attention deficit hyperactivity disorder, drug abuse and clinical depression. The present invention also provides methods for increasing dopamine levels and for preventing neurodegeneration of neurons using PKCd inhibitors. The present invention is based on the discovery of a novel interaction of PKCd with tyrosine hydroxylase (TH). TH is the first and rate-limiting enzyme in the biosynthesis pathway of the catecholamine neurotransmitters: dopamine, epinephrine and norepinephrine and catalyzes the first step of a biochemical synthetic pathway in which L-tyrosine is converted to L-3,4-dihydroxyphenylalanine (L-dopa). The present inventor has discovered that PKCd negatively regulates TH activity and dopamine synthesis by enhancing PP2A activity in a dopaminergic neuronal system.

In one aspect, the PKCd inhibitor is (3-[(8-Cinnamoyl-5, 7-dihydroxy-2,2-dimethyl-2H-1-benzopyran-6-yl)methyl]-2',4',6'-trihydroxy-5-methylacetophenone, also referred to as rottlerin. This compound is commercially available from a number of sources including Sigma-Aldrich (St. Louis, Mo.).

In one aspect, the PKCd inhibitor is a polynucleotide, peptide, protein, lipid, polysaccharide, small molecule or drug that inhibits PKCd activity or decreases expression of PKCd directly or indirectly, for example, via caspase 3. In another aspect, the PKCd inhibitor is a polynucleotide that includes but is not limited to an antisense polynucleotide, ribozyme, RNA interference (RNAi) molecule, small hairpin RNA (shRNA), triple helix polynucleotide and the like, where the nucleotide sequence of such polynucleotides are the nucleotide sequences of DNA and/or RNA. Antisense technology may be used to achieve PKCd-specific interference, using for example, stoichiometric amounts of single-stranded nucleic acid complementary to the messenger RNA of PKCd which are introduced into the cell.

In one embodiment, an RNA interference (RNAi) molecule is used as a PKCd inhibitor, decreasing PKCd gene expression in a cell. In another aspect, the PKCd inhibitor is a siRNA molecule for targeting PKCd in a mammal, including without limitation, PKCd siRNA for a mouse, rat, monkey, or human. In one aspect, the PKCd siRNA comprises the sequence of siRNA-d-1: antisense: 5'-AAGATTCACTA-CATCAAGAACCCTGTCTC-3' (SEQ ID NO:1), sense: 5'-AAGTTCTTGATGTAGTGAATCCCTGTCTC-3' (SEQ ID NO:2). In one aspect, the PKCd siRNA comprises the sequence of siRNA-d-2:
Antisense: 5'-AAGGTACTTTGCAATCAAGTACCT-GTCTC-3' (SEQ ID NO:3), sense: 5'-AATACTTGATTG-CAAAGTACCCCTGTCTC-3' (SEQ ID NO:4). In one aspect the PKCd siRNA comprises the sequence of siRNA-d-3: Antisense: 5'-AACATCAGGCTTCACCCCTTTCCT-GTCTC-3' (SEQ ID NO:5), sense: 5'-AAAAAGGGGT-GAAGCCTGATGCCTGTCTC-3' (SEQ ID NO:6). In one aspect the PKCd siRNA comprises the sequence of siRNA-d-4: Antisense: 5'-AACTGTTTGTGAATTTGCCTTCCT-GTCTC-3' (SEQ ID NO:7), sense: 5'-AAAAGGCAAAT-TCACAAACAGCCTGTCTC-3' (SEQ ID NO:8). In another aspect, an siRNA molecule of siRNA-d-1, siRNA-d-2, siRNA-d-3, and siRNA-d-4 as described above may be used to target rat PKCd. In one aspect, the PKCd siRNA comprises the sequence of siRNA-1: sense strand: 5'-AAUCCACUA-CAUCAAGAACUU-3' (SEQ ID NO:9), antisense strand: 5'-GUUCUUGAUGUAGUGGAUUUU-3' (SEQ ID NO:10). In one aspect, siRNA molecules for the targeting human PKCd comprises the sequence of siRNA-1: sense strand: 5'-AAUCCACUACAUCAAGAACUU-3' (SEQ ID NO:9), antisense strand: 5'-GUUCUUGAUGUAGUGGAUUUU-3' (SEQ ID NO:10). The mRNA and amino acid sequence of human PKCd can be found in GenBank accession number: NM_006254 and accession number: NP_997704 respectively. In one aspect, the PKCd siRNA comprises the sequence of siRNA-2: sense: 5'-CUGUGUGUGAAU-CUGCUUUUU-3' (SEQ ID NO:11), antisense: 5'-AAAG-CAGAUUCACACACAGUU-3' (SEQ ID NO:12). In one aspect, the PKCd siRNA for targeting human PKCd comprises the sequence of siRNA-2: sense: 5'-CUGUGU-GUGAAUCUGCUUUUU-3' (SEQ ID NO:11), antisense: 5'-AAAGCAGAUUCACACACAGUU-3' (SEQ ID NO:12).

In one aspect, the PKCd siRNA comprises the sequence of siRNA-1A: Sense strand: 5'-GCAUCUCCUUCAAUUC-CUAUUU-3' (SEQ ID NO:13), antisense strand: 5'-AUAG-GAAUUGAAGGAGAUGCUU-3' (SEQ ID NO:14). In one aspect, the PKCd siRNA comprises the sequence of siRNA-2A: sense strand: 5'-GCAGUUUCUACACAGCAAAG-GUU-3' (SEQ ID NO:15), antisense strand: 5'-CCUUUGCU-GUGUAGAAACUGCUU-3' (SEQ ID NO:16). In one aspect, the PKCd siRNA comprises the sequence of siRNA-3A: sense: 5'-GCCUCACCGAUUCAAGGUUUAUU-3' (SEQ ID NO:17), antisense: 5'-UAAACCUUGAAUCG-GUGAGGCUU-3' (SEQ ID NO:18). In another aspect, an siRNA molecule of siRNA-1A, siRNA-2A, and siRNA-3A as described above may be used to target mouse PKCd. In one embodiment, the compositions and methods of the present invention includes a PKCd inhibitor of at least one PKCd siRNA. In one aspect, the PKCd inhibitor includes a combination of differing PKCd siRNA molecules. Materials and methods to produce PKCd siRNA molecules are known to one in the art and additionally are described in Kanthasany, A. G. et al. Suppression of caspase-3-dependent proteolytic activation of protein kinase C delta by small interfering RNA prevents MPP+-induced dopaminergic degeneration. Mol Cell Neurosci. 2004. 25(3):406-21, herein incorporated by reference in its entirety. The PKCd siRNA molecules may be produced by a number of methods, including the use of commercially available kits, for example, The SILENCER™ siRNA Construction Kit (Ambion, Austin, Tex.), a mammalian siRNA PKCd expression plasmid (Upstate Cell Signaling Solutions, Charlottesville, Va.), or obtained from MoleculA (Columbia, Md.).

The siRNA can be administered directly, for example, intracellularly, into a cell to mediate RNA interference (Elbashir et al., 2001, Nature 411:494 498) or administered extracellularly into a cavity, interstitial space, into the circulation of an organism, introduced orally, or may be administered by contacting the cell with a solution containing the RNA. Physical methods of introducing polynucleotides, for example, injection directly into the cell or extracellular injection into the organism, may also be used. Other methods known in the art for introducing polynucleotides to cells may be used, such as viral vectors, viruses, lipid-mediated carrier transport, chemical-mediated transport, such as calcium phosphate, electroporation, the like. siRNA can be made using, for example, chemical synthesis or in vitro or in vivo transcription. A number of expression vectors have also been developed to continually express siRNAs in transiently and stably transfected mammalian cells (Brummelkamp et al., 2002 Science 296:550 553; Sui et al., 2002, PNAS 99(6): 5515 5520; Paul et al., 2002, Nature Biotechnol. 20:505 508

In one embodiment, the PKCd inhibitor is a small hairpin RNA (shRNA), which is processed in vivo into siRNA-like molecules capable of carrying out gene-specific silencing. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. The RNA molecule may be at least 10, 12, 15, 20, 21, 22, 23, 24, 25, 30, nucleotides in length.

RNA containing a polynucleotide sequence identical to a portion of PKCd gene is preferred for inhibition. RNA sequences with insertions, deletions, and single point mutations relative to the target sequence of PKCd may also be effective for inhibition. Thus, one hundred percent sequence identity between the RNA and the target gene is not required to practice the present invention. Greater than 80% or 90% sequence identity or 100% sequence identity, between the inhibitory RNA and the portion of the PKCd is preferred. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Alternatively, the duplex region of the RNA may be defined functionally as a nucleotide sequence that is capable of hybridizing with a portion of the PKCd transcript (e.g., 400 mM NaCl, 40 mM PIPES pH 6.4, 1 mM EDTA, 50° C. or 70° C. hybridization for 12 16 hours; followed by washing). The length of the identical nucleotide sequences may be at least 25, 50, 100, 200, 300 or 400 bases.

In one aspect, the PKCd inhibitor is a PKCd peptide cleavage inhibitor. In one aspect of the present invention, a PKCd inhibitor is a PKCd peptide cleavage inhibitor in which the inhibitor includes the following amino acid motif Asp Ile Pro Asp (SEQ ID NO:19), (Aspartic Acid, Isoleucine, Proline, and Aspartic Acid). In another aspect, the PKCd inhibitor includes a polynucleotide that encodes a peptide or polypeptide containing the amino acid motif Asp Ile Pro Asp (SEQ ID NO:19) where the translated polypeptide inhibits PKCd activity as disclosed in U.S. patent application Ser. No. 11/262, 677 which is herein incorporated by reference in its entirety.

In another embodiment of the present invention, the PKCd peptide cleavage inhibitor is chemically modified to protect the inhibitor from protease degradation. Methods to prevent the protease degradation are known to one skilled in the art, including the addition of N-benzyloxycarbonyl at the N-terminal of the polypeptide. Peptides can be synthesized by methods known to one skilled in the art or isolated from cells or tissues of organisms using standard methods known in the art.

In yet another embodiment, the PKCd peptide cleavage inhibitor is chemically modified to contain a (O-methyl)fluoromethyl ketone (FMK) tail. Tails may facilitate the inhibitor in permeating cell membranes. Other tails that facilitate cell membrane permeability are well known in the art. These include, but are not limited to, N-Acetyl or chloromethyl ketone derivatives.

PKCd inhibitors can be delivered intracellularly using a lipid-mediated protein delivery system. Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP$^+$)-induced apoptotic cell death in dopaminergic cells: relevance to oxidative stress in dopaminergic degeneration. Eur J Neurosci. 2003 September; 18(6):1387-401. The incomplete cleavage of PKCδ or PKCδ-mediated apoptotic inhibition can be measured using standard techniques known to one skilled in the art. Yoshimura S, Banno Y, Nakashima S, Takenaka K, Sakai H, Nishimura Y, Sakai N, Shimizu S, Eguchi Y, Tsujimoto Y, Nozawa Y. Ceramide formation leads to caspase-3 activation during hypoxic PC12 cell death. Inhibitory effects of Bcl-2 on ceramide formation and caspase-3 activation. J Biol Chem. 1998 Mar. 20; 273(12): 6921-7 (describing a method to determine caspase activity). Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP$^+$)-induced apoptotic cell death in dopaminergic cells: relevance to oxidative stress in dopaminergic degeneration. Eur J Neurosci. 2003 September; 18(6): 1387-401) (describing the use of PKCδ-specific antibodies). Reyland M E, Anderson S M, Matassa A A, Barzen K A, Quissell D O. Protein kinase C delta is essential for etoposide-induced apoptosis in salivary gland acinar cells. J Biol Chem. 1999 Jul. 2; 274(27):19115-23.), Anantharam V, Kitazawa M, Wagner J, Kaul S, Kanthasamy A G. Caspase-3-dependent proteolytic cleavage of protein kinase Cdelta is essential for oxidative stress-mediated dopaminergic cell death after exposure to methylcyclopentadienyl manganese tricarbonyl. J Neurosci. 2002 Mar. 1; 22(5):1738-51, (describing assaying for PKCd enzymatic activity using an immunoprecipitation assay).

PKCd peptide cleavage inhibitors have been shown to inhibit PKCδ-mediated apoptotic activity in cell culture models of Parkinson's disease where apoptosis is induced by 1-methyl-4-phenylpyridinium (MPP⁺) or 6-Hydroxydopamine (6-OHDA). Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP⁺)-induced apoptotic cell death in dopaminergic cells: relevance to oxidative stress in dopaminergic degeneration. Eur J Neurosci. 2003 September; 18(6):1387-401).

The peptide cleavage inhibitor N-benzyloxycarbonyl-Asp(OMe)-Ile-Pro-Asp(OMe)-FMK (SEQ ID NO:19) effectively blocked 6-OHDA-induced DNA fragmentation. Furthermore, the inhibitor also inhibited 1-MPP⁺ induced DNA fragmentation. These results, as measured using genomic DNA fragmentation assays, indicate that these PKCd peptide cleavage inhibitors protect dopaminergic neuronal cells against apoptosis and have neuroprotective effects. Furthermore, the Inventors have found that using a concentration of N-benzyloxycarbonyl-Asp(OMe)-Ile-Pro-Asp(OMe)-FMK (SEQ ID NO:19) as low as 3 µM almost completely inhibits 6-OHDA-induced DNA fragmentation.

In the present invention, methods of screening and selecting potential therapeutic compounds for their ability to act as a PKCd peptide cleavage inhibitor are contemplated. In one embodiment, the potential PKCd peptide cleavage inhibitor is administered to living cells. If the cell does not contain a protein or polypeptide with a PCKd cleavage site upon which caspase-3 acts enzymatically or caspase-3, then vectors expressing these proteins can be transfected using standard techniques known to one skilled in the art. Therefore, the PKCδ substrate and/or caspase-3 may be endogenous or exogenous in origin. Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP⁺)-induced apoptotic cell death in dopaminergic cells: relevance to oxidative stress in dopaminergic degeneration. Eur J Neurosci. 2003 September; 18(6):1387-401. (noting that PKCδ can be delivered intracellularly using a lipid-mediated protein delivery system.).

The cleavage of PKCd into two subunits of 41 kDa and a 38 kDa by caspase-3 may be determined using Western blot analysis or enzymatic assays. For example, PKCd enzymatic activity can be assayed using an immunoprecipitation assay as previously described. Reyland M E, Anderson S M, Matassa A A, Barzen K A, Quissell D O. Protein kinase C delta is essential for etoposide-induced apoptosis in salivary gland acinar cells. J Biol Chem. 1999 Jul. 2; 274(27):19115-23., Anantharam V, Kitazawa M, Wagner J, Kaul S, Kanthasamy A G. Caspase-3-dependent proteolytic cleavage of protein kinase Cdelta is essential for oxidative stress-mediated dopaminergic cell death after exposure to methylcyclopentadienyl manganese tricarbonyl. J Neurosci. 2002 Mar. 1; 22(5):1738-51. Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP⁺)-induced apoptotic cell death in dopaminergic cells: relevance to oxidative stress in dopaminergic degeneration. Eur J Neurosci. 2003 September; 18(6):1387-401) (describing antibodies specific for PKCd).

In another embodiment of the invention, in addition to PKCd peptide cleavage inhibitors, peptides may be prepared and screened to identify those that alter PKCd activity, particularly the ability of PKCd to phosphorylate PP2A or mediate apoptosis. PKCd inhibitors for use with the methods and pharmaceutical compositions of the present invention also include dominant negative mutants, such as a nonphosphorylatable form of PKCd, which directly inhibits PKCd activity by preventing PKCd from phosphorylating normal PKCd in a cell. Dominant negative mutants include loss of function mutants, for example, PKCδ$_{D327A}$ (caspase-cleavage resistant), PKCδ$_{K376R}$ (kinase inactive) and PKCδ$_{Y311F}$ (phosphorylation defective) proteins. These dominant negatives have been demonstrated to attenuate the apoptosis of dopaminergic neurons from MPP⁺ and oxidative stress-induced apoptotic cell death (Kaul et al., 2003; Kitazawa et al., 2003; Anantharam et al., 2004; Kaul et al., 2005b; Latchoumycandane et al., 2005).

In one aspect, the PKCd inhibitor is a dominant negative PKCd protein. In one aspect, the dominant negative PKCd is a mouse caspase-cleavage resistant PKCδ$^{D327A}$-GFP, where an aspartate amino acid residue at position 327 in wild type mouse PKCd (GenBank Accession No: NM_011103) is mutated to an alanine amino acid residue (DeVries T A, Neville M C, Reyland M E, (1999) Nuclear import of PKCdelta is required for apoptosis: identification of a novel nuclear import sequence. EMBO J. 2002 Nov. 15; 21(22): 6050-60). The reference is herein incorporated in its entirety.

In one aspect, the PKCd inhibitor is a kinase inactive PKCd. In one aspect, the PKCd is the kinase inactive PKCδ$^{K376R}$-GFP, where a lysine amino acid residue at position 376 is mutated to arginine amino acid residue compared to wild type mouse PKCd (GenBank Accession No: NM_011103) as described in Li, L., Lorenzo, P. S., Bogi, K., Blumberg, P. M. and Yuspa, S. H. (1999) Protein kinase Cδ targets mitochondria, alters mitochondrial membrane potential and induces apoptosis in normal and neoplastic keratinocytes when overexpressed by an adenoviral vector. Mol. Cell. Biol., 19, 8547-8558, herein incorporated in its entirety.

In one aspect, the dominant negative PKCd is Rat tyrosine 311 phosphorylation defective FLAG-tagged PKδ$^{Y311F}$ (PKCδ$^{Y311F}$ mutant) where a tyrosine at amino acid residue at position 311 is mutated to phenylalanine amino acid residue in rat PKCδ: (GenBank accession number NM_133307, NP_579841) (Konishi H, Yamauchi E, Taniguchi H, Yamamoto T, Matsuzaki H, Takemura Y, Ohmae K, Kikkawa U, Nishizuka Y. (2001) Phosphorylation sites of protein kinase C delta in H2O2-treated cells and its activation by tyrosine kinase in vitro. Proc Natl Acad Sci USA. 2001 Jun. 5; 98(12): 6587-92), herein incorporated in its entirety.

A nucleic acid molecule encoding a PKCd dominant negative mutant, as discussed above, can be expressed from a vector, which is introduced into a cell in which it is desired to express the dominant negative mutant. An expression vector expressing, for example, a PKCd inhibitor polynucleotide can be introduced into cells using well known transfection methods (see, for example, Sambrook et al., Molecular Cloning: A laboratory manual (Cold Spring Harbor Laboratory Press 1989); Ausubel et al., Current Protocols in Molecular Biology (Green Publ., N.Y. 1989), each of which is incorporated herein by reference).

A vector also can contain elements required for replication in a prokaryotic or eukaryotic host system or both, as desired. Such vectors, which include plasmid vectors and viral vectors such as bacteriophage, baculovirus, retrovirus, lentivirus, poliovirus, rhinovirus, vaccinia virus, influenza virus, adenovirus, adeno-associated virus, herpes simplex virus, measles coronavirus, Sindbis virus, and semliki forest virus vectors, are well known and can be purchased from a commercial source (Promega, Madison Wis.; Stratagene, La. Jolla Calif.; GIBCO/BRL, Gaithersburg Md.) or can be constructed by one skilled in the art (see, for example, Meth. Enzymol., Vol. 185, D. V. Goeddel, ed. (Academic Press, Inc., 1990); Jolly, Canc. Gene Ther. 1:51-64 (1994); Flotte, J. Bioenerg. Biomemb. 25:37-42 (1993); Kirshenbaum et al., J. Clin. Invest 92:381-387 (1993), which is incorporated herein by reference).

In another aspect, the PKCd inhibitor may be a drug. In another embodiment, a PKC inhibitor directly alters the interaction of proteins in the PKCd pathway, for example, by inhibiting the activity of a kinase or phosphorylase in the pathway or by interfering with a step of the pathway. For example, a small molecule, peptide or drug may alter the association of two proteins such as PKCd kinase with PP2A in the PKCd pathway, thus preventing phosphorylation and activation of the PP2A.

Thus, PKCd inhibitors include those compounds known to inhibit PKCd activity, for example, (3-[(8-Cinnamoyl-5,7-dihydroxy-2,2-dimethyl-2H-1-benzopyran-6-yl)methyl]-2', 4',6'-trihydroxy-5-methylacetophenone (rottlerin), dominant negative mutants, or decrease expression of PKCd, for example, PKCd siRNA, or those compounds yet to be identified, for example, those identified using the screening methods described herein. The efficacy of a PKCd inhibitor for decreasing PKCd activity or PKCd expression levels may be assayed in vitro or in vivo according to methods known in the art. In vitro assays include assays that determine of inhibition the phosphorylation activity, or apoptotic activity or dopamine increasing activity of PKCd. In vitro assays may also be used to quantitate the ability of the inhibitor to bind to PKCd, for example, at its caspase 3 cleavage site.

Thus, in another aspect, the methods of the present invention include identifying PKCd inhibitors that decrease expression of PKCd in a cell comprising: contacting a cell having endogenous or exogenous PKCd with a compound, measuring the level of PKCd in the cell, and comparing the level of PKCd that occurs in the cell in the presence of the test compound with the level of PKCd that occurs in a cell in the absence of the test compound.

A decrease or reduction in the amount of PKCd, for example, the mRNA or protein level of PKCd, in the presence of the test compound, such as a PKCd siRNA or antisense PKCd RNA, as compared to the mRNA or protein level of PKCd in the absence of the test compound indicates that the test compound decreases PKCd expression. Modulation of PKCd expression levels can be assayed in a variety of ways known in the art. For example, mRNA levels can be quantitated by, e.g., Northern blot analysis, competitive polymerase chain reaction (PCR), or real-time PCR (RT-PCR). RNA analysis can be performed on total cellular RNA or poly(A)+ mRNA. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of can be quantitated in a variety of ways well known in the art, such as immunoprecipitation, Western blot analysis (immunoblotting), ELISA or fluorescence-activated cell sorting (FACS). Antibodies directed to PKCd can be identified and obtained from a variety of sources, such as from Santa Cruz Biotechnology, Inc. (Santa Cruz, Calif.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997. Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Thus, in another aspect, the method also includes identifying a compound that decreases PKCd activity in a cell having a PKCd polypeptide comprising: contacting a cell having a PKCd polypeptide with a test compound, determining an effect of the test compound on the kinase activity of the PKCd polypeptide, thereby identifying a compound that modulates the kinase activity of the PKCd polypeptide. In another aspect, the present invention provides for determining the effect of the test compound on the PKCd kinase activity, e.g. determining whether phosphorylation of the PKCd polypeptide and/or activation of PKCd polypeptide in the presence of said compound is changed compared to the phosphorylation and/or activation of the PKCd polypeptide in the absence of said compound. Phosphorylation of PKCd takes place at tyrosine residues located at positions 221, 570, 813, 1007 and/or 1008 in wild-type PKCd protein. The test compound can also be routinely screened for inhibition of apoptosis and increasing dopamine levels in vitro or in vivo.

The inhibition or reduction of PKCd activity can be determined using a variety of methods and assays routine to one skilled in the art, for example, determining the phosphorylation and/or activation of a PKCd kinase's target. Generally, a purified or partially purified PKCd kinase is incubated with a peptide comprising the target sequence of PKCd under conditions suitable for the kinase to phosphorylate its target sequence of amino acids (i.e., protein, polypeptide). The particular requirements of the kinase may be determined empirically by one of skill in the art, or the conditions that have been published for a particular kinase may be used. The extent of phosphorylation of the target peptide is determined in the presence and absence of the test compound and may be determined in the presence of varying concentrations of the test compound. The phosphorylation rate may be determined by any means known in the art including electrophorectic assays, chromatographic assays, phosphocellulose assays and the like.

In an electrophorectic assay, a radiolabled phosphate donor such as ATP or GTP is incubated with the peptide substrate in the presence of a kinase. The phosphorylated substrate versus the phosphate donor (e.g., ATP, GTP) is separated via thin-layer electrophoresis (Hunter *J. Biol. Chem.* 257:4843, 1982; incorporated herein by reference). Any matrix may be used in the electrophoresis step including polyacrylamide, cellulose, etc. The extent of phosphorylation may then be determined by autoradiography or scintillation counting.

The labeled phosphate donor may be separated from the phosphorylated amino acid sequence by standard chromatography techniques. Any matrix may be used to effect the separation including ion exchange resins, PEI cellulose, silica gel, etc. Standard column chromatography methods may be used, or HPLC methods may be used for faster cleaner separations. The radio-labeled peptides are detected by scintillation counting to determine the phosphorylation rate.

Another method which is historically the most popular is the phosphocellulose paper assay, first described by Witt et al. (Witt et al. *Anal. Biochem.* 66:253, 1975; incorporated herein by reference). Immunological methods may also be used to detect the phosphorylation of a peptide or protein substrate. For example, anti-phosphotyrosine or anti-phosphoserine antibodies may be used in the detection or precipitation of phosphorylated amino acid sequences. For example, multiple PKCd antibodies that detect the phosphorylated and unphosphorylated forms of PKCd are commercially available. (Cell signaling, Beverly, Mass. and Santa Cruz, Santa Cruz, Calif.).

In comparing the rates of phosphorylation in the presence and absence of the test compound, the compound should lead to at least a 10% decrease in the rate of phosphorylation, more preferably at least 25%, and most preferably at least 40%. These decreases are preferably obtained at micromolar concentrations of the compound and more preferably nanomolar concentrations (e.g., less than 100 nM).

In another aspect, the invention includes determining whether a potential PKCd inhibitor inhibits PKCd kinase activity. The ability of a PKCd inhibitor to decrease PKCd activity, for example, neurodegeneration or apoptotic activity, can be assessed using standard techniques known to one skilled in the art, including commercially available assays. These include apoptotic DNA Ladder assays, Cell Death Detection ELISA$^{PLUS}$ (from Roche Applied Sciences), Caspase-3 Activity Assay$^{PLUS}$ (from Roche Applied Sciences), terminal deoxynucleotidyl transferase-mediated dUTP [deoxy-uridine triphosphate] nick end labeling (TUNEL) assays. DNA-binding dyes or stains such as Hoechst 3342 or DAPI or propidium iodide may be used to assess nuclear morphology and DNA damage. Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP$^+$)-induced apoptotic cell death in dopaminergic cells: relevance to oxidative stress in dopaminergic degeneration. Eur J Neurosci. 2003 September; 18(6):1387-401. For example, when using genomic DNA fragmentation assays, the presence of genomic DNA fragmentation indicates that the candidate PKCd inhibitor has not inhibited PKCd-mediated apoptotic activity and that the inhibitor failed to inhibit an enzymatic reaction between the PKCd substrate and the caspase-3. In contrast, the absence of DNA fragmentation indicates that PKCd-mediated activity has been inhibited by the potential PKCd inhibitor.

The effect of PKCd inhibitors on dopamine synthesis, for example, dopamine levels, may be determined using any number of methods. For example, levels of DA and dopamine metabolites, for example, DOPA and DOPAC, can be determined in dopaminegeric cells or in brain tissue, for example, striatal tissues, using high-performance liquid chromatography with electrochemical detection (HPLC-EC). In another aspect, methods and pharmaceutical compositions of the present invention may be used to modulate, increase or decrease, levels of dopamine in the central nervous system, including for example, in the brain, the frontal cortex, nucleus accumbens, hypothalamus, adrenal gland and brain stem. In one aspect, levels of dopamine in the frontal cortex, nucleus accumbens, hypothalamus, adrenal gland and brain stem are increased by administering a PKCd inhibitor.

In another aspect, the invention includes a method of decreasing levels of dopamine in the central nervous system in a mammal in need thereof comprising administering a using a PKCd activator, that is a compound, that increases PKCd expression levels or activity. In another aspect, a method of decreasing levels of dopamine in a dopamine producing cell comprising contacting a dopamine producing cell with a PKCd activator is provided.

In one aspect of the methods of the invention, a PKCd inhibitor decreases PP2A activity. It has been found in accordance with the present invention that PKCd inhibitors are capable of decreasing Protein Phosphatase 2 (PP2A) activity by inhibiting an activator (phosphorylator) of PP2A, PKCd. In one embodiment, the activity of the PP2A is decreased by at least 10%. In more preferred embodiments, the activity of the phosphatase is decrease by at least 25%, or even more preferably, by at least 50%. Decreased activity of PP2A can be assessed by methods known to one of ordinary skill in the art. Suitable assays are described, for example by Honkanen et al. (1994) Toxicon 32:339 and Honkanen et al. (1990) J. Biol. Chem. 265: 19401. Briefly, phosphatase activity is determined by quantifying the [$^{32}$P] released from a $^{32}$P-labeled substrate such as phosphohistone or phosphorylase α. Decreased [$^{32}$P] release in the presence of the PKCd inhibitors of the present invention relative to control samples provides a measure of the ability of the PKCd inhibitors of the invention to decrease PP2A activity. In addition to $^{32}$P phosphorylation assays, PP2A phosphatase assays that measure PP2A's phosphatase activity may be used, for example, the serine/threonine phosphatase assay kit from Promega.

In another suitable assay, the ability of the PKCd inhibitors of the present invention to decrease the activity of protein phosphatase PP2A is assessed. The activity of PP2A may be measured using the substrate fluorescein diphosphate. Fluorescence emission from the product is measured spectrofluorometrically, for example with Perseptive Biosystems Cytofluor II (Framingham, Mass.) (excitation filter, 485 nm; emission filter, 530 nm) and the rate of increase in absorbance due to formation of dephosphorylated substrate is proportional to phosphatase activity. Thus, decreased absorbance relative to control samples provides a measure of the ability of the PKCdelta inhibitors to decrease the phosphatase activity.

In another embodiment, the method of increasing dopamine levels includes increasing the activity of TH in the presence of a PKCd inhibitor as compared to TH activity in dopaminergic cells obtained in the absence of a PKCd inhibitor. TH enzyme activity may be assessed by quantifying L-3, 4-dihydroxyphenylalanine (DOPA) levels as an index of TH activity after inhibition of DOPA carboxylase inhibitor. In another aspect, the levels of TH phosphorylated at serine 40 may be determined by immunostaining. In another embodiment, a method of increasing dopamine levels in the central nervous system of mammal in need thereof is provided. In one aspect, the mammal is suffering from dopamine deficiency. According to the present invention, methods of the present invention can be used in the treatment of diseases, disorders or conditions associated with dopamine, epinephrine and/or norepinephrine deficiencies. These include, but are not limited to, Alzheimer's disease, Parkinson's disease, Tourette's syndrome, schizophrenia, Huntington's disease, symptoms of attention deficit hyperactivity disorder, drug abuse and clinical depression (Stull et al., 1996).

In one aspect, the method includes administering a PKCd inhibitor. A PKCd inhibitor may be administered to an individual by various routes including, for example, orally or parenterally, such as intravenously, intramuscularly, subcutaneously, intraorbitally, intracapsularly, intraperitoneally, intrarectally intracisternally or by passive or facilitated absorption through the skin using, for example, a skin patch or transdermal iontophoresis, respectively. Furthermore, a composition comprising a PKCd inhibitor can be administered by injection, intubation, orally or topically, the latter of which can be passive, for example, by direct application of an ointment or powder, or active, for example, using a nasal spray or inhalant. A PKCd inhibitor also can be administered as a topical spray or an inhalant, in which case one component of the composition is an appropriate propellant.

The skilled artisan can readily perform the in vivo tests to determine, the amount or dose of PKCd inhibitor to administer, the formulation of the PKCd inhibitor, the route of administration of the PKCd inhibitor, and the time at which neurodegeneration or neuroprotection and dopamine synthesis or levels should be assessed.

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a concentration range that includes the $IC_{50}$ (i.e., the concentration of the test compound that achieves a half-maximal inhibition of symptoms) as determined in cell culture. Such information can be used to more accurately determine useful doses in humans. Levels in plasma and cerebral spinal fluid may be measured, for example, by high performance liquid chromatography.

The protocols and compositions of the invention are preferably tested in vitro, and then in vivo, for the desired therapeutic or prophylactic activity, prior to use in humans. For example, in vitro assays may be used to determine whether administration of a specific therapeutic protocol is indicated.

PKCd inhibitors for use in increasing levels of dopamine or for protection from neurodegeneration can be tested in suitable animal model systems prior to testing in humans, including principle animal models known in the art and widely used. For example, MPTP, 6-OHDA, paraquat-induced, proteosomal inhibitor-induced, and genetic models, including α-Synuclein, Parkin (PARK 2), are suitable Parkinson's disease mouse models.

The potential PKCd inhibitors can be administered by a variety of ways as discussed previously and in various formulations including as a pharmaceutical composition as discussed below. Routes and formulations are known to one skilled in the art. Optimal dose may be empirically determined. Animals can be sacrificed by focused microwave beam irradiation, for example. Striatal tissue can then be dissected and homogenates can be subjected to immunoblot analysis. The potential efficacy of these PKCd inhibitors in relieving dopamine related pathological symptoms or neurodegeneration may be assessed in animal models for disease. For example, treatment of rats or mice with 6-hyroxydopamine results in loss of dopaminergic afferent neurons, administration of quinolinic acid causes lesion of intrinsic striatal neurons, and MPTP destroys dopamine containing nerve terminals. Generally, at least two groups of animals are used in the assay, with at least one group being a control group which is administered the administration vehicle without the potential PKCd inhibitor.

In another embodiment, the method includes protecting dopamine producing cells, such as dopaminergic neurons, from neurodegeneration in a mammal. The present invention relates to methods of treating neurodegenerative diseases, for example, Parkinson's disease, using PKCd inhibitors. In particular, the present invention contemplates administering PKCd inhibitors that protect neurons from neurodegeneration.

Neurodegeneration or neuroprotection can be detected using any number of methods. Histological, neurochemical and biochemical markers of dopamine producing cells. These techniques are routine and well-known to one skilled in the art. They include, for example, terminal deoxynucleotidyl transferase-mediated dUTP-X3' nick end-labeling (TUNEL) assays that detect the free 3' OH strand breaks resulting from DNA degradation which is associated with apoptosis (J Cell Biol 199: 493, 1992). In addition, kits that measure apoptotic cell death are also commercially available and include, for example, In Situ Cell Death Detection kit; Boehringer Mannheim, Mannheim or ApoTag, Oncor, Gaithersburg, Md.). Preparation of neuronal sections for apoptosis staining using the TUNEL technique is described in (Gorczyca, (1993) Cancer Res 53:1945-51). Apoptosis can also be detected using electrophoresis of the soluble DNA fraction isolated from neuronal cells by quantifying the ladder-like appearance as described in (PNAS 95: 2498, 1998) or using DNA binding dyes Hoechst 33342 and propidium iodide flow cytometry assay described in Dengler et al., (1995) Anticancer Drugs. 6:522-32.

In one embodiment of the present invention, a method for protecting dopaminergic neurons of a mammal from apoptosis resulting from a neurodegenerative disease comprises inhibiting PKCd activity or decreasing expression of PKCd to protect dopaminergic neurons from apoptosis. In one aspect, the neurodegenerative disease is Parkinson's disease, Huntingson's disease, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke, Huntington disease (HD), amyotrophic lateral sclerosis (ALS), cardiovascular diseases, inflammatory diseases, spinal cord trauma, and head injury. In one aspect, the method includes contacting a neuron with a PKCd inhibitor that inhibits PKCd activity or decreases expression of PKCd to protect dopaminergic neurons from apoptosis.

In another embodiment, the invention includes pharmaceutical compositions for increasing the levels of dopamine in a central nervous system of a mammal in need thereof. In another aspect, the pharmaceutical compositions may be used for the treatment of a disease, disorder or condition where dopamine levels are deficient, for example, Alzheimer's disease, Parkinson's disease, Tourette's syndrome, schizophrenia, Huntington's disease, symptoms of attention deficit hyperactivity disorder, drug abuse and clinical depression. In one aspect, the PKCd inhibitor is a polynucleotide, peptide, polysaccharide, lipid, small molecule or drug. In another aspect, the PKCd inhibitor is (3-[(8-Cinnamoyl-5,7-dihydroxy-2,2-dimethyl-2H-1-benzopyran-6-yl)methyl]-2',4',6'-trihydroxy-5-methylacetophenone (rottlerin). In another aspect, the PKCd inhibitor is a siRNA molecule. While various sequences of PKCd siRNAs that may be used in methods and compositions of the present invention are described above, PKCd siRNA molecules are not intended to be limited to these specific disclosed examples. In another aspect, the PKCd inhibitor is a peptide comprising the sequence of Asp Ile Pro Asp (SEQ ID NO:19). In another aspect, the PKCd inhibitor is dominant negative PKCd mutant of normal, wild type PKCd. The compositions may comprise a therapeutically effective amount of a PKCd inhibitor and a pharmaceutically acceptable carrier. Pharmaceutical compositions for use in accordance with the present invention may be formulated in using pharmaceutically acceptable carriers or excipients. In one aspect, pharmaceutically acceptable carrier includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water may be a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. The PKCd inhibitors of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

As discussed above, various delivery systems are known and can be used to administer the PKCd inhibitors of the present invention. Methods of administering a PKCd inhibitor of the invention include, but are not limited to, parenteral administration (e.g., intradermal, intramuscular, intraperitoneal, intravenous and subcutaneous), epidural, and mucosal (e.g., intranasal and oral routes). The PKCd inhibitor may be administered by any convenient route, for example by infusion or bolus injection, by absorption through epithelial or mucocutaneous linings (e.g., oral mucosa, rectal and intestinal mucosa, etc.) and may be administered together with other agents suitable for treatment. Administration can be systemic or local.

In one embodiment, it may be desirable to administer the PKCd inhibitors locally to the area in need of treatment; this may be achieved by, for example, and not by way of limitation, local infusion, by injection, or by means of an implant.

In yet another embodiment, the PKCd inhibitor can be delivered in a controlled release or sustained release system. In one embodiment, a pump may be used to achieve controlled or sustained release.

As discussed above, the amount of the PKCd inhibitors which will be effective in the treatment, prevention or management of diseases including, but not limited to dopamine-deficient or neurodegenerative diseases, can be determined by standard research techniques. For example, the dosage of the composition which will be effective in the treatment, prevention or management of a disease can be determined by administering the composition to an animal model such as, for example, the animal models disclosed herein or known to those skilled in the art. In addition, in vitro assays may optionally be employed to help identify optimal dosage ranges. Selection of the preferred effective dose can be determined (e.g., via clinical trials) by a skilled artisan based upon the consideration of several factors which will be known to one of ordinary skill in the art. Such factors may include the disease to be treated or prevented, the symptoms involved, the patient's body mass, the patient's immune status and other factors known by the skilled artisan to reflect the accuracy of administered pharmaceutical compositions. The precise dose to be employed in the formulation will also depend on the route of administration, and the progression of the disease, and should be decided according to the judgment of the practitioner and each patient's circumstances. Effective doses may be extrapolated from dose-response curves derived from in vitro or animal model test systems.

The present invention provides kits that can be used in the above methods. In one embodiment, a kit comprises at least one PKCd inhibitor, in one or more containers, useful for the treatment of a disorder, disease, or condition associated with neurodegeneration or lack of dopamine. Optionally associated with such container(s) can be a notice in the form prescribed by a governmental agency regulating the manufacture, use or sale of pharmaceuticals or biological products, which notice reflects approval by the agency of manufacture, use or sale for human administration.

All publications, patents and patent applications identified herein are incorporated by reference, as though set forth herein in full. The invention being thus described, it will be apparent to those skilled in the art that the same may be varied

EXAMPLES

Example 1

Protection of Dopaminergic Neurons with a Protein Kinase Cδ Inhibitor Rottlerin in MPTP-Mouse Model of Parkinson's Disease Our previous studies demonstrate that caspase-3-dependent proteolytic cleavage of protein kinase Cδ (PKCδ) play a very important role in dopaminergic neuronal cell death in cell culture models of Parkinson's disease. And PKCδ inhibition can dramatically inhibited $H_2O_2$ and the parkinsonian toxin 1-methyl-4-phenylpyridinium(MPP$^+$)-induced apoptotic cell death in dopaminergic N27 cells. In the present study, a widely used PKCδ inhibitor, rottlerin, showed significant protection against MPP$^+$ induced dopaminergic neuronal cell death in mescencephalic primary culture and 1-methyl-4-phenyl-1,2,3,6-tetrahydropyridine (MPTP) induced neurotoxicity in C57 black mice model. Rottlerin significantly reduced dopamine depletion in striatum produced by MPTP administration and prevented MPTP-induced loss of dopaminergic neurons in the substantia nigra. Western blots performed on tissues from the substantia nigra following administration of MPTP showed decreases of TH expression, which was rescued by rottlerin treatment. The injection of rottlerin significantly attenuated the MPTP-induced decrease of the horizontal movement and vertical movement, which indicates a recovery of parkinsonian syndrome. These findings show that rottlerin protects dopaminergic neurons against MPTP neurotoxicity through inhibiting proapoptotic factor-PKCδ from apoptosis. Pharmacological modulation of PKCδ may offer a novel therapeutic strategy for Parkinson's disease.

Parkinson's disease (PD) is a major neurodegenerative disorder characterized by substantial loss of dopaminergic neurons in the substantia nigra, resulting in irreversible motor symptoms consisting mainly of tremors, bradykinesia and rigidity. Because the disease is progressive, it may ultimately become debilitating. Without adequate treatment and support, people with Parkinson's may tend to become depressed and withdrawn. Although it is clear that dopamine deficiency is the primary defect in Parkinson's disease, it is not clear what causes dopamine loss. At present, there is no cure for PD, the existing treatment approach for PD fails to prevent the progression of the neurodegenerative process. Although the pathology and clinical symptoms are well defined in PD, the cellular and molecular mechanisms underlying the selective degeneration of dopaminergic neurons still remains elusive. Lack of such fundamental knowledge severely hinders the development of neuroprotective strategies to circumvent the chronic progression of this debilitating neurodegenerative disorder. Recent investigations in animal models and in post-mortem human brain tissues have demonstrated that apoptosis and caspase activation is an important mode of cell death in the nigral dopaminergic degeneration (Przedborski and Jackson-Lewis 1998; Jellinger 2000; Hartmann and Hirsch 2001; Tatton, Chalmers-Redman et al. 2003). Mitochondrial injury, which is implicated in this disease, leads to release of cytochrome c into the cytoplasm where it can initiate the cascade of caspase activation by triggering the activation of caspase-9, which elicits the activation of capsase-3, leading to the morphologic changes associated with apoptosis (Friedlander 2003). At present, inhibitors of caspases and other apoptotic factor succeed in defending cells against MPTP-induced neuronal cell death. Strategies related to neurotrophins, apoptosis-regulating proteins, and endogenous inhibitors of programmed cell death implicated a new therapeutic strategy against apoptosis attributed to neurodegeneration (Garnier, Di Lorenzo et al. 1997; Gollapudi and Oblinger 1999; Adachi, Sohma et al. 2001; Alzheimer and Werner 2002; Kajta, Lason et al. 2004). While studying apoptotic signaling in cell culture models of PD, we noted that protein kinase C-delta (PKCδ), a member of the novel PKC (nPKC) isoform family, is highly expressed in nigral dopaminergic neurons and is a key substrate for caspase-3 during MPP$^+$ induced oxidative stress (Kaul, Kanthasamy et al. 2003; Yang, Kaul et al. 2004). PKCδ (72 kDa) is proteolytically cleaved by caspase-3 into a 41 kDa catalytic subunit and a 38 kDa regulatory subunit, leading to a persistent activation of the kinase during MPP$^+$ treatment in mesencephalic dopaminergic neuronal cells (N27 cells) as well as in midbrain slices (Kaul, Kanthasamy et al. 2003). Our previous study showed that Caspase-3-dependent proteolytic activation of PKCδ played a key role in oxidative stress-mediated apoptosis in dopaminergic (DA) cells in PD model (Anantharam, Kitazawa et al. 2002). Constitutively active PKCδ fragment can promote loss of cellular regulatory function in many of its substrates, resulting in rapid apoptosis in dopaminergic cells (Anantharam, Kitazawa et al. 2002).

The development of systemically active PKCδ inhibitor may therefore prove useful for treatment of neurodegenerative diseases. Rottlerin, a compound from Mallotus philippinensis, has been referred to as a specific inhibitor of PKCδ for many years, it's originally reported to inhibit PKCδ kinase activity by competing for the ATP-binding site (Gschwendt, Muller et al. 1994). This inhibitor has been used to implicate PKCδ in a variety of cellular events, including apoptosis (Chen, Ma et al. 1999; Reyland, Anderson et al. 1999; Denning, Dlugosz et al. 2000; Basu, Woolard et al. 2001). Previous studies in our lab showed that this compound could dramatically inhibited $H_2O_2$ and MPP$^+$-induced dopaminergic apoptotic cell death (Kaul, Anantharam et al. 2005). But here are no reports about efficacy of this compound in the central nervous system. In the present study, we therefore examined the efficacy of rottlerin against MPTP neurotoxicity in both mescencephalic primary culture and C57 black mice models.

Materials and Methods

Chemical and Biological Reagents.

Rottlerin, 1-methyl-4-phenylpyridinium, 1-methyl-4-phenyl-1,2,3,6-tetrahydropyridine, protease cocktail, ATP, protein-A-sepharose, protein-G-sepharose and anti-β-actin antibody were obtained from Sigma-Aldrich (St. Louis, Mo.); mouse tyrosine hydroxylase antibody was purchased from Chemicon (Temecula, Calif.); rabbit PKCδ antibody was purchased from Santa Cruz Biotechnology, Inc. (Santa Cruz, Calif.); anti-rabbit and anti-mouse secondary antibodies and the ECL chemiluminescence kit were purchased from Amersham Pharmacia Biotech. (Piscataway, N.J.). [γ-$^{32}$P]ATP was purchased from Perkin Elmer Life Science Products (Boston, Mass.). The Bradford protein assay kit was purchased from Bio-Rad Laboratories (Hercules, Calif.). Neurobasal medium, B27 supplement, L-glutamine, penicillin, and streptomycin were purchased from Invitrogen (Gaithersburg, Md.).

Mesencephalic Primary Neuron Cultures and Treatment.

Primary mesencephalic neuronal cultures were prepared from the ventral mesencephalon of gestational 16-18-day-old mice embryos as described previously (Yang et al., 2004). Mesencephalic tissues were dissected and maintained in ice-cold $Ca^{2+}$-free HESS and then dissociated in HESS solution containing trypsin-EDTA (0.25%) for 20 min at 37° C. The dissociated cells were then plated at equal density ($0.5 \times 10^6$ cells) in 30-mm-diameter tissue culture wells precoated with poly-D-lysine (1 mg/ml). Cultures were maintained in a chemically defined medium consisting of neurobasal medium fortified with B-27 supplements, L-glutamine (500 μM), penicillin (100 IU/ml), and streptomycin (100 μg/ml) (Life Technologies). The cells were maintained in a humidified $CO_2$ incubator (5% $CO_2$, 37° C.) for 24 hr and then treated with cytosine arabinoside (10 μM) for 24 hr to inhibit glial cell proliferation. Half of the culture medium was replaced every 2 days. Approximately 6-7-day-old cultures were used for experiments. Primary mesencephalic dopaminergic neuronal cells were exposed to 10 μM $MPP^+$ in the presence or absence of rottlerin (0.3 and 1 μM) for 48 hrs. Then cells were fixed and stained for TH.

Immunocytochemistry.

After treatment, the primary mesencephalic neurons were fixed with 4% paraformaldehyde and processed for immunocytochemical staining. First, non-specific sites were blocked with 5% normal goat serum containing 0.4% BSA and 0.2% Triton-X 100 in PBS for 20 min. Cells were then incubated with antibody directed against TH (1:500 dilution) overnight at 4° C. followed by incubation with Cy3-conjugated (red, 1:1000) secondary antibody for 1 hr at RT. Secondary antibody treatments were followed by incubation with Hoechst 33342 (10 μg/ml) for 3 min at room temperature to stain the nucleus. Then the coverslips containing stained cells were washed with PBS, mounted on a slide, and viewed under a Nikon inverted fluorescence microscope (Model TE-2000U); images were captured with a SPOT digital camera (Diagnostic Instruments, Sterling Heights, Mich.).

Quantification of $TH^+$ Cell Count and Neuronal Processes.

We used Metamorph software (Universal Imaging, Version 5.0) for measurement of $TH^+$ cells and neuronal processes in primary neurons from each coverslip. For measurement of TH cell count, the images were first thresholded, and then neuronal count and volume were measured using the Integrated Morphometry Analysis (IMA) function. The data were logged to an Excel spreadsheet with defined row and column positions and then analyzed. For measurement of neuronal processes, the lengths of the processes were marked by applying the region and length measurement function in the IMA. The data were exported to an Excel spreadsheet and analyzed. $TH^+$ neurons and their processes were counted in at least six individual cultures for each treatment. This method is a modified version of methodology recently used for quantification of neuronal processes.

Animal Models and Rottlerin Treatment.

Figure 8:
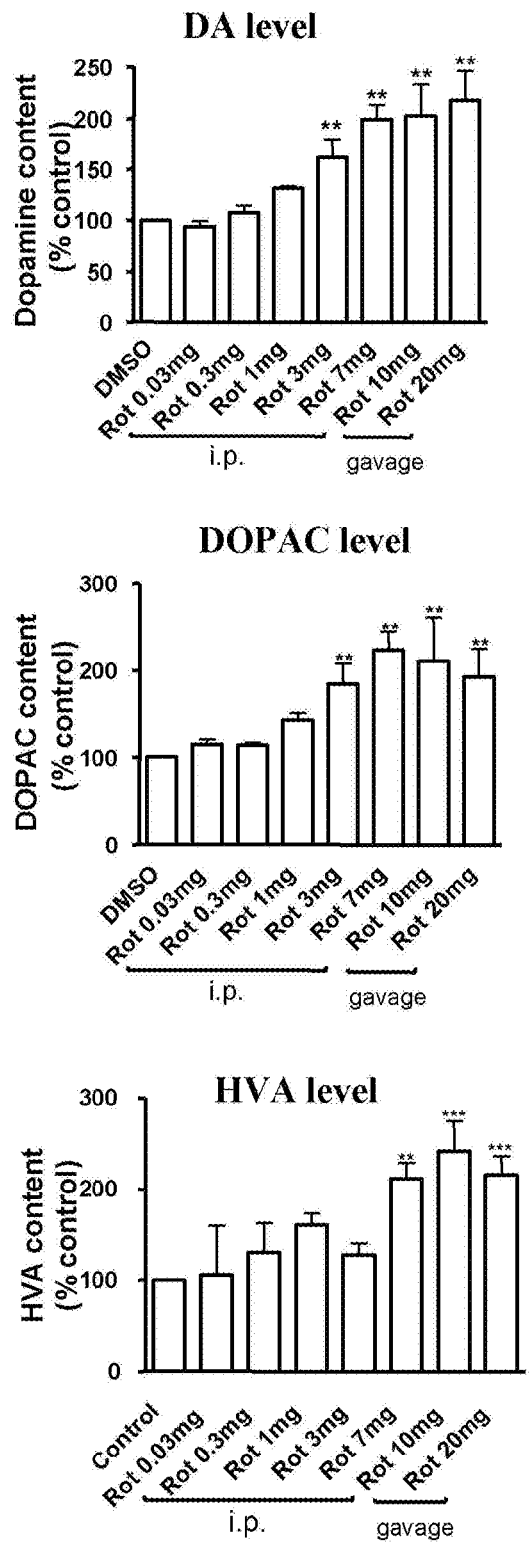
FIG. 8. Effects of Rottlerin on dopamine and its metabolites levels in the mouse striatum. Effects of different doses of rottlerin (3-20 mg/kg) on dopamine, DOPAC, and HVA. 1% DMSO was used as vehicle control. Asterisks ($P<0.01$ and $*P<0.001$) indicate significant difference compared with DMSO vehicle treated group, more than 4 animals per group.

Six to 8-week-old 26/C57/bL mice weighing 30 g were housed in standard conditions: constant temperature (22±1° C.), humidity (relative, 30%) and a 12-h light/dark cycle, and were allowed free access to food and water. The animals and protocol procedures were approved and supervised by the Committee on Animal Care (COAC) at the Iowa State University. Rottlerin was dissolved in 1% dimethyl sulfoxide (DMSO) and was administered intraperitoneally at various doses. An equal volume of DMSO was given to controls. Rottlerin and DMSO administrations were started 24 h before the injections of the MPTP and continued for 5 days in the MPTP model. In the chronic regimens of MPTP administration, MPTP in phosphate-buffered saline (PBS) was injected intraperitoneally at doses of 30 mg/kg, once a day. Mice were sacrificed 2 days after the MPTP injections, and the striata were dissected for catecholamine analysis. Additionally, rottlerin alone (0.3-20 mg/kg) was administered via intraperitoneally or orally and then brain tissues were subjected to neurochemical analyses (FIG. 8). The mesencephalons were fixed in 4% paraformaldehyde for 5 days for tyrosine hydroxylase (TH) immunostaining.

Immunohistochemistry (IHC) for TH and Cell Counting.

Brains removed following cervical dislocation were post-fixed in paraformaldehyde and used for TH immunolabelling and stereological studies. Fixed brains were cut into 30-μm sections and collected in cryoprotectant. Sections were rinsed in PBS at room temperature before immunostaining, then incubated with a anti-TH antibody as described (Thiruchelvam, McCormack et al. 2003; Thiruchelvam, Powers et al. 2004). The total number of $TH^+$ and TH Nissl-stained neurons in the SNpc were counted using the optical fractionator and previously described counting criteria (Thiruchelvam, McCormack et al. 2003; Thiruchelvam, Powers et al. 2004). After delineation of the region at low magnification (4× objective), every fourth section from the entire substantia nigra was sampled at higher magnification (100× objective) using StereoImager (Microbrightfield, Vt.).

PKCδ Kinase Assay.

PKCδ enzymatic activity was assayed using an immunoprecipitation kinase assay as described by Reyland et al. (Reyland, Anderson et al. 1999). Briefly, after treatment with rottlerin, substantia nigra brain tissue were washed once with PBS and resuspended in 1 ml of PKC lysis buffer (25 mM HEPES, pH 7.5, 20 mM β-glycerophosphate, 0.1 mM sodium orthovanadate, 0.1% Triton X-100, 0.3 M NaCl, 1.5 mM $MgCl_2$, 0.2 mM EDTA, 0.5 mM DTT, 10 mM NaF, and 4 μg/ml each aprotonin and leupeptin). The lysates were allowed to sit on ice for 30 min and centrifuged at 13,000×g for 5 min, and the supernatants were collected as cytosolic fraction. Protein concentration was determined using a Bradford assay. Cytosolic protein (0.25-0.5 mg) was immunoprecipitated overnight at 4° C. using 2 μg of anti-PKCδ antibody. The immunoprecipitates were then incubated with Protein-A Sepharose (Sigma) for 1 hr at 4° C. The protein A bound antigen-antibody complexes were then washed three times with PKC lysis buffer, three times with 2× kinase buffer (40 mM Tris, pH 7.4, 20 mM $MgCl_2$, 20 μM ATP, and 2.5 mM $CaCl_2$), and resuspended in 20 μl of 2× kinase buffer. Reaction was started by adding 20 μl of reaction buffer containing 0.4 mg Histone H1, 50 μg/ml phosphatidylserine, 4.1 μM dioleoylglycerol, and 5 μCi of [γ-$^{32}$P] ATP (3000 Ci/mM) to the immunoprecipitated samples and incubated for 10 min at 30° C. SDS gel-loading buffer (2×) was added to terminate the reaction, the samples were boiled for 5 min, and the products were separated on a 12.5% SDS-PAGE gel. The H1 phosphorylated bands were detected using a Personal Molecular Imager (FX model; Bio-Rad), and quantification was done using Quantity One 4.2.0 software.

HPLC Assay for Catecholamines.

DA and DOPAC levels in brain striatal tissues were determined by high-performance liquid chromatography with electrochemical detection (HPLC-EC); samples were prepared as described previously (Kitazawa, Anantharam et al. 2001). Briefly, neurotransmitters were extracted from samples using 0.1M perchloric acid containing 0.05% $Na_2EDTA$ and 0.1% $Na_2S_2O_5$. The extracts were filtered in 0.22 micron spin tubes and 20 μl of the samples was loaded for analysis. DA and DOPAC were separated isocratically by a reversed-phase column with a flow rate of 0.7 ml/min. An HPLC system (ESA Inc., Bedford, Mass.) with an ESA automatic sampler (model 542) was used for these experiments. The electrochemical detection (EC) system consisted of an ESA coulochem model 5100A with a microanalysis cell model 5014A and a guard cell model 5020 (ESA Inc., Bedford, Mass.). The DA and DOPAC levels were measured as pg/mg protein and expressed as percent of control.

Western Blot.

brain lysates containing equal amounts of protein were loaded in each lane and separated on a 10-12% SDS-PAGE gel as described previously (Kaul, Kanthasamy et al. 2003). After the separation, proteins were transferred to nitrocellulose membrane, and nonspecific binding sites were blocked by treating with 5% nonfat dry milk powder. The membranes were then treated with primary antibodies directed against TH (mouse monoclonal, 1:1000). The primary antibody treatments were followed by treatment with secondary HRP-conjugated anti-mouse IgG (1:2000) for 1 hr at RT. Secondary antibody-bound proteins were detected using Amersham's ECL chemiluminescence kit. To confirm equal protein loading, blots were reprobed with a β-actin antibody (1:5000 dilution). Western blot images were captured with a Kodak 2000 mM imaging system and data were analyzed using 1D Kodak imaging analysis software.

Locomotor Activity.

Behavioral data were collected using VersaMax Animal Activity Monitors (AccuScan Model RXYZCM-16, Columbus, Ohio). Each chamber was 40×40×30.5 cm$^3$, made of clear Plexiglas and covered with a Plexiglas lid with air-holes. Infrared monitoring sensors were located every 2.54 cm along the perimeter (16 infrared beams along each side) and 2.5 cm above the floor. Two additional sets of 16 sensors were located 8.0 cm above the floor on opposite sides. Data were collected and analyzed by a VersaMax Analyzer (AccuScan Model CDA-8, Columbus, Ohio) which in turn sent information to an IBM computer where it was stored for future analyses. Locomotor activity was presented as horizontal movement and vertical movement. All data are expressed as percent of the vehicle-treated control group (mean 6 SEM) and were obtained 1 day after MPTP or vehicle treatment in a 20-min test session.

Data Analysis.

Data analysis was performed using Prism 4.0 software (GraphPad Software, San Diego, Calif.). Data were first analyzed using one-way ANOVA and then Bonferroni's post-test was performed to compare all treatment groups, and differences with $p<0.05$ were considered significant.

Results

Rottlerin Rescues MPP$^+$-Induced TH$^+$ Neuronal Loss in Primary Mesencephalic Cultures.

Figure 2:
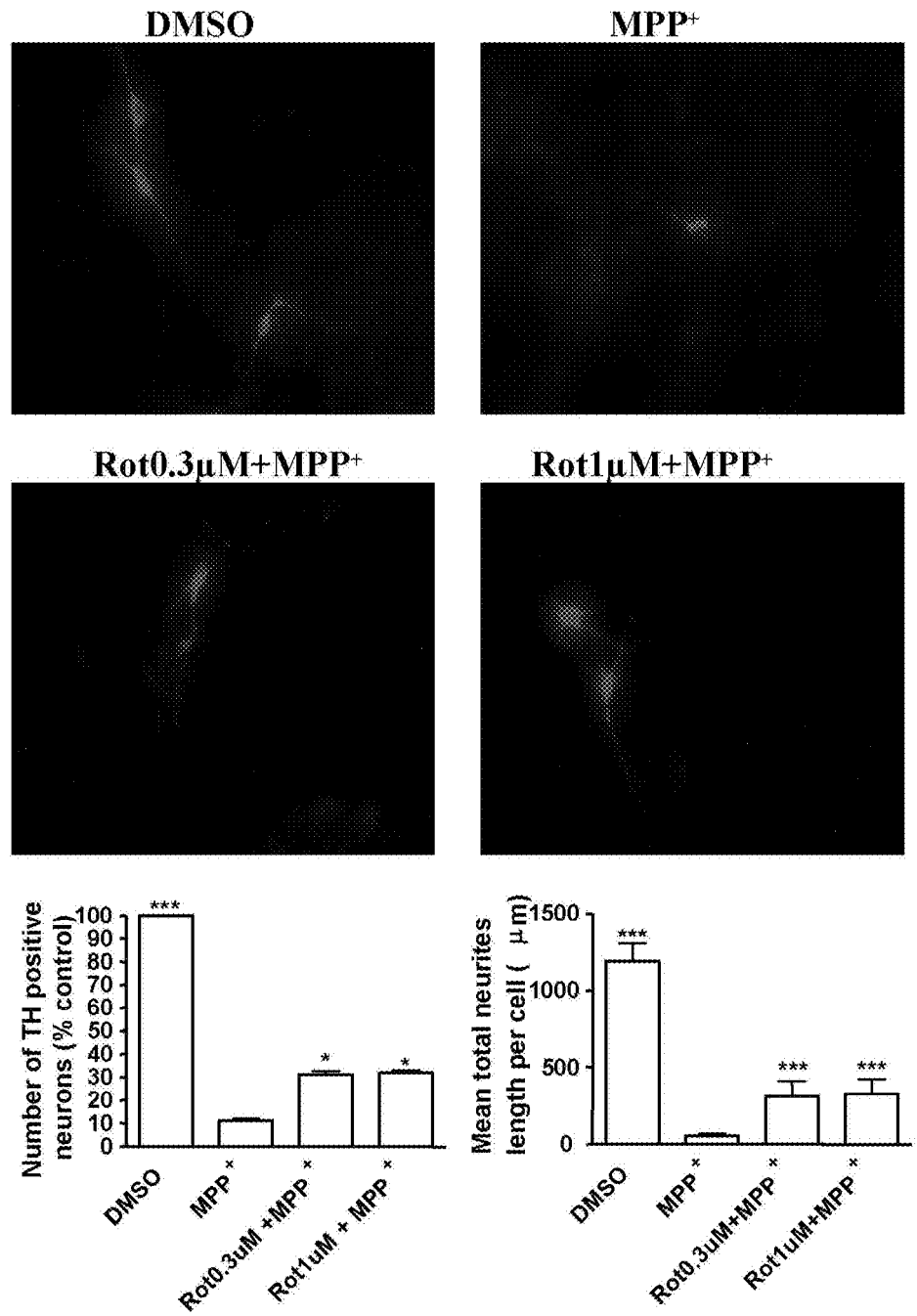
FIG. 2. Rottlerin protects against $MPP^+$ induced dopaminergic degeneration in mice mide brain Primary cultures. Effects of rottlerin on the number of tyrosine hydroxylase positive cells and their neurites length in $MPP^+$ treated mesencephalic primary culture. Primary neurons were cultured and grown on laminin coated cover slips. The cultures were then exposed to 10 µM MPP+ for 48 hr in the presence or absence of 0.3 µM-1 µM rottlerin. After treatment primary neurons were fixed and immunostained for TH and viewed under a Nikon TE2000 fluorescence microscope as described in the methods section. TH cell count and neuronal process length were quantified using Metamorph image analysis software as described in the methods section. Each group contains 4 samples from 2 separate experiments. Asterisks ($*p<0.05$ and $***p<0.001$) indicate significant difference compared with MPP+ treated neurons.

Rottlerin was originally reported to be able to compete for the ATP-binding site and inhibit PKCδ kinase activity (Gschwendt, Muller et al. 1994). This inhibitor has been used to implicate PKCδ in a variety of cellular events, including apoptosis (Chen, Ma et al. 1999; Reyland, Anderson et al. 1999; Dempsey, Newton et al. 2000; Way, Chou et al. 2000; Basu, Woolard et al. 2001; Vancurova, Miskolci et al. 2001). Previous studies in our lab have shown the direct inhibition of PKCδ by rottlerin in vitro kinase assays (Anantharam, Kitazawa et al. 2002). Preliminary investigations of the neuroprotective effect of rottlerin were performed in a standardized procedure where MPP$^+$ induced apoptotic injury. Primary mesencephalic dopaminergic neuronal cells were exposed to 10 μM MPP$^+$ in the presence or absence of rottlerin (0.3 and 1 μM) for 48 hrs. Then cells were fixed and stained for TH. The number of TH+ cells as well as their neurite length was quantified. As shown in FIG. 2, MPP$^+$ produced 90% cell death and loss of neurites length. Both 0.3 μM and 1 μM rottlerin significantly blocked MPP+-induced degeneration of TH+ neurons and their processes in primary nigral dopaminergic neurons. Collectively, these results clearly demonstrate the neuroprotective effect of rottlerin in dopaminergic neurodegenerative models.

Rottlerin Inhibits Protein Kinase C-δ Activity in Mice Substantia Nigra.

Figure 3:
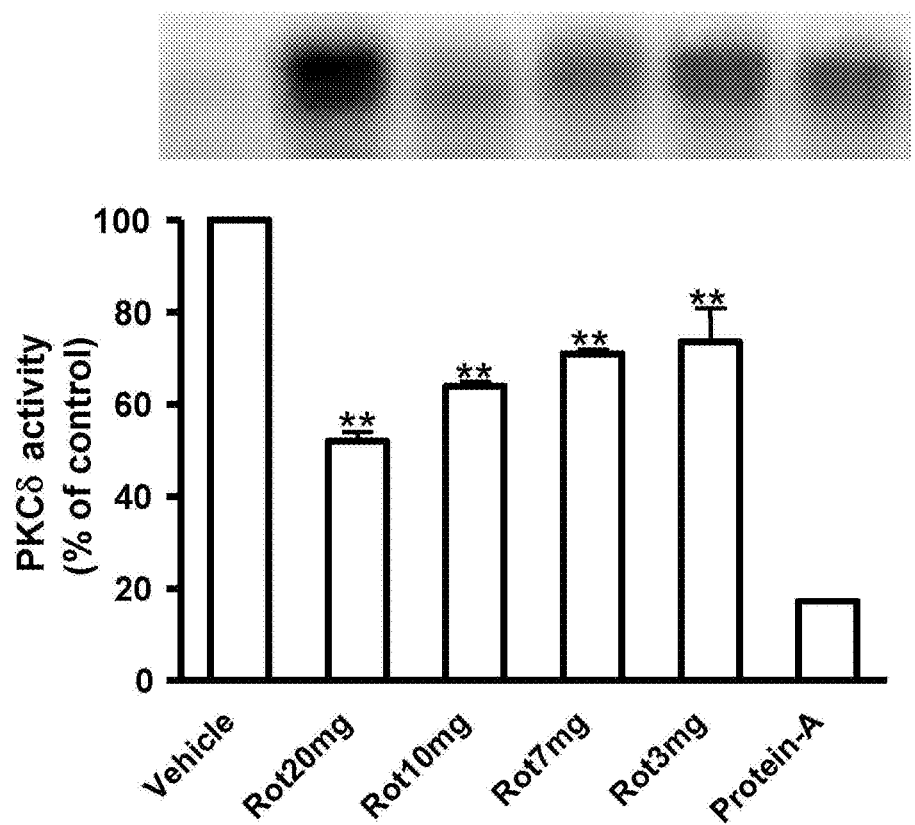
FIG. 3. Rottlerin treatment suppress PKCδ kinase activity in mice SN. Effects of rottlerin on PKCδ kinase activity in mice substantia nigra. C57 black mice were treated with different doses (3-20 mg/kg) rottlerin for 5 days. Substantia nigra tissue will be homogenized and used for immunoprecipitation kinase assay as described in Materials and Methods. The bands were quantified by a PhosphoImager after scanning the dried gel and expressed as a percentage of control (untreated cells). The data represent an average of two individual measurements from two separate experiments±SEM. Asterisks ($**p<0.01$) indicate significant differences compared with control.

To determine the inhibitory potency of rottlerin on PKCδ activity in animal model, we tested various doses of rottlerin on PKCδ enzyme activity in mice substantia nigra (SN) by using an in vitro kinase assay. PKCδ was immunoprecipitated from SN lysates of both rottlerin-mice and vehicle-mice using PKCδ specific polyclonal antibody and incubated with histone $H_1$ and [$^{32}$P] ATP. The enzymatic activity of PKCδ decreased significantly in SN of rottlerin-mice compared with vehicle-mice (FIG. 3). Densitometric analysis of phosphorylated histone $H_1$ bands revealed a 50% and 40% decrease in protein kinase activity in SN of mice orally treated with 20 mg and 10 mg rottlerin respectively, and i.p. injection with 7 mg or 3 mg rottlerin resulted in more than 30% reduction in the kinase activity in mice SN of mice.

Rottlerin Attenuates Striatal Dopamine Depletion Induced by MPTP-Treatment.

Figure 4:
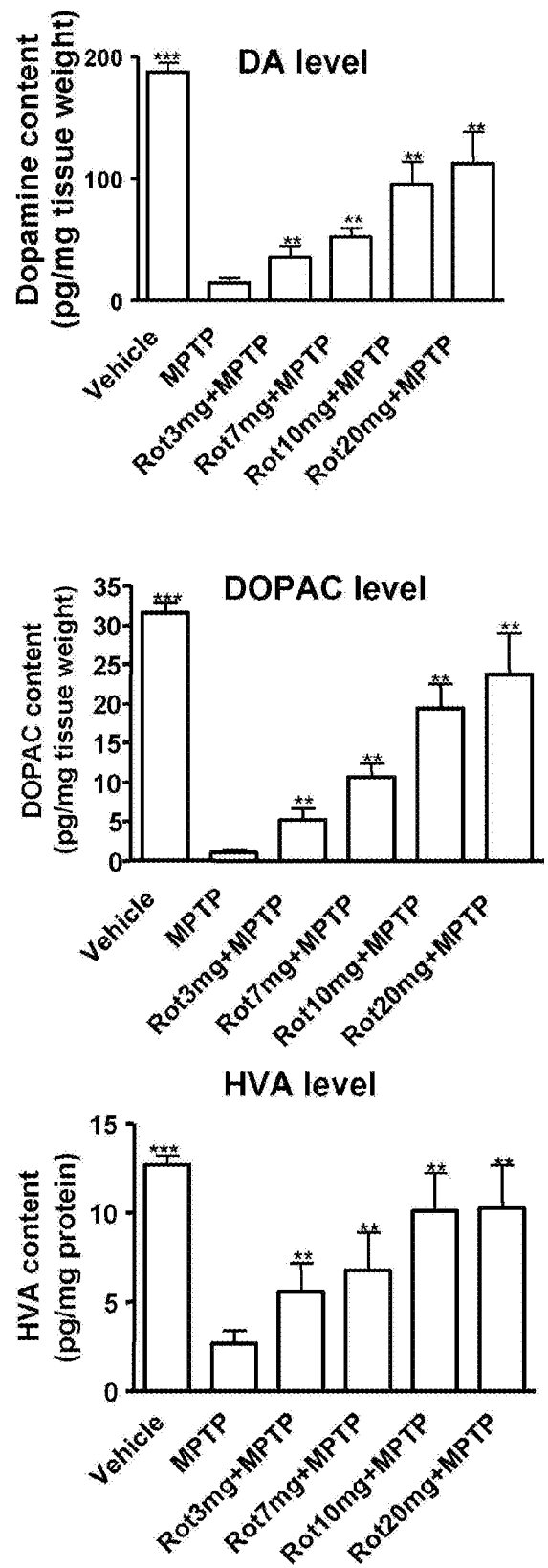
FIG. 4. Rottlerin protects against MPTP induced depletion of striatal dopamine. Effects of different doses of rottlerin (3-20 mg/kg) on MPTP (30 mg/kg) induced depletions of dopamine, DOPAC, and HVA. 1% DMSO was used as vehicle control. Asterisks ($P<0.01$ and $*P<0.001$) indicate significant difference compared with MPTP group, more than 6 animals per group.

In the present study, we examined whether administration of the PKCδ inhibitor rottlerin could block MPTP-induced dopamine and its metabolites loss in mice striatum. 30 mg/kg MPTP treatment for 5 days resulted in significantly dopamine loss in mice brain. Vehicle-treated animals had 187.5±7.413 pg DA/mg tissue weight in the striatum, which was reduced by −94% to 14.49±3.77 pg DA/mg tissue weight in MPTP-treated animals (FIG. 4). Oral dose rottlerin (20 mg/kg) and i.p. doses rottlerin (3, 7 and 10 mg/kg) significantly antagonized the MPTP-induced decrease in dopamine and metabolite levels in a dose-dependent manner (FIG. 4). Especially 20 mg/kg rottlerin afforded a 50% protection against dopamine loss induced by MPTP toxicity in striatum. The dopamine level in rottlerin 20 mg/kg+MPTP mice was 112.8±25.32 pg/mg tissue weight compared with vehicle-treated animals which was 187.5±7.413 pg DA/mg tissue weight and MPTP-mice which was 14.49±3.77 pg DA/mg tissue weight. The dopamine metabolites DOPAC and HVA showed similar patterns to dopamine.

Rottlerin Restricts MPTP-Induced Cell Loss in SNpc.

Figure 5:
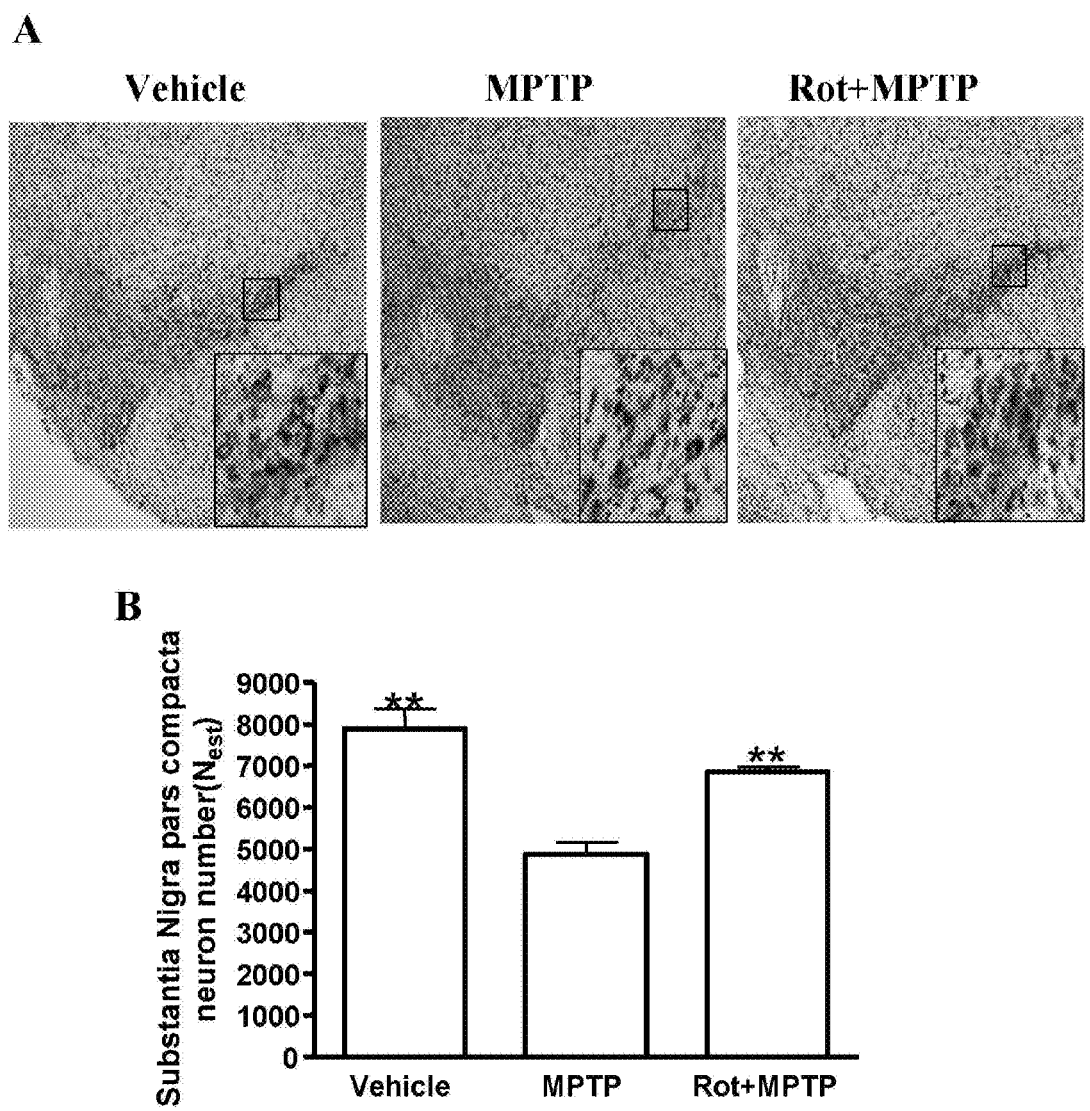
FIG. 5A. Number and Morphology changes of SNpc neurons and terminals in MPTP mice brain.
FIG. 5B. Total numbers of $TH^+$ neurons in the substantia nigra pars compacta in groups exposed to vehicle (1% DMSO), 30 mg/kg MPTP or the combination with rottlerin (20 mg/kg) were counted and showed in the figure. $TH^+$ neurons were measured using unbiased stereology two days after the last treatment. Asterisks ($**P<0.01$) indicate significant difference compared with MPTP group, n=3 per group.

The protective property of rottlerin against MPTP toxicity was confirmed by preservation of TH-immunoreactive neurons in the substantia nigra pars compacta (SNpc). Immunohistochemistical analysis of tyrosine hydroxylase (TH), the phenotypic marker for dopaminergic neurons, indicated dopaminergic degeneration in the SNpc. The administration of MPTP, 30 mg/kg for 5 continuous days, caused 40% cell loss in SNpc as compared to controls, whereas cotreatment with 20 mg/kg rottlerin showed 13% cell loss (FIG. 5), achieving a 37% protective effect, which is closed to its 50% protection effect against striatal dopamine depletion.

Rottlerin Prevents MPTP-Induced Reduction of TH Protein Level in SN.

Figure 6:
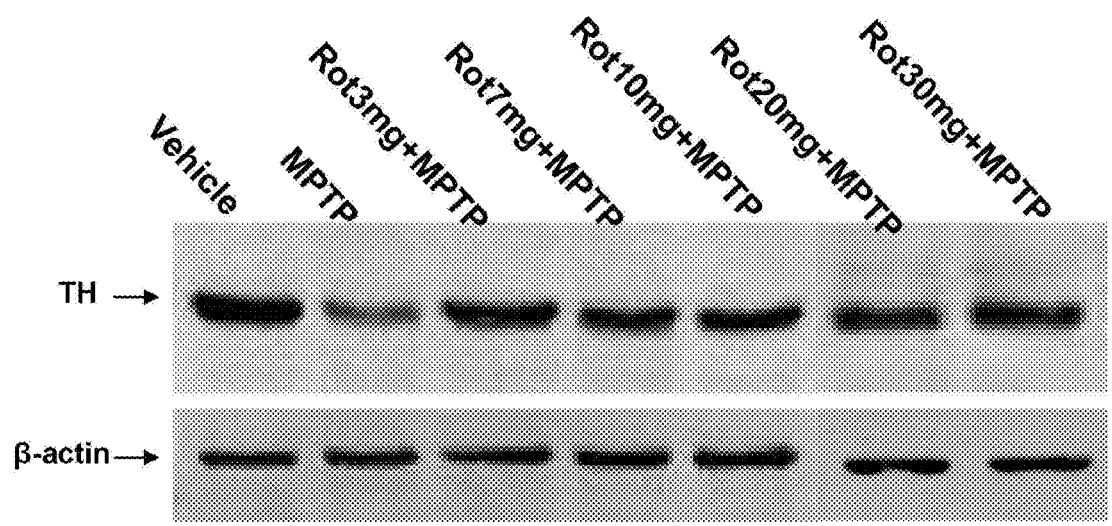
FIG. 6. Effect of Rottlerin on TH expression level in SN of MPTP treated mice. Effect of different doses of rottlerin on TH expression level in SN of MPTP treated mice. C57 black mice were treated with different doses (3-30 mg/kg) rottlerin or MPTP (30 mg/kg) continuously for 5 days. 1% DMSO served as vehicle control. Substantia nigra tissue will be homogenized and used for western blot as described in Materials and Methods. Tyrosine hydroxylase expression was detected using monoclonal antibody raised against TH. The membrane was reprobed with β-actin antibody to confirm equal protein loading in each lane.

MPTP-induced loss of TH$^+$ cells in the SN would be expected to be accompanied by loss of TH protein in this region. Conversely, preservation of such cells by rottlerin should be accompanied by preservation of TH protein level in SN. FIG. 6 demonstrates that MPTP greatly reduced TH protein level in mice SN which maybe because of loss of TH$^+$ neurons in this region. All doses of rottlerin attenuate loss of TH protein caused by MPTP toxicity (FIG. 6).

Rottlerin Protects Against MPTP-Induced Motor Deficits.

Figure 7:
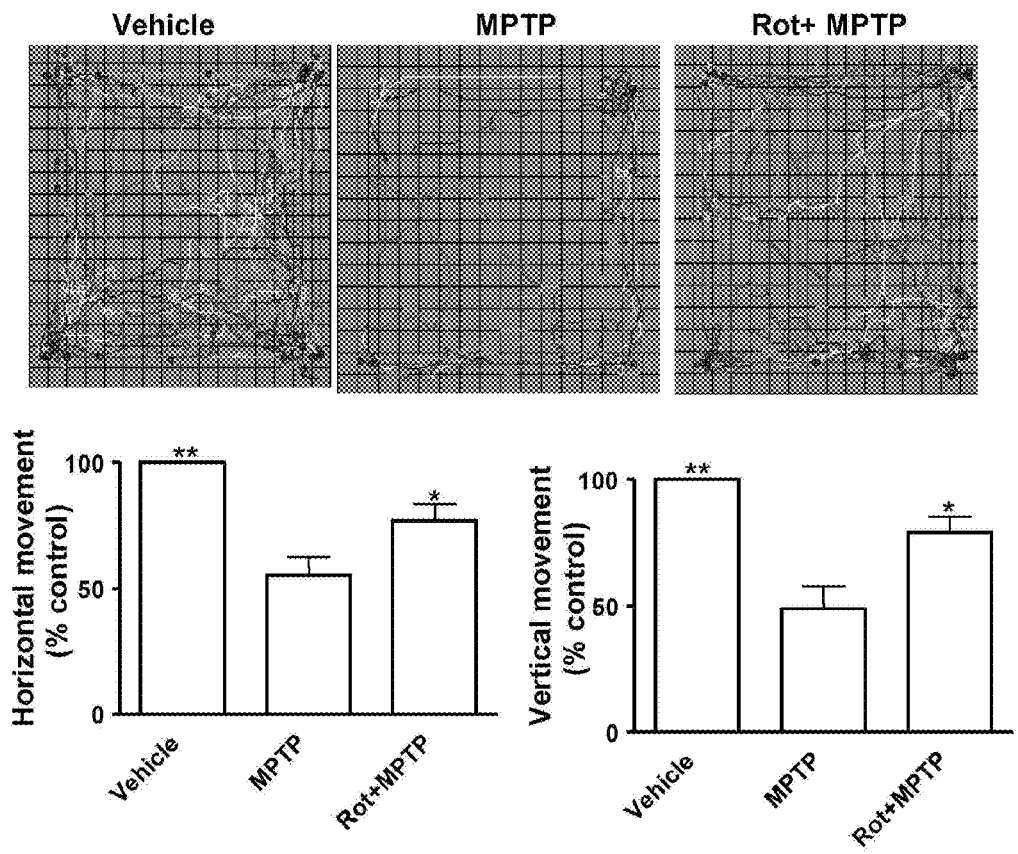
FIG. 7. Rottlerin protects against MPTP-induced motor deficits. Effects of rottlerin on MPTP-induced alterations in locomotor activity. Mice were co-treated rottlerin (20 mg/kg) with MPTP (30 mg/kg) for 5 days. Locomotor activity was measured one day after last injection by using VersaMax Analyzer. The vehicle (1% DMSO)-treated group served as control and was set at 100%. Asterisks ($*P<0.05$ and $**P<0.01$) indicate significant difference compared with MPTP group, n=6 per group.

Locomotor activity was presented as horizontal movement and vertical movement. All data are expressed as percent of the vehicle-treated control group (mean 6 SEM) and were obtained 1 day after MPTP or vehicle treatment in a 20-min test session. MPTP treatment alone led to a reduction of locomotor activity to a level of 55.17% compared to values of the control group. The injection of rottlerin (20, mg/kg) significantly attenuated the MPTP-induced decrease of the horizontal movement and vertical movement to levels of 76.93% and 79%, respectively (FIG. 7).

Discussion

In the present study, we have demonstrated that a widely used, selective PKCδ inhibitor rottlerin provided neuroprotective actions in rodent models of Parkinson's disease. The compound provided effective functional and histological protection of dopaminergic neurons after high dose MPTP chronic treatment.

Rottlerin is a compound extracted from Mallotus philippinensis, it's shown that this compound is able to inhibit protein kinases specific for PKC delta isoform. The inhibition effects of PKCδ mainly due to a competition for the ATP binding. PKCδ, a key member of the novel PKC family, is a redox sensitive kinase in various cell types important in cell differentiation, proliferation and secretion. Our recent studies demonstrate that PKCδ is an oxidative stress sensitive kinase, and activation of this kinase via capase-3 dependent proteolysis induces apoptotic cell death in cell culture models of PD (Kaul, Kanthasamy et al. 2003; Latchoumycandane, Anantharam et al. 2005). Although it's not clear that the events downstream of PKCδ and those that lead to apoptosis, recent studies from many research groups have shown that catalytically active PKCδ fragment can regulate the activity of a host of cell signaling molecules such as scrambalase (Frasch, Henson et al. 2000), DNA protein kinase which is a DNA repair enzyme (Bharti, Kraeft et al. 1998), heat-shock proteins-25/27 (Maizels, Peters et al. 1998), histone $H_2B$ (Ajiro 2000), and lamin kinase (Cross, Griffiths et al. 2000). PKCδ also is able to phosphorylate other signaling molecules such as MAP kinases (Chen, Ma et al. 1999), Jak2, a tyrosine kinase (Kovanen, Junttila et al. 2000), and signal transducers and activators of transcription such as Stat3 (Jain, Zhang et al. 1999). Most recently studies also showed that PKCδ can activate NF-κB, and thereby promotes apoptosis in neutrophils (Vancurova, Miskolci et al. 2001). Furthermore, PKCδ has been shown to translocate to cytosol and a variety of cellular organelles to initiate apoptosis (Sawai, Okazaki et al. 1997; Chen, Ma et al. 1999; Li, Zhang et al. 1999; Dempsey, Newton et al. 2000; Majumder, Pandey et al. 2000). Hence, constitutively active PKCδ can promote loss of cellular regulatory function in many of its substrates, resulting in rapid apoptosis. Initially, rottlerin was reported to inhibit PKCδ (IC50=3-6 μM) 5- to 10-fold more potently than PKCα or PKCβ and 13- to 33-fold more potently than PKCε, ζ, or η. It also inhibited CAM kinase III at 3-6 μM, was inactive against SRC kinase, and was a weak inhibitor of PKA and casein kinase II (Gschwendt, Muller et al. 1994). It was later used widely as a selective inhibitor for nPKCδ, both in vitro and in studies of intact cells (Clark, West et al. 2003). Previously published papers have shown direct inhibition of PKCδ by rottlerin in vitro kinase assays (Gschwendt, Muller et al. 1994; Way, Chou et al. 2000; Vancurova, Miskolci et al. 2001). Pretreatment with rottlerin successful prevented MMT induced accumulation of PKCδ cleavage product and increased kinase activity in a dose-dependent manner in PC12 dopaminergic cells (Anantharam, Kitazawa et al. 2002). It has previously been reported that selective inhibitors of PKCδ inhibitor rottlerin inhibited TPA-induced dephosphorylation of Akt which protects keratinocytes from the toxic effects of ultraviolet light (Li, Sampat et al. 2006). And Src tyrosine kinase inhibitor genistein and the p60$^{Src}$ tyrosine-specific kinase inhibitor which can inhibit the phosphorylation of PKCδ by tyrosine kinase inhibition dramatically inhibited $H_2O_2$ and the Parkinsonian toxin 1-methyl-4-phenylpyridinium-induced PKCδ cleavage, kinase activation, and apoptotic cell death in dopaminergic N27 cells (Kaul, Anantharam et al. 2005). We were therefore confident that we were evaluating a potent PKCδ inhibitor in our Parkinson's disease studies. In the present studies, we have used well-established models with MPTP that produce cell loss and permanent dopamine depletion in vivo (Bezard, Stutzmann et al. 1998; Riederer, Foley et al. 2002; O'Neill, Murray et al. 2004). We first test effect of rottlerin on MPP$^+$ induced cell death in primary mesencephalic cultures. Both 0.3 μM and 1 μM rottlerin significantly blocked MPP$^+$-induced degeneration of TH$^+$ neurons and their processes in primary nigral dopaminergic neurons, which indicates the neuroprotective effects of rottlerin. We also administrated mice with MPTP at a 30 mg/kg dose daily for 5 days, which was shown to induce cell death by apoptosis as assessed by terminal deoxynucleotidyl transferase labeling (TUNEL), and acridine orange to visualize clumped chromatin (Tatton and Kish 1997). Following administration of MPTP, there is evidence for apoptotic cell death as well as activation of caspase-9, caspase-3, caspase-8, and Bid cleavage (Tatton and Kish 1997; Hartmann, Hunot et al. 2000; Turmel, Hartmann et al. 2001; Viswanath, Wu et al. 2001). In the brain, MPTP is metabolized to its active form MPP$^+$ (1-methyl-4-phenylpyridinium ion), accumulates in dopaminergic neurons, and subsequently inhibits complex I in the mitochondrial respiratory chain (Fritz, Abell et al. 1985; Singer, Ramsay et al. 1988; Marini, Schwartz et al. 1989). We demonstrated that MPP$^+$-induced oxidative stress proteolytically activates PKCδ in a caspase-3-dependent manner to induce apoptosis and up-regulate the caspase cascade in dopaminergic neuronal cells. With the co-treatment of MPTP with different doses of rottlerin for 5 days, there was a significant protection against loss of dopamine in striatum and TH immunoreactive neurons in the SNpc. The MPTP-induced decrease of locomotor activity also was attenuated by rottlerin.

Pretreatment of macrophages with rottlerin suppresses UV-B-induced DNA fragmentation in macrophages by approximately 30% at (1 μM) and by almost 50% at (10 μM). Addition rottlerin to zinc deficient medium reduced or eliminated proteolysis of PKC-delta, activated caspase-3 and restored cell number in 3T3 cells (Chou, Clegg et al. 2004). Asbestos-induced apoptosis also was inhibited in cells stably expressing a dominant-negative kinase-deficient mutant of PKCδ and PKCδ inhibitor rottlerin (Shukla, Stern et al. 2003). Rottlerin reduced silica-induced apoptosis in bone marrow-derived macrophages as measured by DNA fragmentation, and in NZM mice, in vivo treatment with rottlerin significantly decreased the exacerbation of autoimmunity by silica exposure (Brown, Schwanke et al. 2005). Glutamate-induced cell death was significantly recovered when cells were transfected with siRNA against PKCδ, suggesting that PKCδ plays an important role in the regulation of cell death in glutamate-treated cells (Choi, Hur et al. 2006). But here were very fewer studies about protective effect of PKCδ inhibition in dopaminergic cells or MPTP models. Major insights into the neurodegenerative PD process have been gained from the MPTP-induced models that replicate the salient Parkinsonian symptoms and pathology (Langston 1998; Betarbet, Sherer et al. 2002; McCormack, Thiruchelvam et al. 2002). Recent studies have shown that MPTP or its active metabolite MPP$^+$ induces many apoptotic events including ROS generation, cytochrome c release, caspase activation, and DNA fragmentation (Viswanath, Wu et al. 2001; Sherer, Betarbet et al. 2002; Kaul, Kanthasamy et al. 2003). In addition, alterations in certain apoptotic cell death-related molecules such as Bcl-2, MAP kinases, and PARP (Choi, Canzoniero et al. 1999; Mandir, Przedborski et al. 1999; Hartmann, Hunot et al. 2000) during MPP$^+$-induced dopaminergic degeneration have also been reported. Recently, we demonstrated that caspase-3-dependent proteolytic activation of PKCδ mediates and regulates oxidative stress-induced apoptotic cell death during exposure to various dopaminergic neurotoxins including MPP$^+$ (Anantharam, Kitazawa et al. 2002; Kaul, Kanthasamy et al. 2003; Kitazawa, Anantharam et al. 2003).

PKCδ activation may therefore play a critical role in the pathogenesis of neurodegenerative diseases. Our present findings show that rottlerin is neuroprotective in MPTP models of PD and that it blocks activation of PKCδ activation. In summary, rottlerin appears to be a novel systemically active PKC-delta isoform inhibitor, which has the potential to exert therapeutic effects in neurodegenerative diseases.

REFERENCES

Adachi, M., O. Sohma, et al. (2001). "Combination effect of systemic hypothermia and caspase inhibitor administration against hypoxic-ischemic brain damage in neonatal rats." *Pediatr Res* 50(5): 590-5.

Ajiro, K. (2000). "Histone H2B phosphorylation in mammalian apoptotic cells. An association with DNA fragmentation." *J Biol Chem* 275(1): 439-43.

Alzheimer, C. and S. Werner (2002). "Fibroblast growth factors and neuroprotection." *Adv Exp Med Biol* 513: 335-51.

Anantharam, V., M. Kitazawa, et al. (2002). "Caspase-3-dependent proteolytic cleavage of protein kinase Cdelta is essential for oxidative stress-mediated dopaminergic cell death after exposure to methylcyclopentadienyl manganese tricarbonyl." *J Neurosci* 22(5): 1738-51.

Basu, A., M. D. Woolard, et al. (2001). "Involvement of protein kinase C-delta in DNA damage-induced apoptosis." *Cell Death Differ* 8(9): 899-908.

Betarbet, R., T. B. Sherer, et al. (2002). "Animal models of Parkinson's disease." *Bioessays* 24(4): 308-18.

Bezard, E., J. M. Stutzmann, et al. (1998). "Riluzole delayed appearance of parkinsonian motor abnormalities in a chronic MPTP monkey model." *Eur J Pharmacol* 356(2-3): 101-4.

Bharti, A., S. K. Kraeft, et al. (1998). "Inactivation of DNA-dependent protein kinase by protein kinase Cdelta: implications for apoptosis." *Mol Cell Biol* 18(11): 6719-28.

Brown, J. M., C. M. Schwanke, et al. (2005). "Effects of rottlerin on silica-exacerbated systemic autoimmune disease in New Zealand mixed mice." *Am J Physiol Lung Cell Mol Physiol* 289(6): L990-8.

Chen, N., W. Ma, et al. (1999). "Translocation of protein kinase Cepsilon and protein kinase Cdelta to membrane is required for ultraviolet B-induced activation of mitogen-activated protein kinases and apoptosis." *J Biol Chem* 274(22): 15389-94.

Choi, B. H., E. M. Hur, et al. (2006). "Protein kinase C{delta}-mediated proteasomal degradation of MAP kinase phosphatase-1 contributes to glutamate-induced neuronal cell death." *J Cell Sci* 119(Pt 7): 1329-40.

Choi, W. S., L. M. Canzoniero, et al. (1999). "Characterization of MPP(+)-induced cell death in a dopaminergic neuronal cell line: role of macromolecule synthesis, cytosolic calcium, caspase, and Bcl-2-related proteins." *Exp Neurol* 159(1): 274-82.

Chou, S. S., M. S. Clegg, et al. (2004). "Alterations in protein kinase C activity and processing during zinc-deficiency-induced cell death." *Biochem J* 383(Pt 1): 63-71.

Clark, A. S., K. A. West, et al. (2003). "Altered protein kinase C (PKC) isoforms in non-small cell lung cancer cells: PKCdelta promotes cellular survival and chemotherapeutic resistance." *Cancer Res* 63(4): 780-6.

Cross, T., G. Griffiths, et al. (2000). "PKC-delta is an apoptotic lamin kinase." *Oncogene* 19(19): 2331-7.

Dempsey, E. C., A. C. Newton, et al. (2000). "Protein kinase C isozymes and the regulation of diverse cell responses." *Am J Physiol Lung Cell Mol Physiol* 279(3): L429-38.

Denning, M. F., A. A. Dlugosz, et al. (2000). "Cross-talk between epidermal growth factor receptor and protein kinase C during calcium-induced differentiation of keratinocytes." *Exp Dermatol* 9(3): 192-9.

Frasch, S. C., P. M. Henson, et al. (2000). "Regulation of phospholipid scramblase activity during apoptosis and cell activation by protein kinase Cdelta." *J Biol Chem* 275(30): 23065-73.

Friedlander, R. M. (2003). "Apoptosis and caspases in neurodegenerative diseases." *N Engl Med* 348(14): 1365-75.

Fritz, R. R., C. W. Abell, et al. (1985). "Metabolism of the neurotoxin in MPTP by human liver monoamine oxidase B." *FEBS Lett* 186(2): 224-8.

Garnier, M., D. Di Lorenzo, et al. (1997). "Identification of estrogen-responsive genes in neuroblastoma SK-ER3 cells." *J Neurosci* 17(12): 4591-9.

Gollapudi, L. and M. M. Oblinger (1999). "Stable transfection of PC12 cells with estrogen receptor (ERalpha): protective effects of estrogen on cell survival after serum deprivation." *J Neurosci Res* 56(1): 99-108.

Gschwendt, M., H. J. Muller, et al. (1994). "Rottlerin, a novel protein kinase inhibitor." *Biochem Biophys Res Commun* 199(1): 93-8.

Hartmann, A. and E. C. Hirsch (2001). "Parkinson's disease. The apoptosis hypothesis revisited." *Adv Neurol* 86: 143-53.

Hartmann, A., S. Hunot, et al. (2000). "Caspase-3: A vulnerability factor and final effector in apoptotic death of dopaminergic neurons in Parkinson's disease." *Proc Natl Acad Sci USA* 97(6): 2875-80.

Jain, N., T. Zhang, et al. (1999). "Protein kinase C delta associates with and phosphorylates Stat3 in an interleukin-6-dependent manner." *J Biol Chem* 274(34): 24392-400.

Jellinger, K. A. (2000). "Cell death mechanisms in Parkinson's disease." *J Neural Transm* 107(1): 1-29.

Kajta, M., W. Lason, et al. (2004). "Effects of estrone on N-methyl-D-aspartic acid- and staurosporine-induced changes in caspase-3-like protease activity and lactate dehydrogenase-release: time- and tissue-dependent effects in neuronal primary cultures." *Neuroscience* 123(2): 515-26.

Kaul, S., V. Anantharam, et al. (2005). "Tyrosine phosphorylation regulates the proteolytic activation of protein kinase Cdelta in dopaminergic neuronal cells." *J Biol Chem* 280(31): 28721-30.

Kaul, S., A. Kanthasamy, et al. (2003). "Caspase-3 dependent proteolytic activation of protein kinase C delta mediates and regulates 1-methyl-4-phenylpyridinium (MPP+)-induced apoptotic cell death in dopaminergic cells: relevance to oxidative stress in dopaminergic degeneration." *Eur J Neurosci* 18(6): 1387-401.

Kitazawa, M., V. Anantharam, et al. (2001). "Dieldrin-induced oxidative stress and neurochemical changes contribute to apoptopic cell death in dopaminergic cells." *Free Radic Biol Med* 31(11): 1473-85.

Kitazawa, M., V. Anantharam, et al. (2003). "Dieldrin induces apoptosis by promoting caspase-3-dependent proteolytic cleavage of protein kinase Cdelta in dopaminergic cells: relevance to oxidative stress and dopaminergic degeneration." *Neuroscience* 119(4): 945-64.

Kovanen, P. E., I. Junttila, et al. (2000). "Regulation of Jak2 tyrosine kinase by protein kinase C during macrophage differentiation of IL-3-dependent myeloid progenitor cells." *Blood* 95(5): 1626-32.

Langston, J. W. (1998). "Epidemiology versus genetics in Parkinson's disease: progress in resolving an age-old debate." *Ann Neurol* 44(3 Suppl 1): S45-52.

Latchoumycandane, C., V. Anantharam, et al. (2005). "Protein kinase Cdelta is a key downstream mediator of manganese-induced apoptosis in dopaminergic neuronal cells." *J Pharmacol Exp Ther* 313(1): 46-55.

Li, L., K. Sampat, et al. (2006). "Protein kinase C negatively regulates Akt activity and modifies UVC-induced apoptosis in mouse keratinocytes." *J Biol Chem* 281(6): 3237-43.

Li, W., J. Zhang, et al. (1999). "Protein kinase C-alpha overexpression stimulates Akt activity and suppresses apoptosis induced by interleukin 3 withdrawal." *Oncogene* 18(47): 6564-72.

Maizels, E. T., C. A. Peters, et al. (1998). "Heat-shock protein-25/27 phosphorylation by the delta isoform of protein kinase C." *Biochem J* 332 (Pt 3): 703-12.

Majumder, P. K., P. Pandey, et al. (2000). "Mitochondrial translocation of protein kinase C delta in phorbol ester-induced cytochrome c release and apoptosis." *J Biol Chem* 275(29): 21793-6.

Mandir, A. S., S. Przedborski, et al. (1999). "Poly(ADP-ribose) polymerase activation mediates 1-methyl-4-phenyl-1,2,3,6-tetrahydropyridine (MPTP)-induced parkinsonism." *Proc Natl Acad Sci USA* 96(10): 5774-9.

Marini, A. M., J. P. Schwartz, et al. (1989). "The neurotoxicity of 1-methyl-4-phenylpyridinium in cultured cerebellar granule cells." *J Neurosci* 9(10): 3665-72.

McCormack, A. L., M. Thiruchelvam, et al. (2002). "Environmental risk factors and Parkinson's disease: selective degeneration of nigral dopaminergic neurons caused by the herbicide paraquat." *Neurobiol Dis* 10(2): 119-27.

O'Neill, M. J., T. K. Murray, et al. (2004). "Neurotrophic actions of the novel AMPA receptor potentiator, LY404187, in rodent models of Parkinson's disease." *Eur J Pharmacol* 486(2): 163-74.

Przedborski, S. and V. Jackson-Lewis (1998). "Mechanisms of MPTP toxicity." *Mov Disord* 13(Suppl 1): 35-8.

Reyland, M. E., S. M. Anderson, et al. (1999). "Protein kinase C delta is essential for etoposide-induced apoptosis in salivary gland acinar cells." *J Biol Chem* 274(27): 19115-23.

Riederer, P., P. Foley, et al. (2002). "Biochemical and pharmacological characterization of 1-trichloromethyl-1,2,3,4-tetrahydro-beta-carboline: a biologically relevant neurotoxin?" *Eur J Pharmacol* 442(1-2): 1-16.

Sawai, H., T. Okazaki, et al. (1997). "Ceramide-induced translocation of protein kinase C-delta and -epsilon to the cytosol. Implications in apoptosis." *J Biol Chem* 272(4): 2452-8.

Sherer, T. B., R. Betarbet, et al. (2002). "An in vitro model of Parkinson's disease: linking mitochondrial impairment to altered alpha-synuclein metabolism and oxidative damage." *J Neurosci* 22(16): 7006-15.

Shukla, A., M. Stern, et al. (2003). "Asbestos-induced apoptosis is protein kinase C delta-dependent." *Am J Respir Cell Mol Biol* 29(2): 198-205.

Singer, T. P., R. R. Ramsay, et al. (1988). "Mechanism of the neurotoxicity of 1-methyl-4-phenylpyridinium (MPP+), the toxic bioactivation product of 1-methyl-4-phenyl-1,2,3,6-tetrahydropyridine (MPTP)." *Toxicology* 49(1): 17-23.

Tatton, N. A. and S. J. Kish (1997). "In situ detection of apoptotic nuclei in the substantia nigra compacta of 1-methyl-4-phenyl-1,2,3,6-tetrahydropyridine-treated mice using terminal deoxynucleotidyl transferase labelling and acridine orange staining." *Neuroscience* 77(4): 1037-48.

Tatton, W. G., R. Chalmers-Redman, et al. (2003). "Apoptosis in Parkinson's disease: signals for neuronal degradation." *Ann Neurol* 53 Suppl 3: S61-70; discussion S70-2.

Thiruchelvam, M., A. McCormack, et al. (2003). "Age-related irreversible progressive nigrostriatal dopaminergic neurotoxicity in the paraquat and maneb model of the Parkinson's disease phenotype." *Eur J Neurosci* 18(3): 589-600.

Thiruchelvam, M. J., J. M. Powers, et al. (2004). "Risk factors for dopaminergic neuron loss in human alpha-synuclein transgenic mice." *Eur J Neurosci* 19(4): 845-54.

Turmel, H., A. Hartmann, et al. (2001). "Caspase-3 activation in 1-methyl-4-phenyl-1,2,3,6-tetrahydropyridine (MPTP)-treated mice." *Mov Disord* 16(2): 185-9.

Vancurova, I., V. Miskolci, et al. (2001). "NF-kappa B activation in tumor necrosis factor alpha-stimulated neutrophils is mediated by protein kinase Cdelta. Correlation to nuclear Ikappa Balpha." *J Biol Chem* 276(23): 19746-52.

Viswanath, V., Y. Wu, et al. (2001). "Caspase-9 activation results in downstream caspase-8 activation and bid cleavage in 1-methyl-4-phenyl-1,2,3,6-tetrahydropyridine-induced Parkinson's disease." *J Neurosci* 21(24): 9519-28.

Way, K. J., E. Chou, et al. (2000). "Identification of PKC-isoform-specific biological actions using pharmacological approaches." *Trends Pharmacol Sci* 21(5): 181-7.

Yang, Y., S. Kaul, et al. (2004). "Suppression of Caspase-3-dependent proteolytic activation of protein kinase C-delta by small interfering RNA prevents MPP+-induced dopaminergic degeneration." *Molecular and Cellular Neuroscience* 25(3): 406-421.

Example 2

Protein Kinase C Delta Negatively Regulates Tyrosine Hydroxylase Activity and Dopamine Synthesis by Enhancing Protein Phosphatase-2A Activity in Dopaminergic Neurons Tyrosine hydroxylase (TH), the rate-limiting enzyme in dopamine synthesis, can be regulated by phosphorylation at multiple serine residues including serine 31 and serine 40. In the present study, we report a novel interaction between a key member of the novel PKC family, PKC-delta (PKCδ), and TH, in which the kinase modulates dopamine synthesis by negatively regulating TH activity via protein phosphatase 2A (PP2A). We observed that PKCδ is highly expressed in nigral dopaminergic neurons and co-localizes with TH. Interestingly, suppression of PKCδ activity with the kinase inhibitor rottlerin, siRNA directed against PKCδ or with loss of function PKCδ mutants effectively increased a number of key biochemical events in the dopamine pathway, including TH phosphorylation at serine 40 (TH-ser40), TH enzymatic activity, and dopamine synthesis in neuronal cell culture models. Additionally, inhibition of PKCδ in cell culture and animal models reduced the dephosphorylation activity of PP2A and thereby increased $TH^{ser40}$ phosphorylation. Based on co-immunoprecipitation and kinase assays, we found that PKCδ not only physically associates with PP2A but also phosphorylates the phosphatase. To further validate our findings, we used the PKCδ knockout (PKCδ KO) mouse model. Consistent with other results, we found greater $TH^{ser40}$ phosphorylation and reduced PP2A activity in the substantia nigra of PKCδ −/− mice than in wild-type mice. Importantly, this was accompanied by an increased dopamine level in the striatum of PKCδ −/− mice. Collectively, these results suggest that PKCδ phosphorylates PP2A to enhance its activity and thereby reduces $TH^{ser40}$ phosphorylation and TH activity and ultimately dopamine synthesis.

The PKC family consists of more than 11 isoforms and is subdivided into three major subfamilies, which include conventional PKC (α, βI, βII, γ), novel PKC (δ, ε, η, θ), and atypical PKC (τ/λ, ζ) (Newton, 2003; Spitaler and Cantrell, 2004). PKCδ, a key member of the novel PKC family, is a redox sensitive kinase in various cell types important in cell differentiation, proliferation and secretion. Our recent studies demonstrate that PKCδ is an oxidative stress sensitive kinase, and activation of this kinase via capase-3 dependent proteolysis induces apoptotic cell death in cell culture models of PD (Kaul et al., 2003; Yang et al., 2004; Latchuomycande et al., 2005). We also observed a high level of PKCδ expression in nigral dopaminergic neurons and a physical association of PKCδ with TH in intact rodent brain. Previous studies have shown that general PKCs can phosphorylate TH Ser40 and TH Ser31 to increase TH activity (refs). Herein, we report a novel interaction of PKCδ with TH in which PKCδ negatively regulates TH activity and dopamine synthesis by enhancing PP2A activity in a dopaminergic neuronal system.

Materials and Methods

Chemicals.

Rottlerin, NSD-1015 (3-Hydroxybenzylhdrazine hydrochloride), okadaic acid, dibutyryl cAMP, protease cocktail, ATP, protein-A-sepharose, protein-G-sepharose and anti-β-actin antibody were obtained from Sigma-Aldrich (St. Louis, Mo.); mouse tyrosine hydroxylase antibody, PhosphoTH-Ser40 and Ser31 antibodies were purchased from Chemicon (Temecula, Calif.); the rabbit polyclonal antibody for tyrosine hydroxylase was obtained from Calbiochem Bioscience, Inc. (King of Prussia, Pa.); rabbit PKCδ antibody was purchased from Santa Cruz Biotechnology, Inc. (Santa Cruz, Calif.); mouse PKCδ antibody and PP2A antibody were from BD Biosciences (San Jose, Calif.); anti-rabbit and anti-mouse secondary antibodies and the ECL chemiluminescence kit were purchased from Amersham Pharmacia Biotech. (Piscataway, N.J.). Alexa 488 conjugated anti-rabbit/mouse, Cy3 conjugated anti-rabbit/mouse antibody and Hoechst 33342 were purchased from Molecular Probes, Inc. (Eugene, Oreg.). [γ-$^{32}$P]ATP was purchased from Perkin Elmer Life Science Products (Boston, Mass.). Serine/Threonine phosphatase assay kit was purchased from Promega; AMAXA® Nucleofector™ kit was from Amaxa (AMAXA GmbH, Germany). The Bradford protein assay kit was purchased from Bio-Rad Laboratories (Hercules, Calif.). RPMI, fetal bovine serum, L-glutamine, penicillin, and streptomycin were purchased from Invitrogen (Gaithersburg, Md.). The siRNA silencer construction kit and labeling kit were purchased from Ambion (City, State). Quantity One 4.2.0 software was purchased from Bio-Rad and Vector NTI software was purchased from InforMax.

Animal Studies.

Six to 8-week-old 26/C57/bL mice and PKCδ knockout mice weighing 30 g were housed in standard conditions: constant temperature (22±1° C.), humidity (relative, 30%) and a 12-h light/dark cycle, and were allowed free access to food and water. The animals and protocol procedures were approved and supervised by the Committee on Animal Care (COAC) at the Iowa State University.

Cell Culture Models.

PC12 and N27 cells were cultured as described earlier (Anantharam et al., 2002; Kaul et al., 2003). Briefly, cells were grown in RPMI 1640 medium containing 10% fetal bovine serum, 2 mM L-glutamine, 50 units of penicillin, and 50 μg/ml streptomycin. Cells were maintained in a humidified atmosphere of 5% $CO_2$ at 37° C. N27 cells were differentiated with 2 mM dibutyryl cAMP for 3-5 days and then used for experiments described below. Primary mesencephalic neuronal cultures were prepared from the ventral mesencephalon of gestational 16-18-day-old mice embryos as described previously (Yang et al., 2004). Mesencephalic tissues were dissected and maintained in ice-cold $Ca^{2+}$-free HESS and then dissociated in HBSS solution containing trypsin-EDTA (0.25%) for 20 min at 37° C. The dissociated cells were then plated at equal density ($0.5 \times 10^6$ cells) in 30-mm-diameter tissue culture wells precoated with poly-L-lysine (1 mg/ml). Cultures were maintained in a chemically defined medium consisting of neurobasal medium fortified with B-27 supplements, L-glutamine (500 μM), penicillin (100 IU/ml), and streptomycin (100 μg/ml) (Life Technologies). The cells were maintained in a humidified $CO_2$ incubator (5% $CO_2$, 37° C.) for 24 hr and then treated with cytosine arabinoside (10 μM) for 24 hr to inhibit glial cell proliferation. Half of the culture medium was replaced every 2 days. Approximately 6-7-day-old cultures were used for experiments.

Transfection of $PKCδ^{K376R}$ Gene in N27 Cells and Primary Mesencephalic Neurons.

Plasmid $pPKCδ^{K376R}$-V5 encodes the loss of function PKCδ-V5 epitope tagged mutant protein; K376R refers to the mutation of the lysine residue at position 376 to arginine in the catalytic site resulting in inactivation of the kinase. Plasmid pLacZ-V5 encodes the β-galactosidase protein alone with a V5-epitope and is used as a vector control. N27 cells stably expressing $PKCδ^{K376R}$-V5 (herein referred to as PKCδ-DN cells) and LacZ alone-expressing cells (LacZ cells) were cultured as described previously (Kitazawa et al., 2005). PKCδ-DN or LacZ expressing N27 cells were identified by immunostaining of the C-terminal V5 epitope on expressed proteins and were differentiated with cAMP analogs (e.g. dibutyral cAMP) prior to experiments. PKCδ-DN and LacZ were also transiently expressed in mouse primary mesencephalic neurons using an AMAXA® Nucleofector™ kit (AMAXA GmbH, Germany). As described above, primary mesencephalic neurons were prepared from the midbrain of 16-18-day-old mice embryos. After digestion with trypsin-EDTA-HBSS, the primary neurons were homogenously resuspended with transfection buffer provided with the kit to a final concentration of $4-5 \times 10^6$ neurons/100 μl and mixed with 1 μg plasmid DNA encoding either PKCδ-DN-V5 or LacZ-V5. Electroporation was carried out with an AMAXA® Nucleofector™ as per the manufacturer's protocol. The transfected neurons were then transferred to 24 well plates containing poly-L-lysine or laminin coated coverslips. After 24 hr, the primary neurons were fixed and used for immunocytochemistry. Transfection efficiency was >75% as determined by immunostaining of V5-expression.

Design, Synthesis and Transfection of siRNA.

Small interfering RNAs (siRNAs) were prepared by an in vitro transcription method as described previously (Yang et al., 2004). Cy-3 labeling of siRNA and transfections were carried out as described in a recent publication (Yang et al., 2004). We used the siRNA PKCδ-4 and non-specific siRNA (siRNA-NS) for this study.

Treatment Paradigm.

PC12 cells, differentiated N27 dopaminergic cells and primary mesencephalic neurons were exposed to 1-10 μM rottlerin for the duration of the experiment. DMSO (0.01%) was used as vehicle control. PKCδ-DN- and Lac Z-expressing N27 cells were only treated with 0.01% DMSO. For measurement of TH activity in rottlerin-treated cultures, cells were exposed to 2 mM NSD-1015 for 1 hr prior to rottlerin treatment. Untreated or vehicle treated cells were used as control samples.

Western Blotting.

Cell and brain lysates containing equal amounts of protein were loaded in each lane and separated on a 10-12% SDS-PAGE gel as described previously (Kaul et al., 2003). After the separation, proteins were transferred to nitrocellulose membrane, and nonspecific binding sites were blocked by treating with 5% nonfat dry milk powder. The membranes were then treated with primary antibodies directed against PKCδ (rabbit polyclonal or mouse monoclonal, 1:2000 dilution), TH (rabbit polyclonal or mouse monoclonal, 1:1000), phospho TH-ser40 (rabbit polyclonal, 1:1000), phospho TH-ser31 TH (rabbit polyclonal, 1:1000), or PP2A (mouse monoclonal, 1:1000). The primary antibody treatments were followed by treatment with secondary HRP-conjugated anti-rabbit or anti-mouse IgG (1:2000) for 1 hr at RT. Secondary antibody-bound proteins were detected using Amersham's ECL chemiluminescence kit. To confirm equal protein loading, blots were reprobed with a β-actin antibody (1:5000 dilution). Western blot images were captured with a Kodak 2000 MM imaging system and data were analyzed using 1D Kodak imaging analysis software.

Co-Immunoprecipitation.

Immunoprecipitation studies were conducted to determine the association properties between PKCδ, TH and PP2A and were performed as described in our recent publications (Kaul et al., 2005a and b). Briefly, cells or mouse brain substantia nigral tissue were washed with ice-cold $Ca^{2+}$-free PBS saline and resuspended in a lysis buffer [25 mM HEPES (pH 7.5), 20 mM β-glycerophosphate, 0.1 mM sodium orthovanadate, 0.1% Triton X-100, 0.3 M NaCl, 1.5 mM $MgCl_2$, 0.2 mM EDTA, 0.5 mM DTT, 10 mM NaF, and protease inhibitor cocktail]. The suspension was kept on ice for 30 min and then centrifuged at 10,000×g for 5 min. The supernatants were collected and used for immunoprecipitation. Extracts containing ~200 μg total protein were immunoprecipitated overnight at 4° C. using 5-20 μg of anti-PKCδ, anti-TH, and anti-PP2A antibodies. The immunoprecipitates were then adsorbed onto Protein A or G sepharose for 1 hr at 4° C. The sepharose-bound antigen-antibody complexes were washed three times with lysis buffer to remove unbound proteins. For association studies, samples were mixed with 2×SDS PAGE loading buffer, boiled for 5 min, and then proteins were separated on SDS-PAGE and subjected to Western blot as described earlier.

$^{32}P$ Phosphorylation Assays.

To determine whether PKCδ can directly phosphorylate PP2A we used both immunoprecipitated PKCδ and recombinant PKCδ in in vitro phosphorylation assays. Immunoprecipitations were performed as described earlier. Briefly, PKCδ and PP2A were immunoprecipitated from N27 cell lysates using rabbit polyclonal PKCδ antibody and mouse monoclonal PP2A antibody, respectively. The samples then were incubated with protein A or protein G sepharose, and the immunoprecipitates were used in in vitro phosphorylation assays. Immunoprecipitated or recombinant PKCδ was resuspended in 2× kinase buffer [40 mM Tris (pH 7.4), 20 mM $MgCl_2$, 20 μM ATP, 2.5 mM $CaCl_2$] and the reaction was started by adding 20 μl of reaction buffer containing immunoprecipitated PP2A and 5 μCi of [γ-$^{32}P$] ATP (4500 Ci/mM). After incubation for 10 min at 30° C., the reaction was terminated by addition of 2×SDS-gel loading buffer and separated by SDS-PAGE. PP2A and histone H1 phosphorylated bands were detected using a Personal Molecular Imager (FX model, BioRad Labs) and quantified with Quantity One 4.2.0 software. Histone H1 substrate was used as a positive control for PKCδ kinase activity.

PP2A Assay.

To determine PP2A phosphatase activity, we used the Serine/Threonine phosphatase assay kit from Promega. Briefly, N27 cells and substantia nigral tissue from mouse brain were homogenized in lysis buffer (25 mM Tris-HCl, 10 mM β-mercaptoethanol, 2 mM EDTA, protease inhibitor) supplied with the kit. After centrifugation, the supernatants were used for the assay. PP2A activity was determined by measuring the amount of free phosphate generated in a reaction by measuring the absorbance of a molybdate:malachite green: phosphate complex at 600 nm using the Spectramax plate reader (Molecular Devices). The effective range for the detection of phosphate released in this assay is 100-4,000 pmol of phosphate.

Tyrosine Hydroxylase Activity.

TH enzyme activity was measured by the established method of Hayashi et al., 1988, in which DOPA levels were quantified as an index of TH activity after inhibition of DOPA decarboxylase with the decarboxylase inhibitor NSD-1015 ((Hayashi et al., 1988). Briefly, cells were incubated with Krebs-HEPES buffer (pH 7.4) containing 2 mM NSD-1015 at 37° C. for 30 min, and then subjected to the treatment paradigm as described earlier. After treatment, cells were collected and resuspended in antioxidant solution, sonicated, centrifuged, and DOPA levels in the supernatants were measured by HPLC detection as described below. Reference: Hayashi Y, Miwa S, Lee K, Koshimura K, Kamel A, Hamahata K, Fujiwara M (1988), A nonisotopic method for determination of the in vivo activities of tyrosine hydroxylase in the rat adrenal gland, Anal Biochem, 168: 176-183.

Measurements of DA and its Metabolites.

DA and DOPAC levels in PC12, N27 cells and in brain striatal tissues were determined by high-performance liquid chromatography with electrochemical detection (HPLC-EC); samples were prepared as described previously (Kitazawa et al., 2001). The DA and DOPAC levels were measured as pg/mg protein and expressed as percent of control.

Immunocytochemistry.

Immunostaining of PKCδ, TH, Ser40 P-TH and Ser31 P-TH was performed in PC12, N27 and primary mesencephalic neurons. Cells were grown on poly-L-Lysine-coated glass cover slips. After treatment, the cells were fixed with 4% paraformaldehyde and processed for immunohistochemical staining. First, non-specific sites were blocked with 5% normal goat serum containing 0.4% BSA and 0.2% Triton-X 100 in PBS for 20 min. Cells were then incubated with antibodies directed against PKCδ (1:500 dilution), TH (1:500 dilution), and P-THSer40 (1:500 dilution) overnight at 4° C. followed by incubation with either Alexa 488-conjugated (green, 1:1000) or Cy3-conjugated (red, 1:1000) secondary antibody for 1 hr at RT. Secondary antibody treatments were followed by incubation with Hoechst 33342 (10 μg/ml) for 3 min at room temperature to stain the nucleus. Then the coverslips containing stained cells were washed with PBS, mounted on a slide, and viewed under a Nikon inverted fluorescence microscope (Model TE-2000U); images were captured with a SPOT digital camera (Diagnostic Instruments, Sterling Heights, Mich.).

Data Analysis.

Data analysis was performed using Prism 3.0 software (GraphPad Software, San Diego, Calif.). Data were first analyzed using one-way ANOVA and then Bonferroni's post-test was performed to compare all treatment groups, and differences with $p<0.05$ were considered significant.

Results

Figure 9:
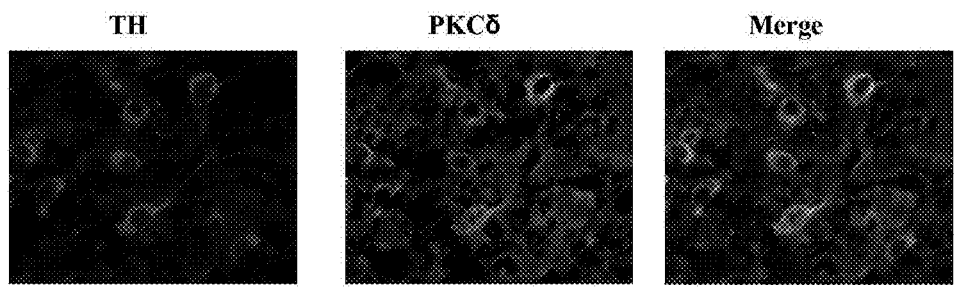
FIG. 9. Physical association between PKCδ and TH in mice brain and PC12 cells. A. Colocalization of PKCδ and TH in the mouse substantia nigra. B and C, Co-immunoprecipitation of PKCδ with TH in mice brain lysate (B: left panel) and PC12 cell lysate (C: left panel). Brain lysates and Cell lysates were immunoprecipitated with PKCδ antibody (rabbit, 1:100) or control IgA (1:100). Immunoprecipitates were loaded onto SDS-polyacrylamide gel and analyzed by Western blots by using TH antibody (mouse, 1:1000). Reverse co-immunoprecipitation of TH with PKCδ in mice brain lysate (B: right panel) and PC12 cell lysate (C: right panel). Lysates were immunoprecipitated with TH antibody (mouse, 1:100) or control IgG (1:100). The immunoprecipitates were electrophoresed and immunoblotted with PKCδ antibody (rabbit, 1:2000).
Figure 9:
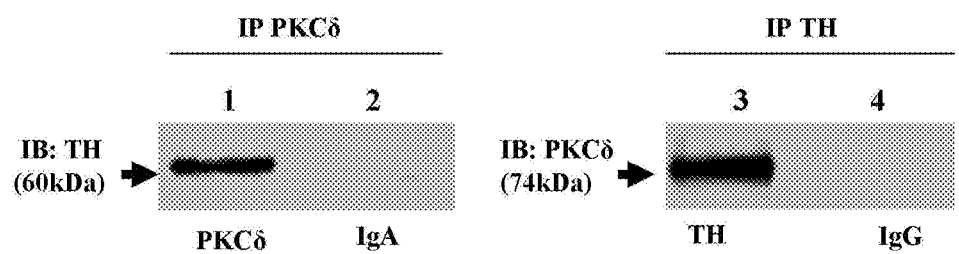
Figure 9:
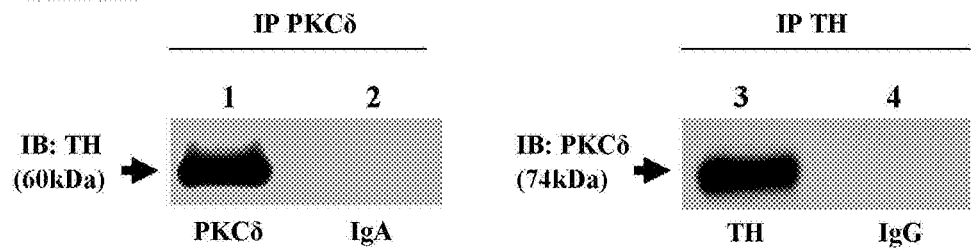

PKCδ Physically Associates with TH:

First we examined the level of PKCδ expression in nigral dopaminergic neurons. Double immunostaining of mouse nigral tissues with PKCδ and TH showed a strong colocalization of these molecules (FIG. 9A). To further prove their possible interaction, we performed co-immunoprecipitation and reverse immunoprecipitation studies. As shown in FIG. 9A, immunoprecipitation with PKCδ antibody followed by immunoblotting with TH antibody showed a clear association of PKCδ with TH in mouse substantia nigral lysate. In reverse immunoprecipitation analysis, TH antibody was used for immunoprecipitation and PKCδ antibody was used for immunoblotting. FIG. 9B shows a PKCδ band in TH immunoprecipitates from mouse brain, indicating an association between these two proteins (FIG. 9B). Rabbit IgG (Lane 2) and mouse IgG (Lane 4) were used as negative experimental controls for immunoprecipitation analysis. These results clearly indicate that PKCδ physically associates with TH in the dopaminergic neuronal system.

To further determine the functional relationship between PKCδ and TH, we used a PC12 model, which has been used extensively for post translational regulation of TH. First we performed immunoprecipitation studies to verify that PKCδ interacts with TH. Similar to nigral tissue, immunoprecipitation and reverse immunoprecipitation studies showed a clear association and interaction between PKCδ and TH (FIG. 9C). These results not only confirmed the PKCδ and TH interaction in dopamine producing cells but also indicated the usefulness of PC12 cells for examining the role of PKCδ in the regulation of TH function.

Figure 10:
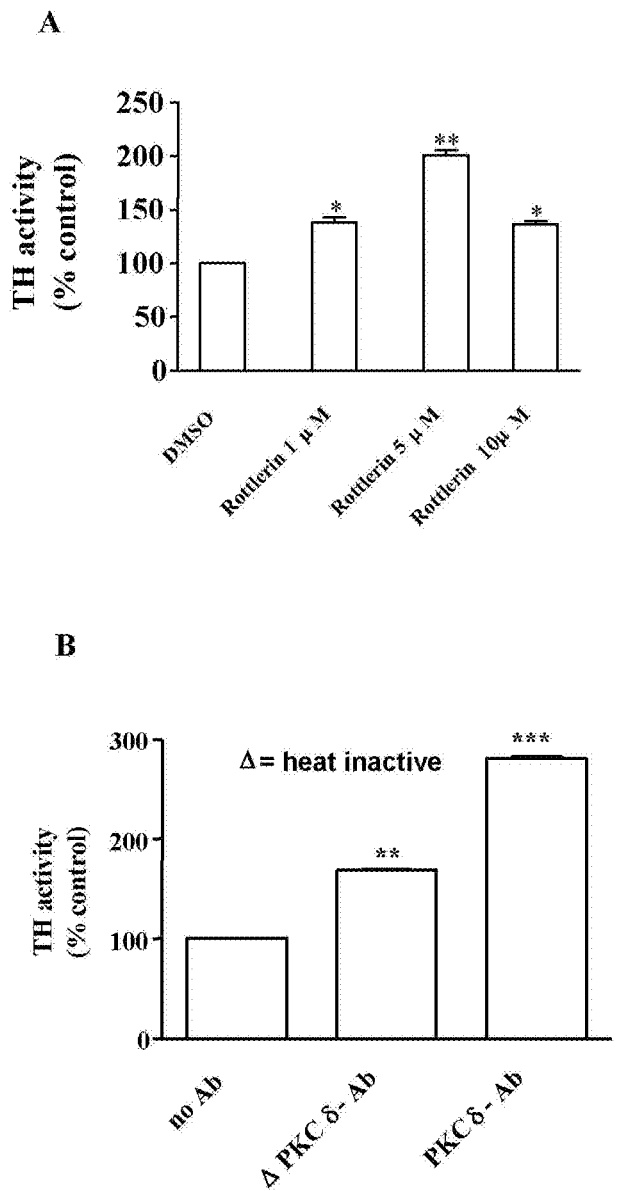
FIG. 10. Effects of PKCδ inhibitor rottlerin and PKCδ antibody ablation on TH activity in PC12 cells. A, PC12 cells were incubated in the presence of DOPA decarboxylase inhibitor NSD-1015 (2 mM) for 1 hour. After incubation and extraction, total L-DOPA levels were measured by HPLC. L-DOPA levels were increased by treatment with PKCδ inhibitor Rottlerin (1, 5, 10 µM, 3 hrs). Results are shown as mean SEM (n=8). $p<0.01$. B, Cell lysate from PC12 cells first were incubated in the presence of NSD-1015, followed by treatment with PKCδ Antibody (rabbit, 1:100) or heat-inactive PKCδ Ab (1:100) for 3 hours. L-DOPA levels were significantly greater with PKCδ Ab and heat-inactive Ab incubation than no treatment control group. Data are presented as the mean±SEM (n=7) for each condition. $p<0.01$, ***$p<0.001$.

PKCδ Inhibition Enhances TH Activity:

Since PKCδ colocalized with TH, we examined whether PKCδ has any influence on TH activity. As a first step, we determined TH activity under conditions of PKCδ inhibition using various doses of the PKCδ specific inhibitor rottlerin. TH activity was measured by determining DOPA levels following inhibition of DOPA decarboxylase with the enzyme inhibitor NSD-1015 as described in the methods section. PC12 cells were exposed to 2 mM NSD-1015 for 1 hr prior to treatment with the PKCδ specific inhibitor rottlerin for 3 hr. We used 1-10 µM rottlerin in the present study because we previously showed this dose range effectively inhibits PKCδ activity in PC12 cells (Anantharam et al., 2001). As shown in FIG. 10A, rottlerin treatment significantly increased intracellular DOPA levels, indicating increased TH activity following PKCδ inhibition. Treatment with 1 µM, 3 µM and 10 µM rottlerin increased TH activity to 2091.09±80.17, 3045±75.31 and 2067±43.83 pg DOPA/$10^6$ cells/hr respectively compared with DMSO 1519±90.74 pg DOPA/$10^6$ cells/hr. To further confirm the effect of PKCδ inhibition on TH activity, we used PKCδ antibody to inhibit PKCδ and then measured TH activity. We incubated NSD-1015-treated PC12 cell lysates with rabbit polyclonal PKCδ antibody (1:100 dilution) for 3 hr to inactivate PKCδ and then measured DOPA levels. As shown in FIG. 10B, NSD-1015-treated PC12 cell lysates incubated with PKCδ antibody exhibited significantly enhanced DOPA levels compared to cell lysates incubated with heat-inactivated PKCδ antibody and untreated cells. DOPA levels in the PKCδ antibody treatment group were about 3-fold higher, and the heat-inactivated PKCδ antibody treatment group also showed marginally increased TH activity compared to the untreated control group. Together, these results suggest that inhibition of PKCδ activation results in increased TH activity.

Figure 11:
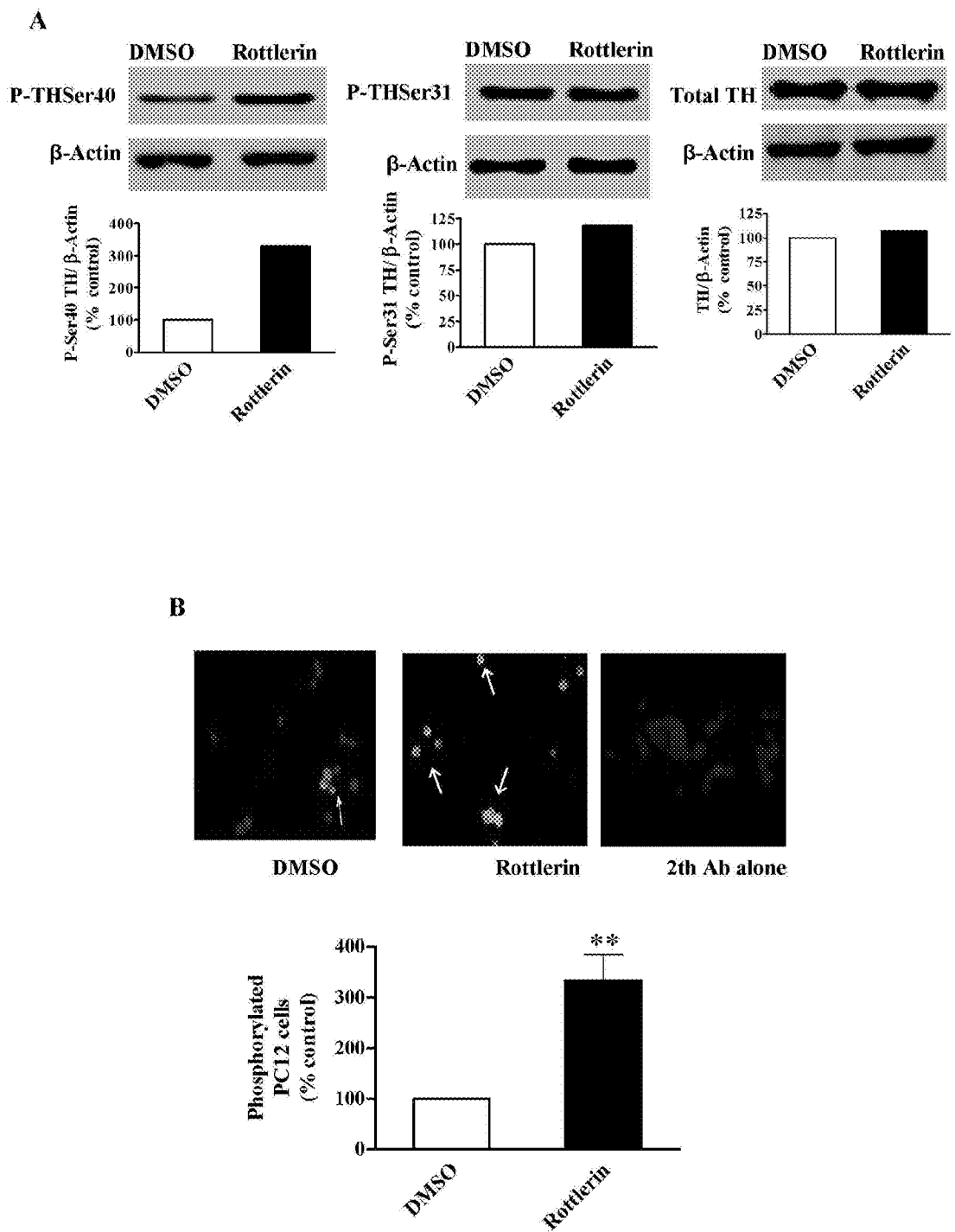
FIG. 11. Effect of PKCδ inhibitor on TH phosphorylation in PC12 cells. Comparison of total TH and specific phosphorylation of TH at site serine-40 (Ser 40), serine-31 (Ser 31) in PC12 cells exposed to Rottlerin (5 µM) for 3 hours. Immunoblot analyses of total TH and TH phopshorylation at Ser40, ser31 are shown in A, respectively. Immunostaining for phos-phoTH (Ser40) positive PC12 cells was shown in B. Phosphorylated PC12 cells were counted from 6 different areas in each group (**$p<0.01$).

Effect of PKCδ Inhibition on TH Phosphorylation:

Since inhibition of PKCδ resulted in enhanced TH activity, we examined whether PKCδ has any effect on the phosphorylation status of TH. It is well established that TH activity can be regulated by phosphorylation of multiple serine residues and serine phosphorylation at positions 31 and 40 have been suggested to play a key role in TH activation and increased dopamine biosynthesis. We measured the extent of TH-ser40 and TH-ser31 phosphorylation in immunoblots using phosphospecific antibodies directed against TH-ser31 and TH-ser40. As shown in FIG. 11A, the level of THser40 phosphorylation was significantly enhanced in rottlerin treated cells (3 µM rottlerin for 3 hr), whereas the level of THser31 phosphorylation was unaltered. Similarly, the level of total TH was unaltered in rottlerin-treated PC12 cells as compared to DMSO control (0.01%)-treated cells. Nitrocellulose membranes were reprobed with β-actin antibody and the density of the 43 kDa β-actin band was identical in all lanes, confirming equal protein loading. Densitometric analysis of the 60 kDa TH-ser40 band in FIG. 11A revealed a 3-fold increase in phosphorylation as compared to vehicle-treated cells, whereas there was no increase in levels of TH-Ser31. THSer40 phosphorylation was also confirmed in immunofluorescence measurements. After treatment with 3 µM rottlerin for 3 hr, PC12 cells were fixed and processed for immunofluoresence staining of TH-ser40 using Alex 488 secondary antibody. An increased level of bright green immunofluorescence staining was observed in rottlerin-treated cells, but only a weak staining was observed in DMSO-treated cells, indicating that PKCδ inhibition results in increased phosphorylation of TH ser40. No staining was observed in cells stained with Alexa 488 alone. Cell count analysis of images using Metamorph image analysis revealed that rottlerin-treatment induced the increase in TH-ser40 stained cells by 333% compared to DMSO-treated cells (FIG. 11B). These results demonstrate that PKCδ inhibition results in enhanced TH phosphorylation specifically at ser40.

Effect of Loss of Function PKCδ Mutant on TH Activity and DA Synthesis in Mesencephalic Dopaminergic Neuronal Cells:

Although PC12 cells are a good model to study TH function, they are non-neuronal cells derived from adrenal pheochromocytoma. Therefore, to further determine whether PKCδ alters TH activity in neuronal cells, we used immortalized rat fetal mesencephalic dopaminergic neuronal cells (N27 cells), which are a homogenous population of TH positive neuronal cells that synthesize and release dopamine upon differentiation (Zhou et al., 2000; Clarkson et al., 1999). Also, the N27 dopaminergic cell line is easily transfectable and convenient for establishing stable cell lines compared to hard-to-transfect PC12 cells. In recent years, this neuronal cell line has been recognized by many investigators, including us, as a highly useful cell culture model for studying degenerative mechanisms in Parkinson's disease (Kaul et al., 2003; Miranda et al., 2004; Kaul et al., 2005a; Kaul et al., 2005b; Yong et al., 2004; Peng et al., 2005).

Figure 12:
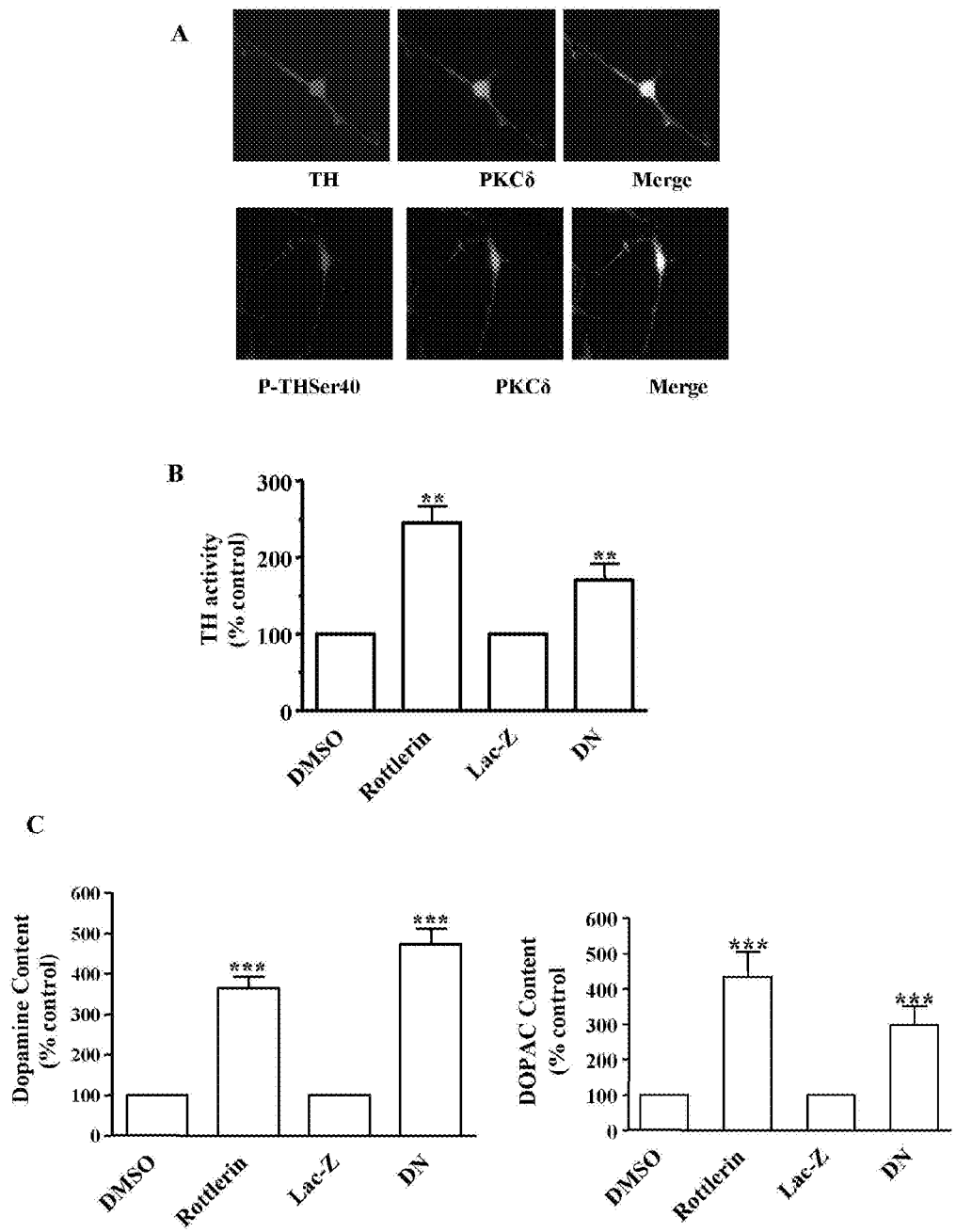
FIG. 12. Effects of PKCδ inhibitor and Dominant-negative (DN)-PKCδ mutant on TH activity and cellular DA level in immortalized dopaminergic neurons (N27 cells). Immunofluorescence staining showed the colocalization between PKCδ and TH, PhosphoTH (Ser40) in differentiated N27 cells (A). TH activity in N27 cells was highly enhanced by rottlerin and DN-PKCδ mutant (B). Dopamine and DOPAC level were significantly increased in DN-PKCδ mutant cells and rottlerin treated cells (C). Data are presented as the mean±SEM (n=6) for each condition. $p<0.01$, *$p<0.001$.

First, we examined whether PKCδ interacts with TH in a manner similar to that observed in PC12 cells and mouse nigral tissue. As shown in FIG. 12A, double immunostaining studies with N27 cells showed co-localization of PKCδ with TH and TH-Ser40, further supporting the previous results of association of PKCδ with TH observed in PC12 cells. Next, we examined whether PKCδ inhibition would alter TH activity and phosphorylation status in N27 cells. For these studies, we used genetic approaches in addition to PKCδ pharmacological inhibitor studies. We utilized N27 cells stably expressing a loss of function PKCδ dominant negative mutant (PKCδ-DN) established in our laboratory (Kaul et al., 2003; Kitazawa et al., 2005). N27 cells were exposed to 2 mM NSD-1015 for 1 hr prior to a 3 hr treatment with the PKCδ specific inhibitor rottlerin or 0.01% DMSO. Then we measured the DOPA levels as a measure of TH activity in rottlerin- and DMSO-treated N27 cells. We also measured DOPA levels in PKCδ-DN expressing N27 cells and Lac-Z-expressing N27 cells (vector control). To establish the baseline, DOPA levels in cell extracts were isolated from Lac-Z- and PKCδ-DN expressing cells without prior treatment with NSD-1015. As shown in FIG. 12B, DOPA levels were significantly higher in rottlerin-treated cells compared to DMSO-treated cells, and were in agreement with the data obtained in PC12 cells (see FIG. 10). Also, TH activity was significantly higher in PKCδ-DN mutant expressing cells as compared to LacZ expressing cells (FIG. 12B). The TH activity was 1231±119.7 and 3025±266.7 pg DOPA/$10^6$ cells/hr in DMSO- and rottlerin-treated cells and 1483±146.3 and 2539±307.3 pg DOPA/$10^6$ cells/hr in LacZ and PKCδ-DN expressing cells, respectively (FIG. 12B).

Increase in TH activity should result in increase in dopamine synthesis and therefore, we measured the levels of cellular dopamine (DA) by HPLC in N27 cells expressing PKCδ-DN and in rottlerin-treated N27 cells. Vehicle-treated N27 cells and Lac-Z expressing N27 cells were used as controls. Steady-state DA levels were significantly increased in rottlerin-treated and PKCδ-DN mutant expressing N27 cells compared to DMSO-treated and LacZ expressing cells, respectively (FIG. 12C). DA level in rottlerin treated cells was 2748±208 pg/μg protein compared to 754±73 pg/μg protein in vehicle-treated N27 cells—a 4-fold increase. Similarly, DA levels in PKCδ-DN mutant expressing cells were 4806±373 pg/μg protein compared to 1015±73 pg/μg protein in LacZ-expressing cells, also a 4-fold increase (FIG. 12C). Thus, both inhibition of baseline PKCδ activity with rottlerin and loss of function PKCδ-DN mutant increased DA levels in the dopaminergic cells. To determine whether increased DA levels in the rottlerin-treated and PKCδ-DN-expressing cells were due to enhanced TH activity or due to reduced degradation of DA to its major metabolite dihydroxy phenyl acetic acid (DOPAC) by monoamino oxidase (MAO), we measured DOPAC levels. As shown in FIG. 12D, DOPAC levels were also significantly increased by 4-fold in rottlerin-treated cells and by 3-fold in PKCδ-DN-expressing cells, compared to the vehicle-treated and LacZ-expressing N27 cells, respectively. DOPAC levels were 2564±848.19 and 2783±968.31 pg/μg protein in rottlerin-treated and PKCδ-DN-expressing cells, as compared to 592±120.65 and 935±83.34 pg/μg protein in vehicle-treated and LacZ-expressing cells, respectively. Together, these data suggest that PKCδ inhibition increases DA synthesis in dopaminergic neuronal cells as a result of increased TH activation.

Figure 13:
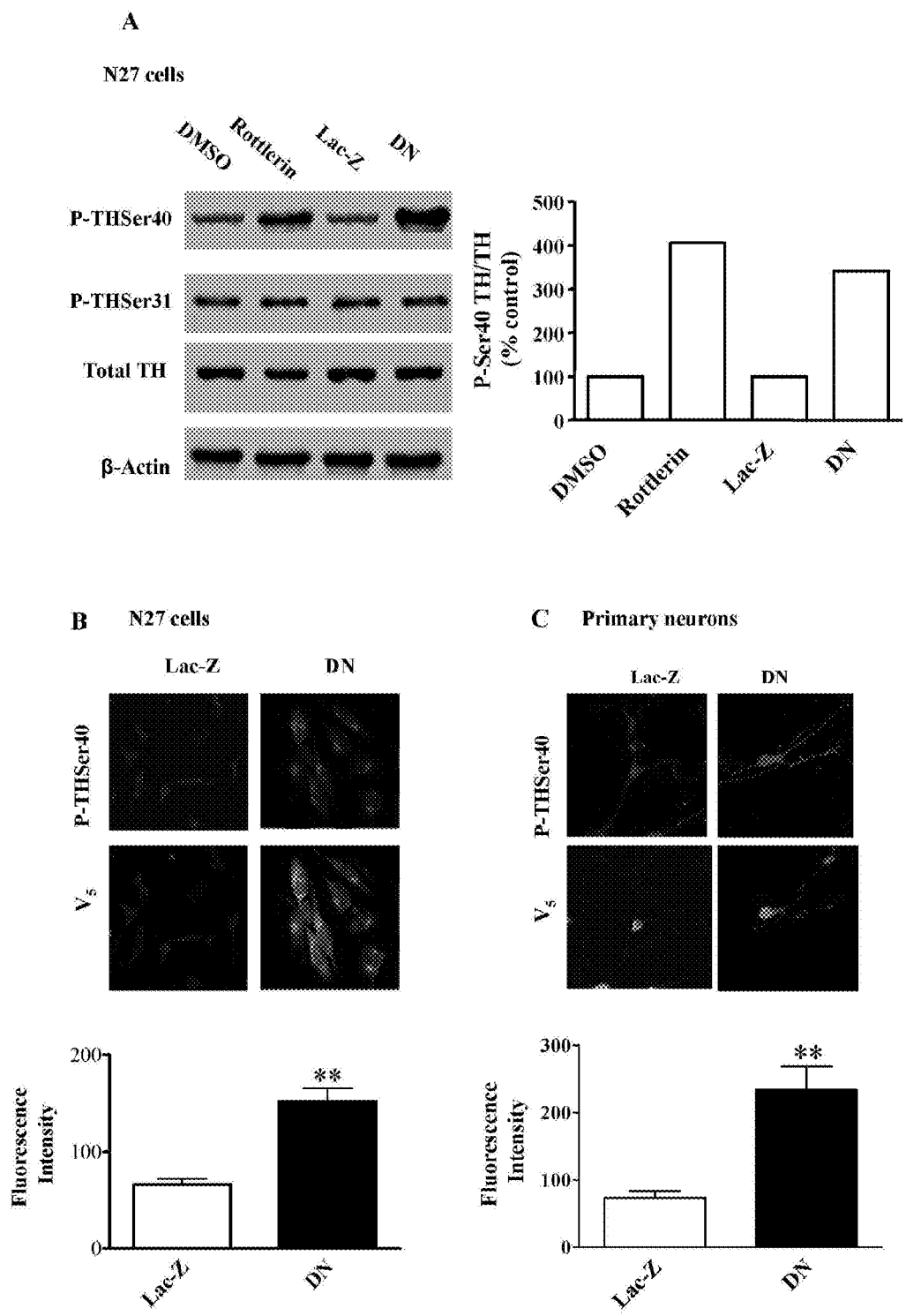
FIG. 13. Effect of PKCδ inhibition and activation on TH phosphorylation in N27 cells and TH positive primary neurons. Cell lysates from stably transfected control vector cells or DN-PKCδ mutant N27 cell line and control N27 cells with Rottlerin treatment were loaded to SDS-Page gel and immunoblotted with anti-TH Ab (rabbit, 1:1000), anti-PhosphoTH (Ser40) Ab (rabbit, 1:1000), anti-PhosphoTH(Ser31) Ab (A). PhosphoTH expression at site Ser40 were significantly reduced by Rottlerin and DN-PKCδ mutant compared with control. (A). The TH phosphorylation level in DN-PKCδ mutant N27 cell was also determined by immunocytochemical staining by using phosphoTH (Ser40) Ab (mouse, 1:500), because the vector in lentiviral system contains $V_5$ epitope, so anti-V5 Ab (mouse, 1:5000) was used to detect mutant PKCδ protein (B). The intensity of PhosphoTH (Ser40) staining in DN-PKCδ mutant N27 cells was much stronger than control vector cells (B). TH positive primary neurons were transfected with DN-PKCδ mutant by using ViraPower Lentiviral Expression System, DN-PKCδ mutant transfected TH positive neurons had more fluorescence than control TH positive neurons.

PKCδ Negatively Modulates TH-Ser40 Phosphorylation:

Since TH activity and dopamine synthesis were enhanced in N27 cells expressing PKCδ-DN and in rottlerin-treated N27 cells, we further examined whether PKCδ inhibition increases the phosphorylation status of TH in N27 dopaminergic neuronal cells. As shown in FIG. 13, the levels of TH-ser40 phosphorylation were significantly enhanced in rottlerin treated N27 cells, whereas the level of THser31 phosphorylation was significantly altered compared to DMSO-treated cells. Also, the level of total TH was unaltered in rottlerin treated N27 cells. Similarly, the TH-ser40 phosphorylation level was also significantly enhanced in PKCδ-DN expressing cells compared to LacZ expressing cells, whereas TH-ser31 phosphorylation and total TH levels were unaltered. Nitrocellulose membranes were reprobed with β-actin antibody and the density of the 43 kDa β-actin band was identical in all lanes, confirming equal protein loading. Densitometric analysis of the phosphor TH ser40 (60 kDa) band revealed a 3-4-fold increase in rottlerin-treated and PKCδ-DN expressing cells. We also confirmed TH-ser40 phosphorylation by immunofluorescence measurements in N27 cells. N27 cells stably expressing PKCδ-DN and LacZ were fixed and immunostained for phospho-specific antibody directed against TH-ser40 and an antibody directed against the $V_5$-epitope in the constructs. Secondary body labelings used were with $Cy^3$- against TH-ser40 and Alexa 488 against PKCδ-DN-$V_5$ and the LacZ-$V_5$ epitope. A bright red immunofluorescence staining was observed in PKCδ-DNM expressing cells as compared to a very weak staining in Lac-Z expressing cells, suggesting that PKCδ inhibition resulted in enhanced phosphorylation of TH at ser40. Both the LacZ and PKCδ-DN expressing cells were stained for $V_5$ (red), demonstrating the expression level of the constructs. Analysis of fluorescent intensity for TH-ser40 immunostaining revealed a 2.5-fold increase in PKCδ-DN expressing cells as compared to Lac-Z expressing cells. Collectively, these results demonstrate that PKCδ inhibition results in enhanced TH phosphorylation at ser40 in N27 dopaminergic neuronal cells.

To further confirm the regulatory role of PKCδ in TH phosphorylation in the dopaminergic system, we examined the effect of PKCδ inhibition on THser40 phosphorylation in primary dopaminergic neurons obtained from the ventral mesencephalon of E18 mouse embryos. Primary mesencephalic cultures were transfected with plasmids coding for the loss of function PKCδ-DN mutant and Lac-Z using the Amaxa nucleofector system. After 24 hr of post-transfection, primary neurons were processed for immunohistochemical analysis using TH-ser40 and $V_5$-epitope antibodies in PKCδ DN mutant and LacZ cells. As shown in FIG. 13C, immunochemical staining revealed that the extent of THser40 phosphorylation was significantly enhanced in primary neurons transfected with the PKCδ-DN mutant compared to LacZ transfected primary neurons. $V_5$ staining was used for identification of transfected cells. Fluorescent intensity analysis of TH-ser40 immunostaining showed about 2.5 times more fluorescence in primary neurons expressing the PKCδ-DN mutant as compared to Lac-Z expressing neurons. These results confirm that PKCδ inhibition negatively modulates THser40 phosphorylation in primary dopaminergic neurons.

Enhanced THSer40 Phosphorylation and DA Synthesis in PKCδ siRNA-Transfected Dopaminergic Neuronal Cells.

To further substantiate the regulatory role of TH activity and DA synthesis by PKCδ, we used an RNA interference (RNAi) approach. We recently developed PKCδ siRNAs that specifically suppress PKCδ expression without producing any cytotoxic effect in N27 dopaminergic cells (Yang et al., 2004). Following the suppression of PKCδ in N27 cells using siRNA, we measured TH-ser40 phosphorylation, DA and DOPAC levels.

Figure 14:
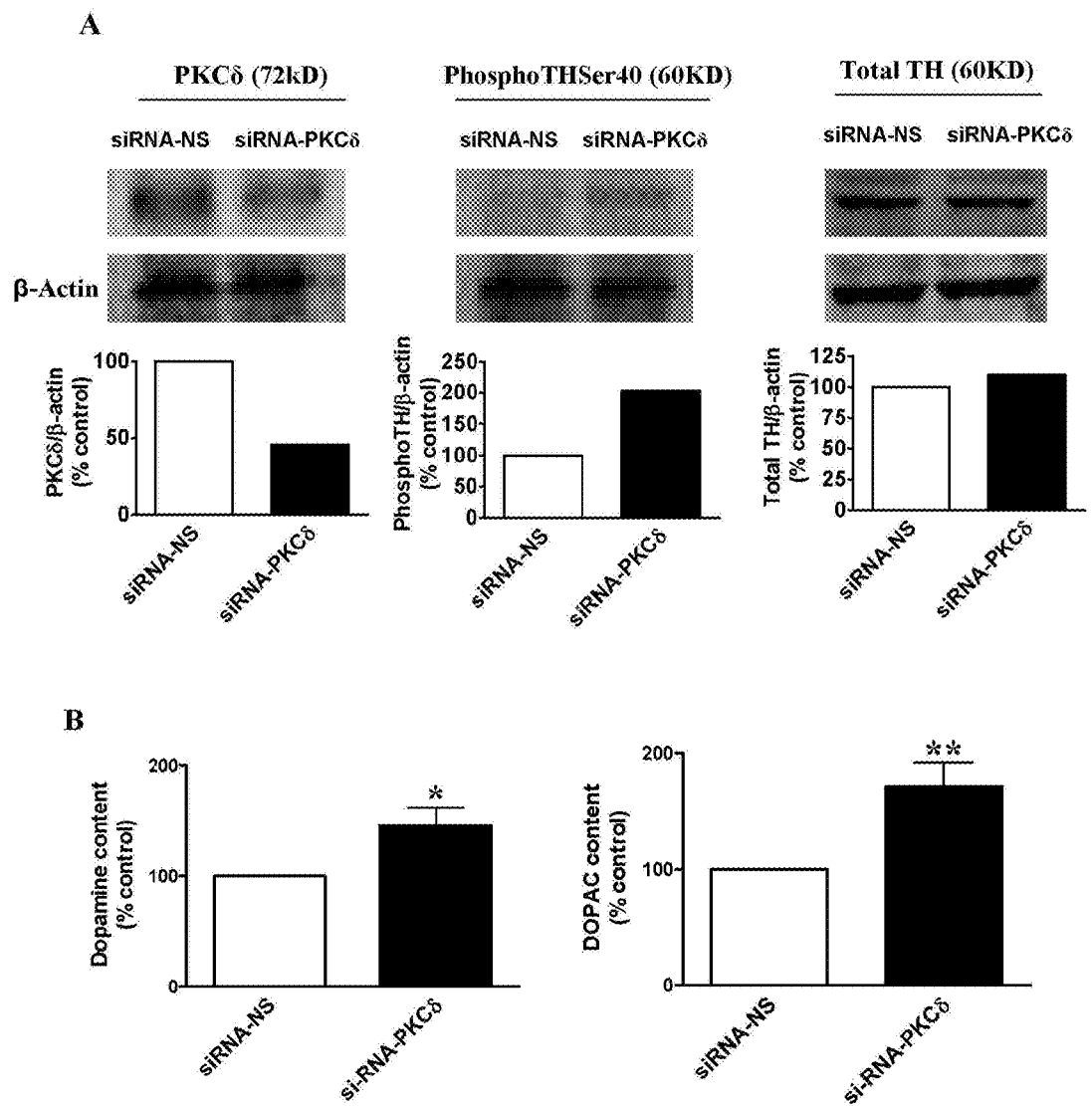
FIG. 14. Effect of PKCδ-siRNA on TH-ser40 phosphorylation, dopamine and DOPAC levels in N27 cells. The cells were transfected with PKCδ-siRNA and non-specific (NS) siRNA and then TH-ser40 level by western blot (panel A) and dopamine and DOPAC (panel B) were measured.

FIG. 14A shows a significant suppression of endogenous PKCδ expression in PKCδ siRNA-transfected cells as compared to non-specific siRNA (siRNA-NS) transfected N27 cells. A 55% reduction in PKCδ expression was observed in PKCS siRNA-transfected cells as measured by Western blot analysis. Importantly, TH-Ser40 phosphorylation levels were also significantly higher in PKCδ-siRNA-transfected cells as compared to siRNA-NS transfected N27 cells, whereas the total TH levels were similar in both siRNA-PKCδ and siRNA-NS transfected cells (FIG. 14A). Densitometric analysis of TH-Ser40 (60 kDa band) revealed a 2-fold increase in siRNA-PKCδ transfected cells compared to siRNA-NS transfected N27 cells (FIG. 14A). Reprobing of the nitrocellulose membranes with β-actin antibody showed the density of the 43 kDa β-actin band to be identical in all lanes, confirming equal protein loading. Next we measured DA and DOPAC levels in siRNA transfected N27 cells by HPLC. As shown in FIG. 14B, DA and DOPAC levels were significantly higher in siRNA-PKCδ transfected cells compared to non-specific siRNA (siRNA-NS) transfected N27 cells. A 45% increase in the DA level and a 71% increase in DOPAC were noted in PKCδ siRNA-transfected cells as compared to siRNA-NS transfected N27 cells. Together, these data further substantiate that PKCδ negatively regulates THSer40 phosphorylation and DA synthesis in dopaminergic neuronal cells.

Increased THSer40 Phosphorylation in Primary Mesencephalic Dopaminergic Neurons from PKCδ Knockout (−/−) Mice.

Figure 15:
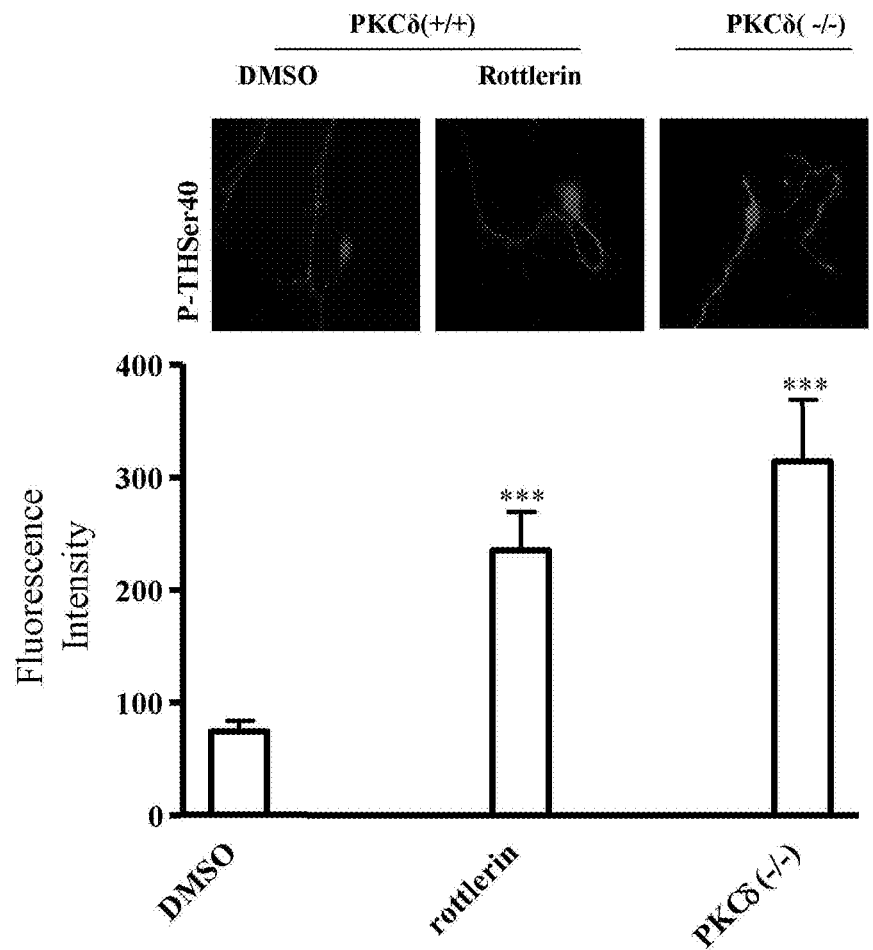
FIG. 15. Increased TH-ser40 phosphorylation in primary mesencephalic cultures treated with rottlerin (3 µM for 3 hr) and PKCδ KO cultures. TH-ser40 phosphorylation was measured by quantifying the immunofluorsence. ***$p<0.001$.

We also extended the TH phosphorylation studies conducted in primary mesencephalic dopaminergic neurons derived from E16-18 embryos to the recently available PKCδ knockout (−/−) mice (Miyamoto et al., 2002). The level of TH-ser40 phosphorylation in nigral dopaminergic neurons in PKCδ (+/+) and PKCδ (−/−) mice was compared by immunostaining. The baseline TH ser40 phosphorylation levels were significantly higher in untreated primary neurons obtained from PKCδ (−/−) mice compared to untreated PKCδ (+/+) mice (FIG. 15A). Fluorescent intensity measurements revealed that the TH-ser40 level was 3-fold higher in PKCδ (−/−) dopaminergic neurons as compared to PKCδ (+/+) mesencephalic neurons. In addition to the knockout studies, we tested the effect of the PKCδ inhibitor rottlerin on TH-ser-40 phosphorylation in the PKCδ (+/+) primary neuronal cultures. The cultures were treated with 3 μM rottlerin for 3 hr and then the level of TH-ser40 phosphorylation was measured. As shown in FIG. 15B, rottlerin treatment increased TH-ser40 phosphorylation in PKCδ (+/+) primary dopaminergic neurons. The fluorescent intensity was increased 4-fold in rottlerin-treated dopaminergic neurons as compared to dopaminergic neurons. Together, these results confirm that suppression of PKCδ increases TH-ser40 phosphorylation in dopaminergic neurons.

Effect of PP2A Inhibition on TH Activity and Ser40 Phosphorylation.

The increased TH-ser 40 phosphorylation resulting from PKCδ inhibition suggested that PKCδ may affect dephosphorylation of TH under normal conditions. Previous studies have demonstrated that protein phosphatase 2A (PP2A) is a major serine phosphatase that mediates the dephosphorylation of TH, in particular TH-ser40, resulting in the inactivation of TH. Therefore, we hypothesize that PKCδ phosphorylates PP2A to increase the phosphatase activity, which results in reduced dephosphorylation of TH-ser40 and TH activity. This would explain why inhibition of PKCδ increases TH-ser 40 phosphorylation, TH activity and dopamine synthesis.

Figure 16:
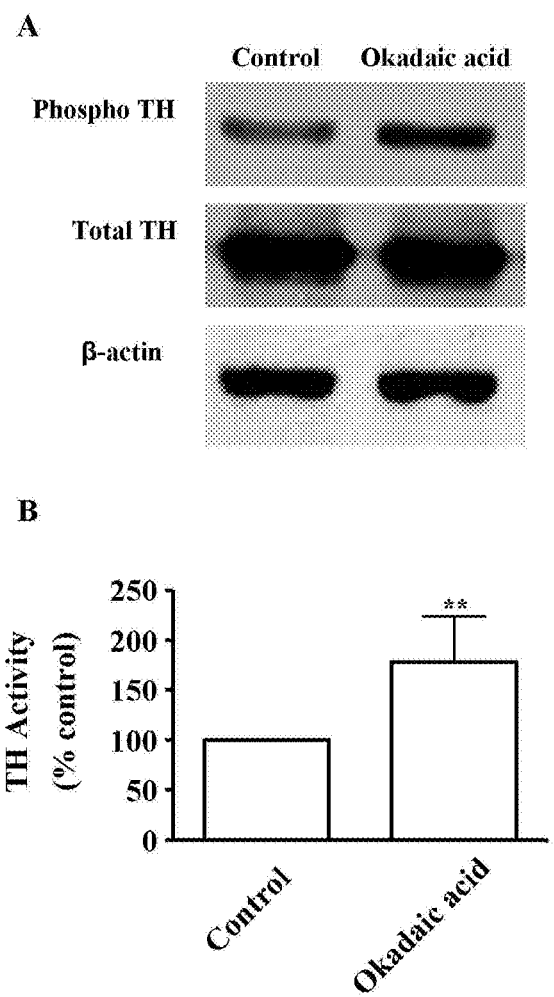
FIG. 16. Effect of phosphatase inhibitor okadaic acid on TH activity. N27 cells were treated with okadaic acid (2 µM for 2 hr) and then TH activity was measured as previously described. **$p<0.01$.

In order to test this novel hypothesis, we first examined whether PP2A regulates TH activity and TH ser40 phosphorylation in our dopaminergic model system. N27 cells were incubated with the PP2A inhibitor okadaic acid (2 μM) for 2 hr and then TH-ser40 phosphorylation and TH activity were measured. As shown in FIG. 16A, Western blot analysis revealed an increase in baseline THser40 phosphorylation levels in okadaic-treated cells as compared to untreated cells. The levels of total TH were similar in okadaic-treated and untreated cells, suggesting that increase in the THser40 phosphorylation level is not due to increased TH expression. We also measured TH activity in okadaic-treated cells. HPLC measurement of DOPA revealed a significant increase in DOPA levels indicative of increased TH activity in okadaic-treated cells (FIG. 16B). DOPA levels were 826.5±63.91 and 1434±212.6 pg/$10^6$ cells/hr in untreated and okadaic acid-treated cells. Together, these results suggest that PP2A regulates TH activity in dopaminergic neurons.

Association and Phosphorylation of PP2A by PKCδ.

Figure 17:
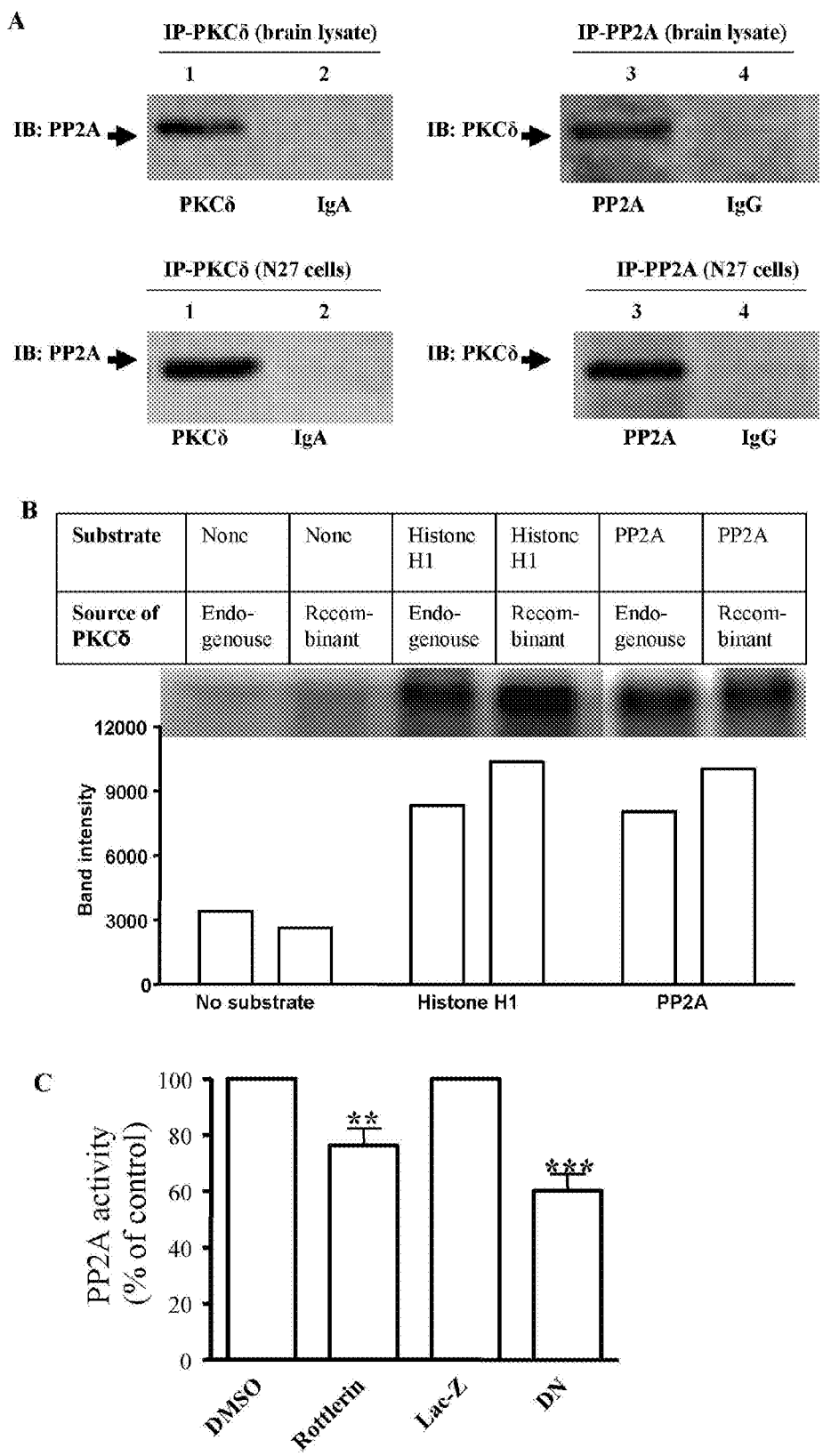
FIG. 17. PKCδ associates and directly phosphorylates PP2A in N27 cells. Cell lysates were immunoprecipitated with PKCδ Ab, PP2A Ab or control IgA/G. Immunoprecipitates were loaded onto SDS-polyacrylamide gel and analyzed by Western blots by using PP2A antibody or PKCδ antibody. Both co-immunoprecipitation (A left panel) and reverse IP (A right panel) showed interaction of PKCδ and PP2A in N27 cells (A). PP2A phosphorylation was measured using an immunoprecipitation kinase assay, PP2A and PKCδ were immunoprecipitated by using PP2A Ab or PKCδ Ab. PP2A immunoprecipitated samples were mixed with PKCδ immunoprecipitated samples or PKCδ pure protein, reaction was started by adding [γ-$^{32}$P]ATP to the complex, and the products were separated on a 12.5% SDS-PAGE gel. The PP2A phosphorylated bands were detected in both reactions (B). PKCδ inhibition on PP2A activity N27 cells. *$p<0.05$; **$p<0.01$. (C) PP2A activity was significantly reduced in rottlerin-treated cells as compared to DMSO-treated N27 cells. Similarly, PP2A activity was also significantly reduced in PKCδ-DN mutant expressing cells compared to LacZ-expressing N27 cells.

To determine the interaction between PKCδ and PP2A, we first examined whether PP2A is physically associated with PKCδ. Immunoprecipitation studies were conducted in cell culture as well as mouse nigral brain tissue to determine the possible association. FIG. 17A shows PP2A immunoreactivity in PKCδ immunoprecipitates from N27 cell lysates and substantia nigra lysates isolated from mouse brain. Similarly, in reverse immunoprecipitation analysis, the PP2A immunoprecipitates showed PKCδ immunoreactivity. Rabbit and mouse IgG were used as negative controls in these experiments. These results indicate an association between PP2A and PKCδ in both cell culture and brain tissue.

Next we determined whether physical association of PP2A with PKCδ involves direct phosphorylation of PP2A by PKCδ. We performed phosphorylation studies using immunoprecipitated PP2A protein as substrate. As shown in FIG. 17B, PP2A immunoprecipitated from N27 cells was effectively phosphorylated by PKCδ immunoprecipitates as well as by recombinant pure PKCδ as determined by $^{32}$P-kinase assays. Histone 2B was used as a positive control substrate in the phosphorylation assay. These data indicate that PKCδ associates with PP2A and phosphorylates the phosphatase.

Since PP2A can be phosphorylated by PKCδ in addition to being physically associated, we examined whether PKCδ regulates PP2A activity. We determined PP2A phosphatase activity in PKCδ inhibitor rottlerin-treated N27 cells and in N27 cells expressing the loss of function PKCδ-DN mutant. PP2A activity was significantly reduced in rottlerin-treated cells as compared to DMSO-treated N27 cells (FIG. 17C). Similarly, PP2A activity was also significantly reduced in PKCδ-DN mutant expressing cells compared to LacZ-expressing N27 cells (FIG. 17C), indicating that suppression of PKC reduces PP2A activity. PP2A activity was reduced by 31% and 56% in rottlerin-treated and PKCδ-DN expressing cells, compared to DMSO-treated and LacZ cells, respectively. Taken together with the phosphorylation studies, these data suggest that PKCδ phosphorylates PP2A and enhances PP2A activity.

Regulation of PP2A Activity, THser40 Phosphorylation, and DA Synthesis in PKCδ (−/−) Knockout Animals.

Figure 18:
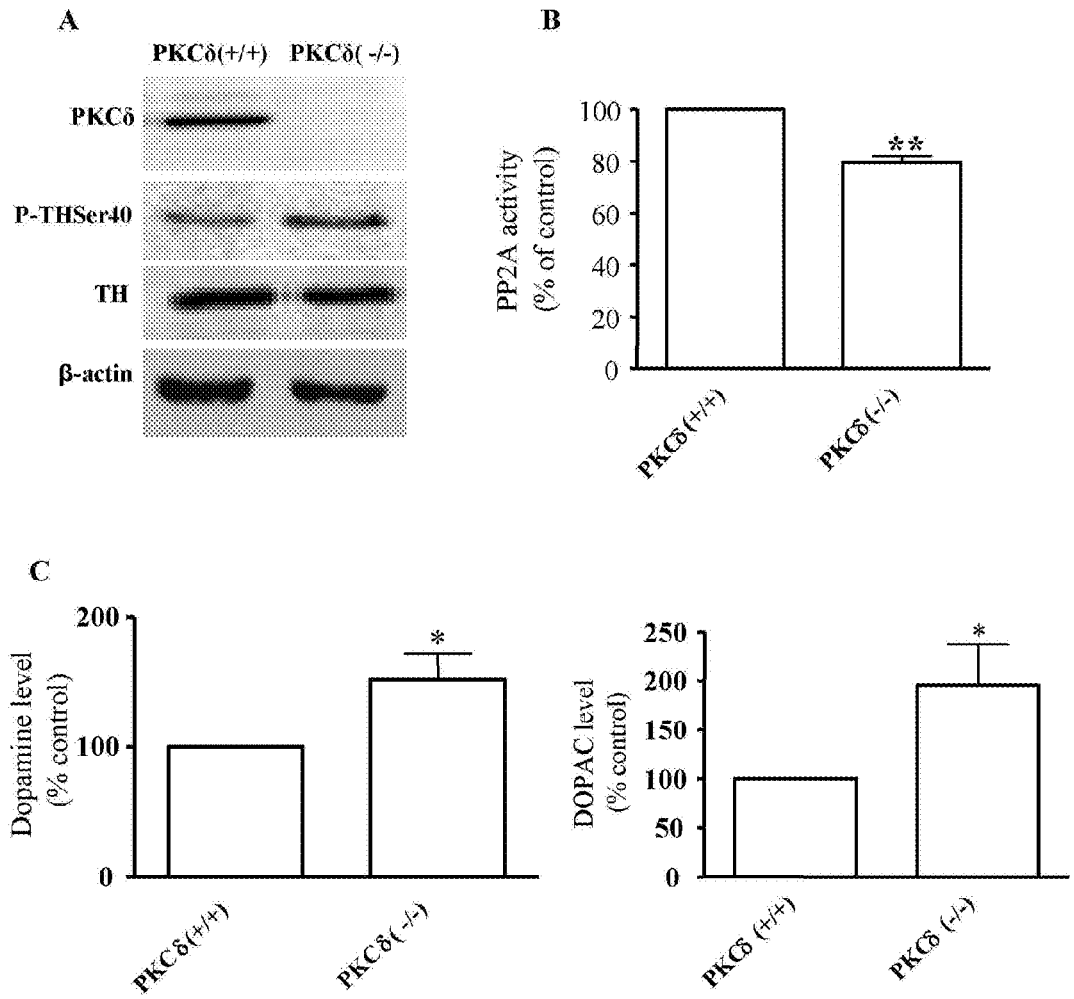
FIG. 18. PhosphoTH, dopamine and PP2A levels in SN of PKCδ Knockout (KO) mice. SN tissue from PKCδ KO mice express high PhosphoTH (Ser40) than that from wild-type mice as determined by immunoblot, total TH levels in PKCδ knockout mice are unchanged compared with wild-type mice (A). PP2A levels were measured in the nigral tissues (B), and DA and DOPAC level from striatum of PKCδ Knockout mice or wild-type mice were measured by using HPLC(C). $p<0.05$; $p<0.01$.
Figure 19:
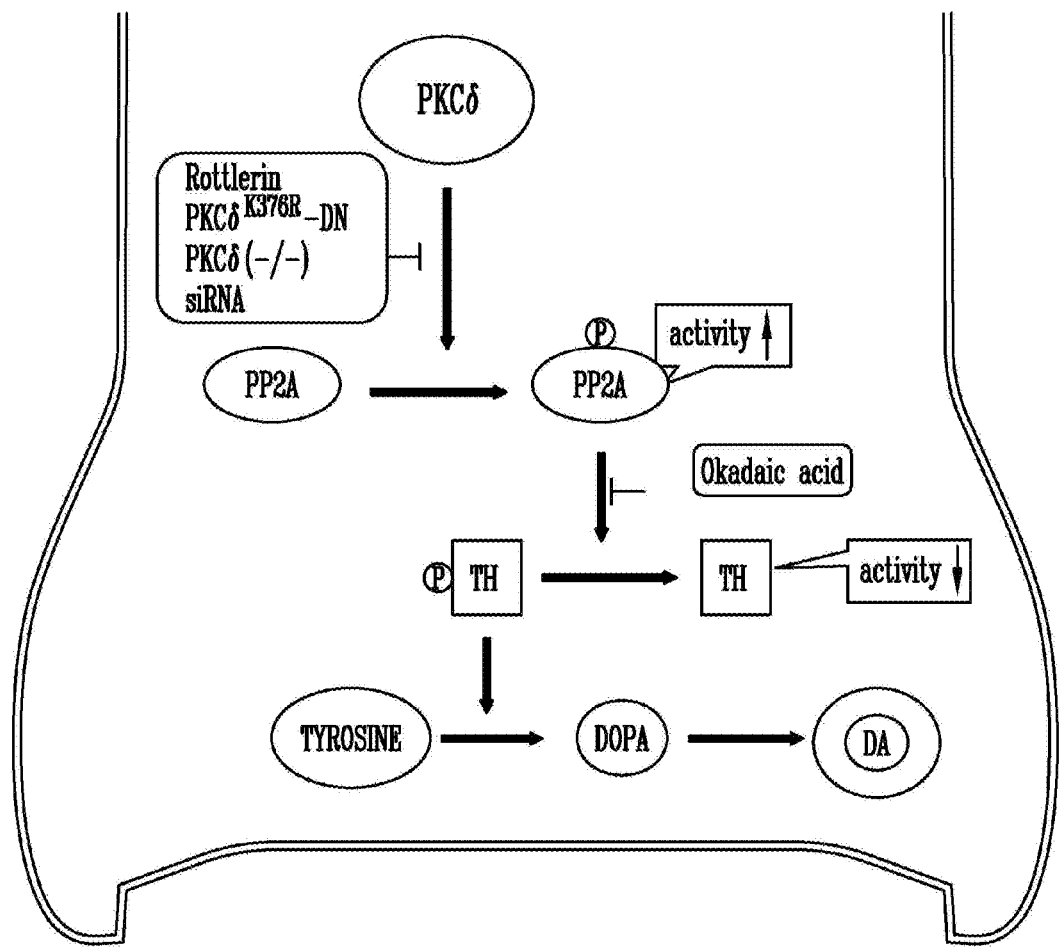
FIG. 19. A schematic depiction of regulation of TH phosphorylation and DA synthesis by PKCδ in dopaminergic neurons. 1, inhibition of PKCδ by its inhibitor rottlerin or DN-PKCδ mutant can suppress phosphatase 2A (PP2A) activity which could because of a decreased phosphorylation of PP2A; 2, as a dominant phosphatase for the dephosphorylation of TH at different serine sites, decreased PP2A activity leads to a reduced dephosphorylation of TH at ser40, and then an increased TH phosphorylation at ser40; 3, increased phosphorylation of TH causes the activation of this enzyme and increases its activity; 4, TH is the rate limiting enzyme for DA synthesis, activation of TH leads to elevated cytosolic DA in neurons. In conclusion, our data suggest that PKCδ may play an import role in the normal function of dopaminergic cells by activating PP2A to attenuate TH phosphorylation and activity in the dopaminergic neurons. Therefore, PKC inhibitors (pharmacological and genetic origin) will serve as key therapeutic compounds for enhancement of dopamine levels in the brain.

Final and unequivocal validation of the role of PKCδ in the regulation of TH activity and DA synthesis was sought by extending these studies to PKCδ (−/−) knockout animals. As shown in FIG. 18A, lack of PKCδ expression in PKCδ (−/−) animals was confirmed in Western blots; 74 kDa native PKCδ protein was present only in the brain lysates from PKCδ (+/+) mice but not from the PKCδ (−/−) mice. To first determine whether PKCδ influences PP2A activity in vivo, we compared PP2A enzyme activity in the substantia nigra of PKCδ (+/+) and PKCδ (−/−) animals. PP2A activity in the substantia nigra lysates from PKCδ (−/−) mice was significantly lower than in PKCδ (+/+) mice (FIG. 18B), supporting our findings from cell culture studies that PKCδ positively influences PP2A activity in nigral neurons.

Next we examined TH-ser40 phosphorylation status in PKCδ (−/−) animals. Determination of TH-ser40 phosphorylation in substantia nigra brain tissue revealed a significantly higher level in PKCδ (−/−) animals compared to PKCδ (+/+) animals, whereas the total TH levels were similar in the substantia nigra of these animals (FIG. 18A). Densitometric analysis of TH-ser40 phosphorylation revealed a 2-fold increase in the substantia nigra of PKCδ (−/−) animals compared to PKCδ (+/+) animals (FIG. 15A). The density of the 43 kDa β-actin band was identical in all lanes, indicating equal protein loading.

We also compared DA and DOPAC levels between PKCδ (−/−) animals and PKCδ (+/+) animals. HPLC analysis revealed that striatal DA and DOPAC levels were significantly higher in the striatum of PKCδ (−/−) animals compared to PKCδ (+/+) animals (FIG. 18C). DA levels were determined to be 28933±1077 pg/μg protein in PKCδ (−/−) compared to 19064±4272 pg/μg protein in PKCδ (+/+) animals, an increase of 52% of control. Similarly, striatal DOPAC levels were estimated to be 9664±2145.78 pg/μg protein in PKCδ (−/−) compared to 4941±2039 pg/μg protein in PKCδ (+/+) animals, an increase of 95% of control. Together, these in vivo data further demonstrate that PKCδ negatively regulates TH activity, resulting in reduced TH phosphorylation and DA synthesis.

---

What is claimed is:

1. A method of increasing dopamine synthesis in a dopamine producing cell of a mammal suffering from a disease state characterized by lack of dopamine in dopamine producing cells comprising:

contacting a dopamine producing cell with a protein kinase C delta (PKCd) inhibitor, wherein said PKCd inhibitor is (3-[(8-Cinnamoyl-5,7-dihydroxy-2,2-dimethyl-2H-1-benzopyran-6-yl)methyl]-2',4',6'-trihydroxy-5-methylacetophenone; and measuring an increase in dopamine levels.

2. The method of claim 1 wherein the PKCd inhibitor decreases protein phosphatase 2A (PP2A) activity.

3. The method of claim 1 wherein the PKCdelta (PKCd) inhibitor increases tyrosine hydroxylase (TH) activity.

4. The method of claim 3 wherein the PKCdelta (PKCd) inhibitor increases the phosphorylation of tyrosine hydroxylase (TH) at serine 40.

5. The method of claim 1 wherein the PKCd inhibitor comprises a drug.

6. The method of claim 1, wherein the disease state characterized by lack of dopamine is Parkinson's disease.

7. A method of increasing dopamine levels in central nervous system of a mammal suffering from a dopamine deficiency said method comprising: administering to the mammal in need thereof a protein kinase C delta (PKCd) inhibitor, wherein said PKCd inhibitor is (3-[(8-Cinnamoyl-5,7-dihydroxy-2,2-dimethyl-2H-1-benzopyran-6-yl)methyl]-2',4',6'-trihydroxy-5-methylacetophenone; and measuring an increase in dopamine levels.

8. The method of claim 7, wherein the dopamine deficiency is Parkinson's disease.

9. The method of claim 7, wherein the PKCd inhibitor is administered orally, intravenously, intramuscularly, subcutaneously, intraorbitally, intracapsularly, intraperitoneally, intrarectally, or intracisternally to the mammal.

10. The method of claim 7, wherein the mammal is suffering from neurodegeneration.

11. The method of claim 10, wherein the neurodegeneration is Parkinson's disease.

12. The method of claim 7 comprising: administering a therapeutically effective amount of the PKCd inhibitor.

13. The method of claim 7, wherein the PKCd inhibitor is administered in the form of a pharmaceutical composition comprising a pharmaceutically acceptable carrier.

14. The method of claim 7, wherein said PKCd inhibitor is administered subsequent, prior or during the onset of Parkinson's disease.

15. The method of claim 7, comprising administering an amount of a PKCd inhibitor effective to increase dopamine synthesis.

* * * * *